US009296703B2

(12) United States Patent
Vankayalapati et al.

(10) Patent No.: US 9,296,703 B2
(45) Date of Patent: Mar. 29, 2016

(54) SUBSTITUTED N-(3-(PYRIMIDIN-4-YL)PHENYL)ACRYLAMIDE ANALOGS AS TYROSINE RECEPTOR KINASE BTK INHIBITORS

(71) Applicant: University of Utah Research Foundation, Salt Lake City, UT (US)

(72) Inventors: Hariprasad Vankayalapati, Draper, UT (US); Venkataswamy Sorna, Salt Lake City, UT (US); Steven L. Warner, Sandy, UT (US); David J. Bearss, Alpine, UT (US); Sunil Sharma, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/433,580

(22) PCT Filed: Oct. 4, 2013

(86) PCT No.: PCT/US2013/063555
§ 371 (c)(1),
(2) Date: Apr. 3, 2015

(87) PCT Pub. No.: WO2014/055934
PCT Pub. Date: Apr. 10, 2014

(65) Prior Publication Data
US 2015/0368208 A1  Dec. 24, 2015

Related U.S. Application Data

(60) Provisional application No. 61/709,534, filed on Oct. 4, 2012.

(51) Int. Cl.
*A61K 31/505* (2006.01)
*C07D 239/42* (2006.01)
*C07D 487/04* (2006.01)
*C07F 9/6558* (2006.01)
*C07F 9/6561* (2006.01)
*C07F 9/06* (2006.01)
*A61K 31/661* (2006.01)
*A61K 31/6615* (2006.01)
*A61K 31/506* (2006.01)

(52) U.S. Cl.
CPC ............ *C07D 239/42* (2013.01); *C07D 487/04* (2013.01); *C07F 9/06* (2013.01); *C07F 9/6561* (2013.01); *C07F 9/65583* (2013.01); *A61K 31/505* (2013.01); *A61K 31/506* (2013.01); *A61K 31/661* (2013.01); *A61K 31/6615* (2013.01)

(58) Field of Classification Search
CPC ...... C07D 239/42; C07D 487/04; C07F 9/06; C07F 9/65583; C07F 9/6561; A61K 31/661; A61K 31/6615; A61K 31/505; A61K 31/506
See application file for complete search history.

(56) References Cited

U.S. PATENT DOCUMENTS

| | | | |
|---|---|---|---|
| 5,958,935 A | 9/1999 | Davis et al. | 514/275 |
| 7,655,649 B2 | 2/2010 | Bilodeau et al. | 514/227.8 |
| 7,741,330 B1 | 6/2010 | Chen et al. | 514/262.1 |
| 8,133,900 B2 | 3/2012 | Hood et al. | 514/275 |
| 8,138,199 B2 | 3/2012 | Noronha et al. | 514/275 |
| 8,268,850 B2 | 9/2012 | Li et al. | 514/275 |
| 8,324,200 B2 | 12/2012 | Li et al. | 514/210.21 |
| 8,338,439 B2 | 12/2012 | Singh et al. | 514/275 |
| 8,426,428 B2 | 4/2013 | Miller | 514/262.1 |
| 8,440,663 B2 | 5/2013 | Mann et al. | 514/235.8 |
| 8,530,480 B2 | 9/2013 | Kamenecka et al. | 514/256 |
| 8,703,767 B2 | 4/2014 | Bearss et al. | 514/234.2 |
| 8,901,120 B2 | 12/2014 | Bearss et al. | 514/235.8 |
| 9,073,947 B2* | 7/2015 | Hodous | C07D 213/68 |
| 2005/0171134 A1 | 8/2005 | Davis et al. | 544/60 |
| 2007/0021419 A1 | 1/2007 | Wang et al. | 514/235.5 |
| 2010/0190770 A1 | 7/2010 | Li et al. | 514/210.21 |
| 2010/0204221 A1 | 8/2010 | Vankayalapati et al. | 514/234.2 |
| 2012/0094999 A1 | 4/2012 | Gray et al. | 514/235.8 |
| 2014/0155385 A1* | 6/2014 | Barf | C07D 487/04 514/217.05 |
| 2014/0155406 A1* | 6/2014 | Man | C07D 487/04 514/249 |
| 2014/0162983 A1* | 6/2014 | Hodous | C07D 213/68 514/64 |
| 2015/0259363 A1* | 9/2015 | Hodous | C07D 213/68 514/64 |

FOREIGN PATENT DOCUMENTS

| | | |
|---|---|---|
| WO | WO 2010/129053 | 11/2010 |
| WO | WO 2012/135800 | 10/2012 |
| WO | WO 2012/135801 | 10/2012 |
| WO | WO 2013/085802 | 6/2013 |

(Continued)

OTHER PUBLICATIONS

A.O. Vassilev et al., 10 Current Pharmaceutical Design, 1757-1766 (2004).*
Faith Uckun et al., 136 British Journal of Haematology, 574-589 (2007).*
R.W. Hendriks et al., 18 Seminars in Immunology, 67-76 (2006).*
Faith Uckun et al., 20 Expert Opinion on Therapeutic Patents, 1457-1470 (2010).*
A. Flemming et al., 9 Nature Reviews | Drug Discovery (2010).*
L.R. Whyburn et al., 171 Journal of Immunology, 1850-1858 (2003).*

(Continued)

Primary Examiner — Alexander R Pagano
(74) Attorney, Agent, or Firm — Ballard Spahr LLP

(57) ABSTRACT

In one aspect, the invention relates to substituted N-(3-(pyrimidin-4-yl)phenyl)acrylamide analogs, derivatives thereof, and related compounds, which are useful as inhibitors of the BTK kinase; synthetic methods for making the compounds; pharmaceutical compositions comprising the compounds; and methods of using the compounds and compositions to treat disorders associated with dysfunction of the BTK kinase. This abstract is intended as a scanning tool for purposes of searching in the particular art and is not intended to be limiting of the present invention.

16 Claims, 2 Drawing Sheets

(56) References Cited

FOREIGN PATENT DOCUMENTS

| WO | WO 2014/055928 | 4/2014 |
|---|---|---|
| WO | WO 2014/055934 | 4/2014 |

OTHER PUBLICATIONS

K-H Kim et al., 21 Bioorganic & Medicinal Chemistry Letters, 6258-6263 (2011).*
Z. Pan et al., 2 ChemMedChem, 58-61 (2007).*
Alessi, et al., "Mechanism of Activation of Protein Kinase B by Insulin and IGF-1," The EMBO Journal, 1996. 15(23): pp. 6541-6551.
Angelillo-Scherrer, et al., "Role of Gas6 in Erythropoiesis and Anemia in Mice," J. Chin. Invest, 2008. 118(2): pp. 583-596.
Bellido-Martin and de Frutos. "Vitamin K-dependent actions of Gas6," Vitam Horm, 2008. 78: pp. 185-209.
Bellosta, et al., "Signaling Through the ARK Tyrosine Kinase Receptor Protects From Apoptosis in the Absence of Growth Stimulation," Oncogene, 1997. 15: pp. 2387-2397.
Bellosta, et al., "The Receptor Tyrosine Kinase ARK Mediates Cell Aggregation by Homophilic Binding," Molecular and Cellular Biology, 1995. 15(2): pp. 614-625.
Blume-Jensen et al., "Oncogenic Kinase Signaling," Nature, 2001. 411: pp. 355-365.
Braunger, et al., "Intracellular Signaling the Ufo/Axl Receptor Tyrosine Kinase Is Mediated Mainly by a Multi-Substrate Docking Site," Oncogene, 1997. 14(22): pp. 2619-2631.
Di Paolo JA, et al., "Specific Btk inhibition suppresses B cell- and myeloid; cell-mediated arthritis," *Nature Chemical Biology*, 7: 41-50 (2010).
Executive Summary: Bruton's Tyrosine Kinase (Btk) Inhibitor Programs for Oncology and Autoimmune Diseases. Pharamcyclics, 1-6. Jan. 2010.
Fridell, et al., "GAS 6 induced ASL-Mediated Chemotaxis of Vascular Smooth Muscle Cells, " The Journal of Biological Chemistry, 1998. 273: pp. 7123-7126.
Fruman, et al., "Xid-like phenotypes: a B cell signalosome takes shape," Immunity, 2000. 13(1): pp. 1-3.
Gould, et al., "Gas6 Receptor Tyrosine Kinase, Mediates Flow-induced Vascular Remodeling," Journal of Thrombosis and Haemostasis, 2005. 3(4): pp. 733-741.
Graham, et al., "Cloning and mRNA Expression Analysis of a Novel Human Protooncogene, C-mer," Cell Growth and Differentiation, 1994. 5: pp. 647-657.
Green, et al., "Overexpression of the Axl Tyrosine Kinase Receptor in Cutaneous SCC-derived Cell Lines and Tumor," Journal of Cancer, 2006. 94: pp. 1446-1451.
Hafizi, et al., "Interaction of Axl Receptor Tyrosine Kinase with C1-TEN, a Novel C1 Domain-containing Protein with Homology to Tension," Biochemical and Biophysical Research Communications, 2002. 299(5): pp. 793-800.
Hafizi, et al., "Signaling and Functional Diversity Within the Axl Subfamily of receptor Tyrosine Kinase," Cytokine & Growth Factor Review, 2006. 178: pp. 295-304.
Hafizi and Dahlback, "Gas6 and protein S. Vitamin K-dependent ligands for the Axl receptor tyrosine kinase subfamily," FEBS J., 2006. 273(23): pp. 5231-5244.
Hanada, et al., "Structure, Regulation and Function of PKB/AKI—a Major Therapeutic Target," Biochim Biophys Acta, 2004. 1697(1-2): pp. 3-16.
Hendriks, "Drug Discovery: New Btk inhibitor holds promise," Nat. Chem. Biol., 2011. 7(1): pp. 4-5.
Hubbard, et al., "Protein Tyrosine Kinase Structure and Function," Annual Review of Biochemistry, 2000. 69: p. 377.
Keating, et al., "Lymphoblastic Leukemia/Lymphoma in Mice Overexpressing the Mer (Mer TK) Receptor Tyrosine Kinase," Oncogene, 2006. 25: pp. 6092-6100.
Korshunov, et al., "Axl, A Receptor Tyrosine Kinase, Mediated Flow-induced Vascular Remodeling," Circulation Research, 2006. 98: pp. 1446-1452.
Korshunov, et al., "Axl Mediates Vascular Remodeling Induced by Deoxycorticosterone Acetate Salt Hypertension," Hypertension, 2007. 50: pp. 1057-1062.
Kurosaki, "Functional dissection of BCR signaling pathways," Curr. Opin. Immunol., 2000. 12: pp. 276-281.
Lemke, et al., "Immunobiology of the TAM Receptors," Nature Reviews Immunology, 2008. 8: pp. 327-336.
Li, et al., "Axl as a Potential Therapeutic Target in Cancer, Role of Axl in Tumor Growth, Metastasis and Angiogenesis," Oncogene, 2009. 28: pp. 3442-3455.
Linger, et al., "TAM receptor tyrosine kinases: biologic functions, signaling, and potential therapeutic targeting in human cancer," Adv Cancer Res, 2008. 100: pp. 35-83.
Manfioletti, et al., "The protein Encoded by a Growth Arrest-specific Gene (GAS 6) is a New Member of the Vitamin K-Dependent Protein Related to Protein S, a Negative Coregulator in the Blood Coagulation Cascade," Molecular and Cellular Biology, 1993. 13(8): pp. 4976-4985.
Manning, et al., "Evolution of Protein Kinase Signaling from Yeast to Man," Trends in Biochemical Sciences, 2002. 27(1): pp. 514-520.
Mark, et al., "Rse, a Novel Receptor-type Tyrosine Kinase with Homology to Axl/Ufo, is Expressed at High Levels in the Brain," Journal of Biological Chemistry, 1994. 269: pp. 10720-10728.
Mollard, et al., "Design Synthesis and Biological Evaluation of a Series of Novel Axl Kinase Inhibitors," ACS Medicinal Chemistry Letters, 2011. 2: pp. 907-912.
Rescigno, et al., "A Putative Receptor Tyrosine Kinase With Unique Structural Topology," Oncogene, 1991. 6(10): pp. 1909-1913.
Robinson, et al., "The Protein Tyrosine Family of the Human Genome," Oncogene, 2000. 19: p. 5555.
Rothlin, et al., "TAM Receptors Are Pleiotropic Inhibitors of the Innate Immune Response," Cell, 2007. 131: pp. 1124-1136.
Sainaghi, et al., "Gas6 Induced Proliferation in Prostate Carcinoma Cell Lines Expressing the Axl Receptor," Journal of Cell Physiology, 2005. 204(1): pp. 36-44.
Sawabu, et al., "Growth Arrest-Specific Gene 6 and Axl Signaling Enhances Gastric Cancer Cell Survival Via AKT Pathway," Mol. Carcinog, 2007. 46(2): pp. 155-164.
Schaeffer, et al., "Tec family kinases in lymphocyte signaling and function," Curr. Opin. Immunol., 2000. 12(3): pp. 282-288.
Shankar, et al., "Gas6/Axl Signaling Activates the Phosphatidylinositol 3-Kinase/ALK1 Pathway to Protect Oligodendracytes From Tumor Necrosis Factor Alpha-induced Apoptosis," The Journal of Neuroscience, 2006. 26(21): pp. 5638-5648.
Sharif, et al., "Twist Mediates Suppression of Inflammation by Type I IFNs and Axl," The Journal of Experimental Medicine, 2006. 203(8): pp. 1891-1901.
Shieh, et al., "Expression of Axl in Lung Adenocarcinoma and Correlation with Tumor Progression," Neoplasia, 2005. 7(12): pp. 1058-1064.
Sun, et al., "Clinical Implications of Coexpression of Growth Arrest-specific Gene 6 and Receptor Tyrosine Kinases Axl and Sky in Human Uterine Leiomyoma," Molecular Human Reproduction, 2003. 9(11): pp. 701-707.
Vajkoczy, et al., "Dominant-negative Inhibition of the Axl Receptor Tyrosine Kinase Suppresses Brian Tumor Cell Growth and Invasion and Prolongs Survival," Proceedings of the National Academy of Sciences of the United States of America, 2006. 103(15): pp. 5799-5804.
International Search Report issued Jun. 27, 2012 by the International Searching Authority for Application PCT/US2012/031768 filed Mar. 31, 2012 and later published as WO 2012/135800 on Oct. 4, 2012 (Applicant—University of Utah Research Foundation // Inventor—David J. Bearss, et al. //) (2 pages).
Written Opinion issued Jun. 27, 2012 by the International Searching Authority for Application PCT/US2012/031768 filed Mar. 31, 2012 and later published as WO 2012/135800 on Oct. 4, 2012 (Applicant—University of Utah Research Foundation // Inventor—David J. Bearss, et al. //) (4 pages).

(56) References Cited

OTHER PUBLICATIONS

Supplementary European Search Report issued Jul. 28, 2014 for EP Patent Application No. 12765879.7, which was filed Apr. 1, 2012 and published as EP 2694486 on Feb. 12, 2014 (Applicant—University of Utah Research Foundation // Inventor—David J. Bearss, et al. //) (6 pages).

International Search Report issued Jul. 24, 2012 by the International Searching Authority for Application PCT/US2012/031772 filed Apr. 1, 2012 and later published as WO 2012/135801 on Oct. 4, 2012 (Applicant—University of Utah Research Foundation // Inventor—David J. Bearss, et al. //) (2 pages).

Written Opinion issued Jul. 24, 2012 by the International Searching Authority for Application PCT/US2012/031772 filed Apr. 1, 2012 and later published as WO 2012/135801 on Oct. 4, 2012 (Applicant—University of Utah Research Foundation // Inventor—David J. Bearss, et al. //) (5 pages).

Restriction Requirement issued Jul. 10, 2013 for U.S. Appl. No. 13/436,963, filed Apr. 1, 2012 and issued as U.S. Pat. No. 8,703,767 on Apr. 22, 2014 (Applicant—University of Utah Research Foundation // Inventor—David J. Bearss, et al. //) (6 pages).

Reponse to Restriction Requirement filed Aug. 12, 2013 for U.S. Appl. No. 13/436,963, Apr. 1, 2012 and issued as U.S. Pat. No. 8,703,767 on Apr. 22, 2014 (Applicant—University of Utah Research Foundation // Inventor—David J. Bearss, et al. //) (10 pages).

Notice of Allowance issued Dec. 6, 2013 for U.S. Appl. No. 13/436,963, filed Apr. 1, 2012 and issued as U.S. Pat. No. 8,703,767 on Apr. 22, 2014 (Applicant—University of Utah Research Foundation // Inventor—David J. Bearss, et al. //) (10 pages).

Issue Notification issued Apr. 2, 2014 for U.S. Appl. No. 13/436,963, filed Apr. 1, 2012 and issued as U.S. Pat. No. 8,703,767 on Apr. 22, 2014 (Applicant—University of Utah Research Foundation // Inventor—David J. Bearss, et al. //) (1 page).

International Search Report issued May 1, 2014 by the International Searching Authority for Application PCT/US2013/063549 filed Oct. 4, 2013 and later published as WO 2014/055928 on Oct. 10, 2014 (Applicant—University of Utah Research Foundation // Inventor—David J. Bearss, et al. //) (4 pages).

Written Opinion issued May 1, 2014 by the International Searching Authority for Application PCT/US2013/063549 filed Oct. 4, 2013 and later published as WO 2014/055928 on Apr. 10, 2014 (Applicant—University of Utah Research Foundation // Inventor—David J. Bearss, et al. //) (6 pages).

International Preliminary Report on Patentability issued May 1, 2014 by the International Searching Authority for Application PCT/US2013/063549 filed Oct. 4, 2013 and later published as WO 2014/055928 on Apr. 10, 2014 (Applicant—University of Utah Research Foundation // Inventor—David J. Bearss, et al. //) (1 page).

International Search Report issued May 1, 2014 by the International Searching Authority for Application PCT/US2013/063555 filed Oct. 4, 2013 and later published as WO 2014/055934 on Apr. 10, 2014 (Applicant—University of Utah Research Foundation // Inventor—David J. Bearss, et al. //) (4 pages).

Written Opinion issued May 1, 2014 by the International Searching Authority for Application PCT/US2013/063555 filed Oct. 4, 2013 and later published as WO 2014/055934 on Apr. 10, 2014 (Applicant—University of Utah Research Foundation // Inventor—David J. Bearss, et al. //) (6 pages).

International Preliminary Report on Patentability issued May 1, 2014 by the International Searching Authority for Application PCT/US2013/063555 filed Oct. 4, 2013 and later published as WO 2014/055934 on Apr. 10, 2014 (Applicant—University of Utah Research Foundation // Inventor—David J. Bearss, et al. //) (1 page).

* cited by examiner

SUBSTITUTED N-(3-(PYRIMIDIN-4-YL)PHENYL)ACRYLAMIDE ANALOGS AS TYROSINE RECEPTOR KINASE BTK INHIBITORS

CROSS-REFERENCE TO RELATED APPLICATIONS

This Application claims benefit of priority under 35 U.S.C. 371 of PCT/US2013/063555, filed Oct. 4, 2013, which claims the benefit under 35 U.S.C. 119(e) of U.S. Provisional Application No. 61/709,534 filed on Oct. 4, 2012. The contents of the prior international and provisional applications are hereby incorporated by reference herein in their entirety.

BACKGROUND

Protein kinases play an important role in a large percentage of the biochemical processes that regulate the functions of cells that are critical in tumor developments including; cell proliferation, genomic repair, apoptosis, migration, and invasion. These proteins serve, in many cases, as molecular "switches" regulating the activity of target proteins through the process of phosphorylation. In normal cell physiology, the coordination of multiple kinases is a tightly regulated process allowing the cell to function in a manner in which it was designed. Protein kinases and phosphatases play a prominent role in the tumorigenic process. Normal cell physiology is dependent on the appropriate balance between kinase and phosphatase activity to keep important signaling pathways within tolerated levels. Mutations in the genes that encode these proteins often lead to aberrant signaling that lays the foundation for changes in cellular function. Alterations in numerous protein kinase pathways ultimately lead to deregulation of cellular function that affect pathways that are hallmarks of the tumor phenotype.

Bruton's tyrosine kinase (BTK), a member of the Tec family of non-receptor tyrosine kinases, plays an essential role in the B-cell signaling pathway linking cell surface B-cell receptor (BCR) stimulation to downstream intracellular responses. It is required for the normal development and function of B-lymphocytes in humans and mice as evidenced by mutations in the Btk gene that result in the X-linked agammaglobulinemia (XLA) phenotype in humans and a less severe X-linked immunodeficiency phenotype (XID) in mice (e.g., D. A. Fruman, et al., (2000), Immunity 13:1-3). Btk is expressed in all hematopoietic cells types except T lymphocytes and natural killer cells, and participates in a number of TLR and cytokine receptor signaling pathways including lipopolysaccharide (LPS) induced TNF-α production in macrophages, suggesting a general role for BTK in immune regulation.

BTK contains an amino-terminal pleckstrin homology (PH) domain, followed by a Tec homology (TH) domain, regulatory Src homology (SH3, SH2) domains, and a C-terminal kinase (SH1) domain. In unstimulated B cells, Btk is localized to the cytoplasm where it is catalytically inactive, presumably due to a tertiary conformation arising from intramolecular interactions between the kinase domain and the SH2 and/or SH3 domains that block access of substrates to the active site. After BCR stimulation, BTK is recruited to the cell membrane via interactions between the N-terminal PH domain and cell membrane phosphoinositides. Membrane-associated BTK is then phosphorylated at Tyr 551 in the activation loop by Src family kinases. Subsequent BTK auto-phosphorylation at Tyr 223 stabilizes the active conformation and fully activates BTK kinase activity. Activated BTK phosphorylates phospholipase (PLCγ), initiating calcium mobilization and generating diacylglycerol (DAG) as secondary signals, eventually leading to transcriptional activation and amplification of BCR stimulation.

In summary, BTK is a central activator of several signaling pathways that are frequently altered in mammalian cancers making it an attractive target for therapeutic intervention. Consequently, there is a great need in the art for effective inhibitors of BTK.

SUMMARY

In accordance with the purpose(s) of the invention, as embodied and broadly described herein, the invention, in one aspect, relates to compounds useful as inhibitors of the PI3K/Akt pathway, compounds useful as inhibitors of BTK, methods of making same, pharmaceutical compositions comprising same, and methods of treating disorders of uncontrolled cellular proliferation using same.

Disclosed are compounds having a structure represented by a formula:

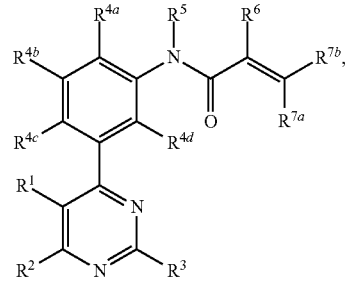

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

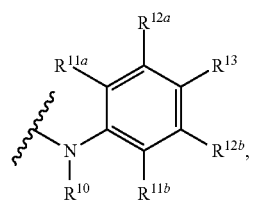

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

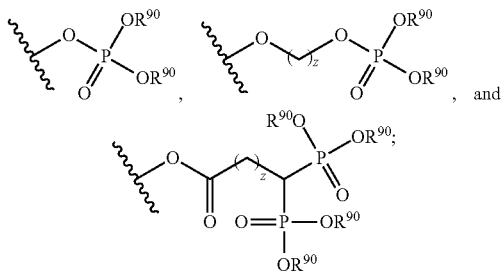

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

Also disclosed are pharmaceutical compositions comprising a therapeutically effective amount of one or more disclosed compounds, or pharmaceutically acceptable salt, solvate, or polymorph thereof, and a pharmaceutically acceptable carrier.

Also disclosed are methods for the treatment of a disorder of uncontrolled cellular proliferation in a mammal, the method comprising the step of administering to the mammal an effective amount of least one disclosed compound, or pharmaceutically acceptable salt, solvate, or polymorph thereof, thereby treating the disorder.

A method for the treatment of an inflammatory disorder in a mammal, the method comprising the step of administering to the mammal an effective amount of least one disclosed compound, or pharmaceutically acceptable salt, solvate, or polymorph thereof, thereby treating the disorder.

Also disclosed are methods for decreasing kinase activity in a mammal, the method comprising the step of administering to the mammal an effective amount of least one disclosed compound, or pharmaceutically acceptable salt, solvate, or polymorph thereof, thereby decreasing kinase activity in the mammal.

Also disclosed are methods for decreasing kinase activity in at least one cell, the method comprising the step of contacting the at least one cell with an effective amount of least one disclosed compound, or pharmaceutically acceptable salt, solvate, or polymorph thereof, thereby decreasing kinase activity in the cell.

Also disclosed are uses of a disclosed compound, a disclosed product of making, or a pharmaceutically acceptable salt, solvate, or polymorph thereof.

Also disclosed are uses of a disclosed compound, a disclosed product of making, or a pharmaceutically acceptable salt, solvate, or polymorph thereof, in the manufacture of a medicament for the treatment of a disorder associated with a kinase dysfunction in a mammal.

Also disclosed are methods for the manufacture of a medicament to inhibit the BTK tyrosine kinase in a mammal comprising combining at least one disclosed compound or at least one disclosed product of making with a pharmaceutically acceptable carrier or diluent.

Also disclosed are kits comprising at least one disclosed compound, or a pharmaceutically acceptable salt, solvate, or polymorph thereof, and one or more of: (a) at least one agent known to increase kinase activity; (b) at least one agent known to decrease kinase activity; (c) at least one agent known to treat a disorder of uncontrolled cellular proliferation; or (d) instructions for treating a disorder associated with uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
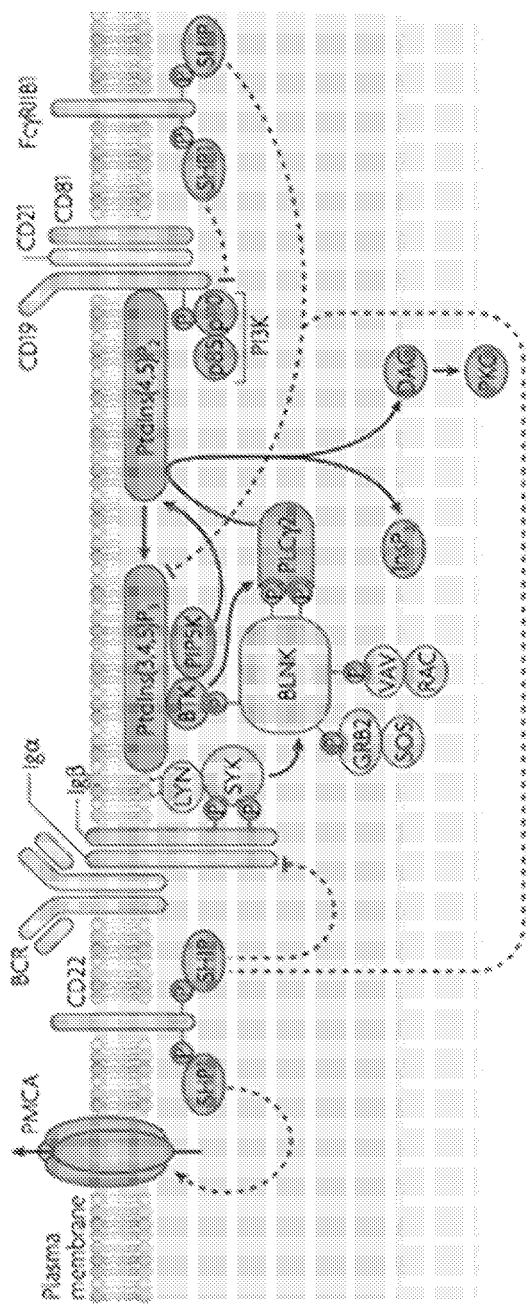
FIG. 1 shows a schematic representation of the signaling network for B cell activation.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the terms "BTK," "receptor tyrosine kinase BTK," and "BTK receptor tyrosine kinase" can be used interchangeably and refer to a protein kinase encoded by the BTK gene, which has a gene map locus of Xq21.3-q22. The term BTK refers to a native protein that has 659 amino acids with a molecular weight of about 76281 Da. The term refers to that protein which has the EC number 2.7.10.2. The term BTK is inclusive of the splice isoforms, and also is inclusive of such alternative designations as: agammaglobulinaemia tyrosine kinase, AGMX1, AT, ATK, B-cell progenitor kinase, BPK, B-cell progenitor kinase, Bruton agammaglobulinemia tyrosine kinase, Bruton tyrosine kinase, BTK; dominant-negative kinase-deficient Bruton's tyrosine kinase, IMD1, MGC126261, MGC126262, PSCTK1, Tyrosine-protein kinase BTK, and XLA as used by those skilled in the art.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a protein kinase dysfunction prior to the administering step. In some aspects of the disclosed method, the subject has been diagnosed with a need for inhibition of a protein kinase prior to the administering step.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a protein kinase dysfunction prior to the administering step. In some aspects of the disclosed method, the subject has been diagnosed with a need for inhibition of a protein kinase prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit a protein kinase. As a further example, "diagnosed with a need for inhibition of a protein kinase" refers to having been subjected to a physical examination by a person of skill, for example, a physician, and found to have a condition characterized by a protein kinase dysfunction. Such a diagnosis can be in reference to a disorder, such as a disorder of uncontrolled cellular proliferation, cancer and the like, as discussed herein. For example, the term "diagnosed with a need for inhibition of protein kinase activity" refers to having been subjected to a physical examination by a person of skill, for example, a physician, and found to have a condition that can be diagnosed or treated by inhibition of protein kinase activity. For example, "diagnosed with a need for treatment of one or more disorders of uncontrolled cellular proliferation associated with a protein kinase dysfunction" means having been subjected to a physical examination by a person of skill, for example, a physician, and found to have one or more disorders of uncontrolled cellular proliferation associated with a protein kinase dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of protein kinase activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target protein kinase, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "EC$_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an EC$_{50}$ can refer to the concentration of a substance that is required for 50% agonism or activation in vivo, as further defined elsewhere herein. In a further aspect, EC$_{50}$ refers to the concentration of agonist or activator that provokes a response halfway between the baseline and maximum response.

As used herein, "IC$_{50}$," is intended to refer to the concentration of a substance (e.g., a compound or a drug) that is required for 50% inhibition of a biological process, or component of a process, including a protein, subunit, organelle, ribonucleoprotein, etc. For example, an IC$_{50}$ can refer to the concentration of a substance that is required for 50% inhibition in vivo or the inhibition is measured in vitro, as further defined elsewhere herein. Alternatively, IC$_{50}$ refers to the half maximal (50%) inhibitory concentration (IC) of a substance. The inhibition can be measured in a cell-line such as Ramos (RA-1), Granta-519, BxPC-3 or OPM-2. In a yet further aspect, the inhibition is measured in a cell-line, e.g. HEK-293 or HeLa, transfected with a mutant or wild-type mammalian protein kinase, e.g. Btk.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The cycloalkyl group can be substituted or unsubstituted. The cycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The cycloalkenyl group can be substituted or unsubstituted. The cycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The cycloalkynyl group can be substituted or unsubstituted. The cycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formulas —NH(-alkyl) and —N(-alkyl)$_2$, and where alkyl is as described herein. The alkyl group can be a C1 alkyl, C1-C2 alkyl, C1-C3 alkyl, C1-C4 alkyl, C1-05 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl) amino group, (tert-butyl)amino group, pentylamino group, isopentylamino group, (tert-pentyl)amino group, hexylamino group, N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "monoalkylamino" as used herein is represented by the formula —NH(-alkyl), where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$, where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. It is understood that each alkyl group can be independently varied, e.g. as in the representative compounds such as N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted, and the heteroaryl group can be monocyclic, bicyclic or multicyclic aromatic ring. The heteroaryl group can be substituted with one or more groups including, but not limited to, alkyl, cycloalkyl, alkoxy, amino, ether, halide, hydroxy, nitro, silyl, sulfo-oxo, or thiol as described herein. It is understood that a heteroaryl group may be bound either through a heteroatom in the ring, where chemically possible, or one of carbons comprising the heteroaryl ring.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Non-limiting examples of heteroaryl rings include furyl, pyrrolyl, pyrazolyl, imidazolyl, triazolyl, pyridinyl, pyridazinyl, pyrimidinyl, pyrazinyl, azepinyl, triazinyl, thienyl, oxazolyl, thiazolyl, oxadiazolyl, oxatriazolyl, oxepinyl, thiepinyl, diazepinyl, benzofuranyl, thionapthene, indolyl, benzazolyl, pyranopyrrolyl, isoindazolyl, indoxazinyl, benzoxazolyl, quinolinyl, isoquinolinyl, benzodiazonyl, naphthyridinyl, benzothienyl, pyridopyridinyl, acridinyl, carbazolyl and purinyl rings.

The term "monocyclic heteroaryl," as used herein, refers to a monocyclic ring system which is aromatic and in which at least one of the ring atoms is a heteroatom. Monocyclic heteroaryl groups include, but are not limited to, the following exemplary groups: pyridine, pyrimidine, furan, thiophene, pyrrole, isoxazole, isothiazole, pyrazole, oxazole, thiazole, imidazole, oxadiazole, including, 1,2,3-oxadiazole, 1,2,5-oxadiazole and 1,3,4-thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3, 4-tetrazole and 1,2,4,5-tetrazole, pyridazine, pyrazine, triazine, including 1,2,4-triazine and 1,3,5-triazine, tetrazine, including 1,2,4,5-tetrazine, and the like. Monocyclic heteroaryl groups are numbered according to standard chemical nomenclature.

The term "bicyclic heteroaryl," as used herein, refers to a ring system comprising a bicyclic ring system in which at least one of the two rings is aromatic and at least one of the two rings contains a heteroatom. Bicyclic heteroaryl encompasses ring systems wherein an aromatic ring is fused with another aromatic ring, or wherein an aromatic ring is fused with a non-aromatic ring. Bicyclic heteroaryl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Examples of bicyclic heteroaryl groups include without limitation indolyl, isoindolyl, indolyl, indolinyl, indolizinyl, quinolinyl, isoquinolinyl, benzofuranyl, bexothiophenyl, indazolyl, benzimidazolyl, benzothiazinyl, benzothiazolyl, purinyl, quinolizyl, quinolyl, isoquinolyl, cinnolinyl, phthalazinyl, quinazolizinyl, quinoxalyl, naphthyridinyl, and pteridyl. Bicyclic heteroaryls are numbered according to standard chemical nomenclature.

The term "heterocycloalkyl" as used herein refers to an aliphatic, partially unsaturated or fully saturated, 3- to 14-membered ring system, including single rings of 3 to 8 atoms and bi- and tricyclic ring systems where at least one of the carbon atoms of the ring is replaced with a heteroatom such as, but not limited to, nitrogen, oxygen, sulfur, or phosphorus. A heterocycloalkyl can include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, the following exemplary groups: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The term heterocycloalkyl group can also be a C2 heterocycloalkyl, C2-C3 heterocycloalkyl, C2-C4 heterocycloalkyl, C2-C5 heterocycloalkyl, C2-C6 heterocycloalkyl, C2-C7 heterocycloalkyl, C2-C8 heterocycloalkyl, C2-C9 heterocycloalkyl, C2-C10 heterocycloalkyl, C2-C11 heterocycloalkyl, and the like up to and including a C2-C14 heterocycloalkyl. For example, a C2 heterocycloalkyl comprises a group which has two carbon atoms and at least one heteroatom, including, but not limited to, aziridinyl, diazetidinyl, oxiranyl, thiiranyl, and the like. Alternatively, for example, a C5 heterocycloalkyl comprises a group which has five carbon atoms and at least one heteroatom, including, but not limited to, piperidinyl, tetrahydropyranyl, tetrahydrothiopyranyl, diazepanyl, and the like. It is understood that a heterocycloalkyl group may be bound either through a heteroatom in the ring, where chemically possible, or one of carbons comprising the heterocycloalkyl ring. The heterocycloalkyl group can be substituted or unsubstituted. The heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "hydroxyl" or "hydroxyl," as used herein can be used interchangeably and refers to a group represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido," as used herein can be used interchangeably and refers to a group represented by the formula —$N_3$.

The term "nitro" as used herein is represented by the formula —$NO_2$.

The term "nitrile" or "cyano," as used herein can be used interchangeably and refers to a group represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, —$(CH_2)_{0-4}$ SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides—including chloro, bromo, and iodo—and pseudohalides (sulfonate esters)—including triflate, mesylate, tosylate, and brosylate. It is also contemplated that a hydroxyl moiety can be converted into a leaving group via Mitsunobu reaction.

The term "protecting group" means a group which protects one or more functional groups of a compound giving rise to a protected derivative of the specified compound. Functional groups which may be protected include, by way of example, amino groups, hydroxyl groups, and the like. Protecting groups are well-known to those skilled in the art and are described, for example, in T. W. Greene and G. M. Wuts, Protecting Groups in Organic Synthesis, Third Edition, Wiley, New York, 1999, and references cited therein.

The term "amino-protecting group" means a protecting group suitable for preventing undesired reactions at an amino group, include, but are not limited to, tert-butoxycarbonyl (BOC), trityl (Tr), benzyloxycarbonyl (Cbz), 9-fluorenylmethoxycarbonyl (FMOC), formyl, trimethylsilyl (TMS), tert-butyldimethylsilyl (TBS), benzyl, p-methoxybenzyl, p-fluorobenzyl, p-chlorobenzyl, p-bromobenzyl, diphenylmethyl naphtylmethyl, and the like.

The term "hydroxyl-protecting group" means a protecting group suitable for preventing undesirable reactions at a hydroxyl group. Representative hydroxyl-protecting groups include, but are not limited to, silyl groups including tri(1-6C)-alkylsilyl groups, such as trimethylsilyl (TMS), triethylsilyl (TES), tert-butyldimethylsilyl (TBS), and the like; esters (acyl groups) including (1-6C)-alkanoyl groups, such as formyl, acetyl, and the like; arylmethyl groups, such as benzyl (Bn), p-methoxybenzyl (PMB), 9-fluorenylmethyl (Fm), diphenylmethyl (benzhydryl, DPM), and the like.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

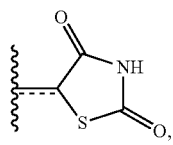

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. For example, a compound prefixed with (−) or l meaning that the compound is levorotatory, and a compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance.

The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{18}F$, and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

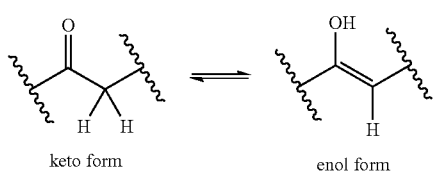

keto form     enol form

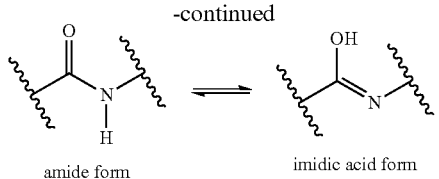

amide form     imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

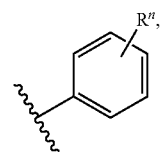

which is understood to be equivalent to a formula:

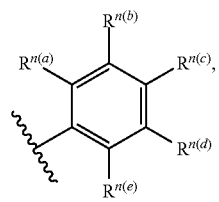

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of protein kinase. In a further aspect, the compounds are useful as inhibitors of Bruton's tyrosine kinase (BTK). Moreover, in one aspect, the compounds of the invention are useful in the treatment of disorders of uncontrolled cellular proliferations. In a further aspect, the disorder of uncontrolled cellular proliferation is a cancer or a tumor. In a further aspect, the compounds of the invention are useful in the treatment of disorders of inflammation. In a still further aspect, the disorder of uncontrolled cellular proliferation is associated with BTK dysfunction, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

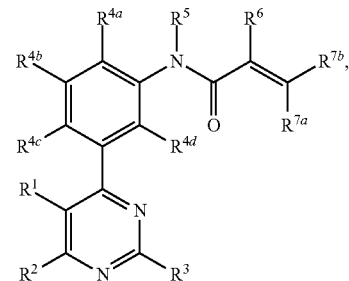

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

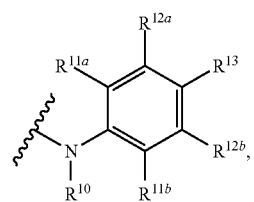

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

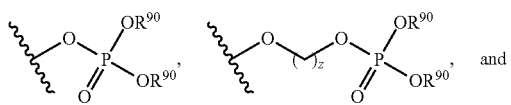

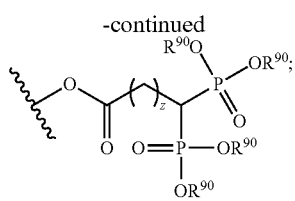

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In a further aspect, the compound has a structure represented by a formula:

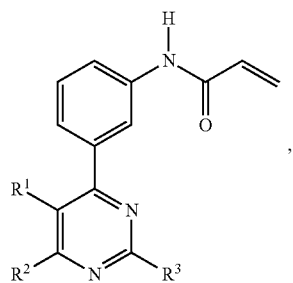

and wherein all variables are as defined herein.

In a further aspect, the compound has a structure represented by a formula:

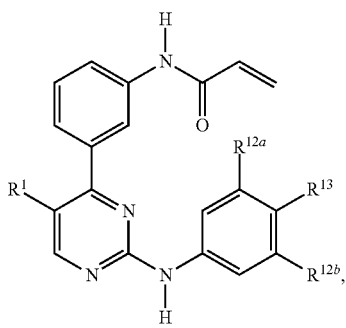

wherein $R^1$ is halogen; and wherein all variables are as defined herein.

In a further aspect, the compound has a structure represented by a formula selected from:

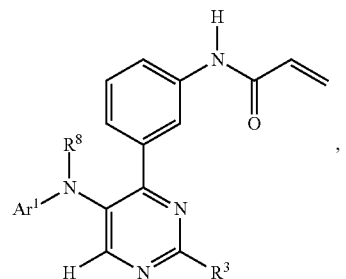

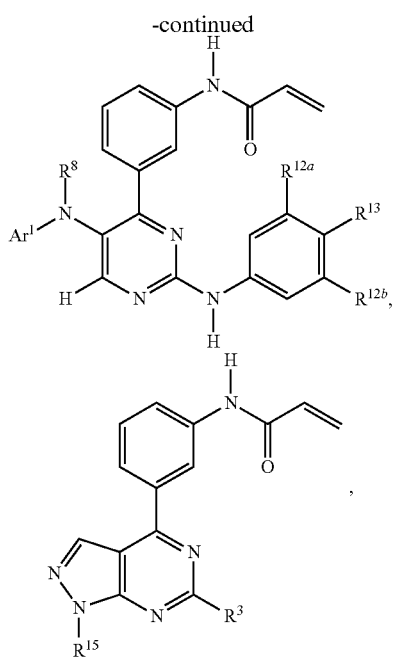

wherein $R^{15}$ is selected from hydrogen and C1-C6 alkyl; and wherein all variables are as defined herein.

In a further aspect, the compound has a structure represented by a formula:

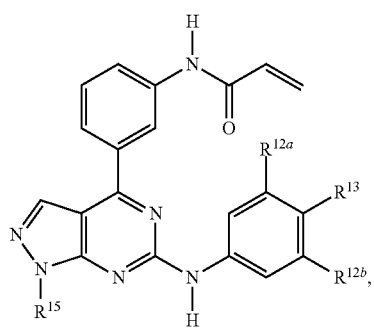

hydrogen, C1-C6 alkyl, C1-C6 haloalkyl, and C1-C6 polyhaloalkyl; and wherein all variables are as defined herein.

In a further aspect, the compound has a structure represented by a formula:

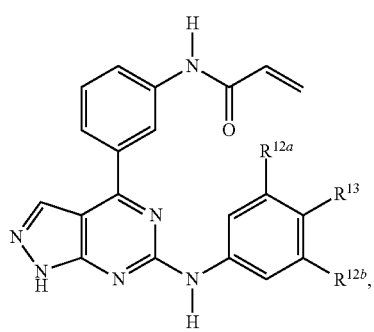

and wherein all variables are as defined herein.

In a further aspect, the compound has a structure represented by a formula:

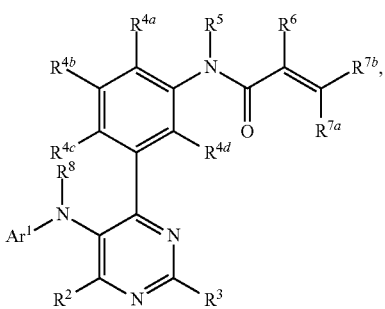

and wherein all variables are as defined herein.

In a further aspect, the compound has a structure represented by a formula:

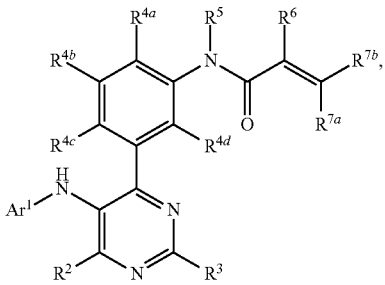

and wherein all variables are as defined herein.

In a further aspect, the compound has a structure represented by a formula:

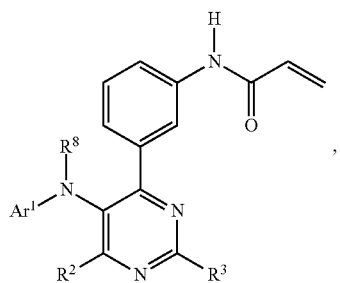

and wherein all variables are as defined herein.

In a further aspect, the compound has a structure represented by a formula:

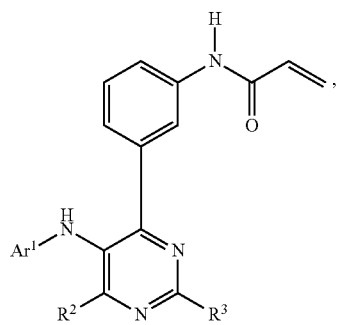

and wherein all variables are as defined herein.

In a further aspect, the compound has a structure represented by a formula:

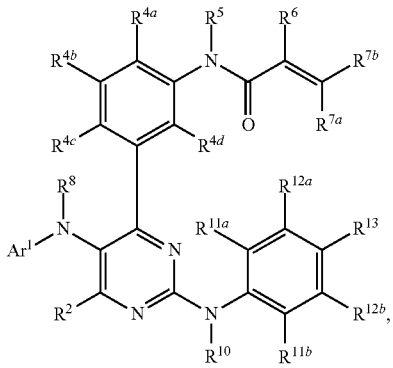

and wherein all variables are as defined herein.

In a further aspect, the compound has a structure represented by a formula:

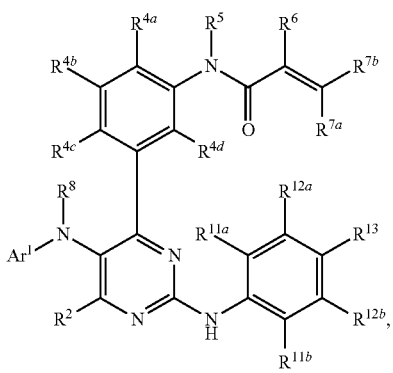

and wherein all variables are as defined herein.

In a further aspect, the compound has a structure represented by a formula:

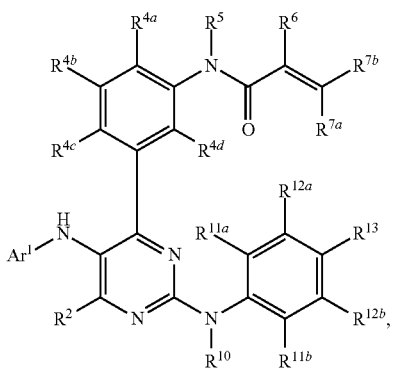

and wherein all variables are as defined herein.

In a further aspect, the compound has a structure represented by a formula:

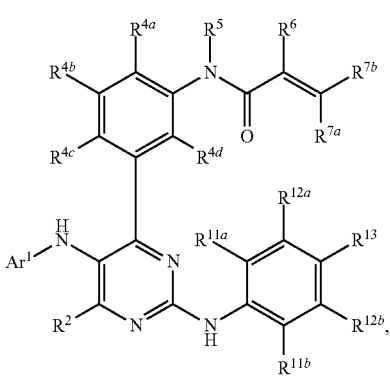

and wherein all variables are as defined herein.

In a further aspect, the compound has a structure represented by a formula:

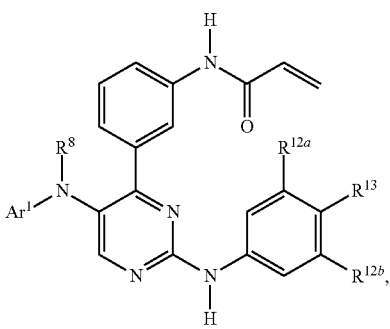

and wherein all variables are as defined herein.

In a further aspect, the compound has a structure represented by a formula:

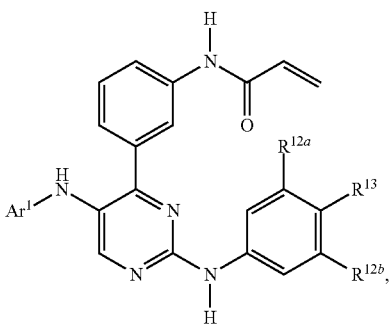

and wherein all variables are as defined herein.

In a further aspect, the compound has a structure represented by a formula:

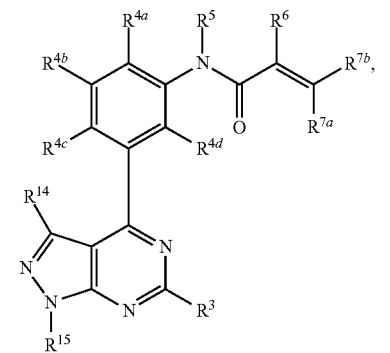

wherein $R^{14}$ is selected from hydrogen, halogen, and C1-C6 alkyl; and wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

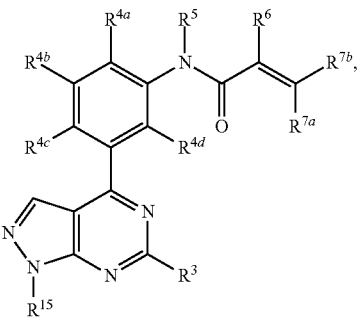

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

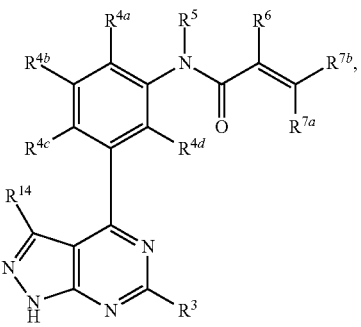

wherein $R^{14}$ is selected from hydrogen, halogen, and C1-C6 alkyl; and wherein all variables are as defined herein.

In a further aspect, the compound has a structure represented by a formula:

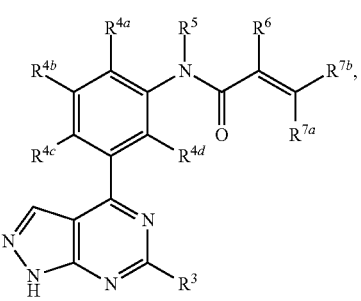

and wherein all variables are as defined herein.

In a further aspect, the compound has a structure represented by a formula:

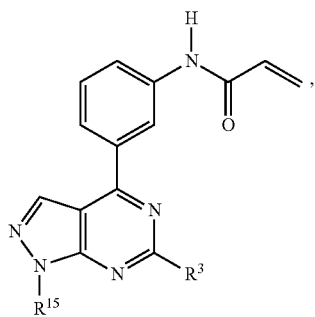

and wherein all variables are as defined herein.

In a further aspect, the compound has a structure represented by a formula:

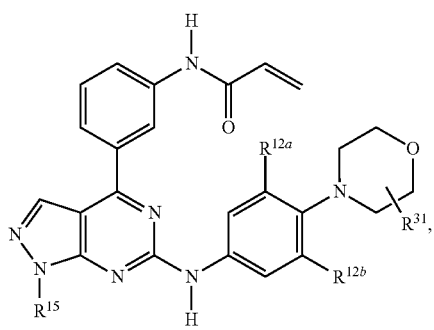

wherein $R^{15}$ is selected from hydrogen, C1-C6 alkyl, C1-C6 haloalkyl, and C1-C6 polyhaloalkyl; wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

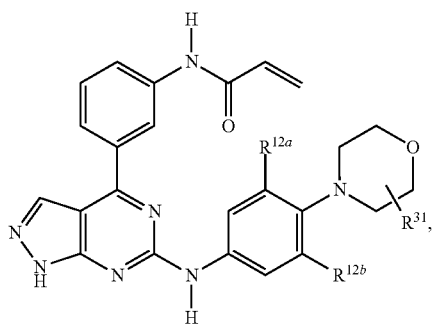

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

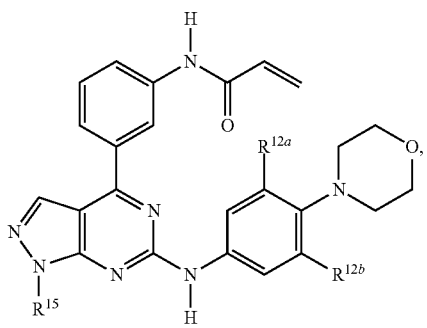

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

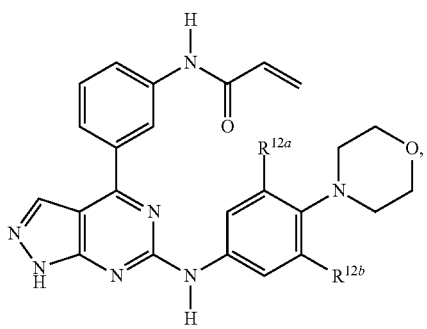

and wherein all variables are as defined herein.

In a further aspect, the compound has a structure represented by a formula:

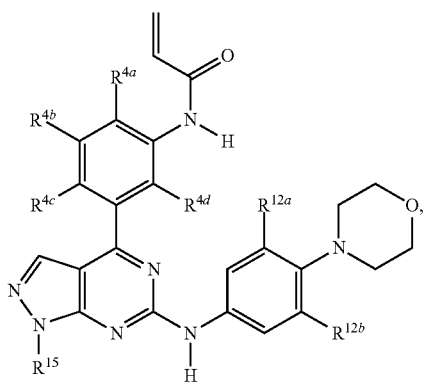

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

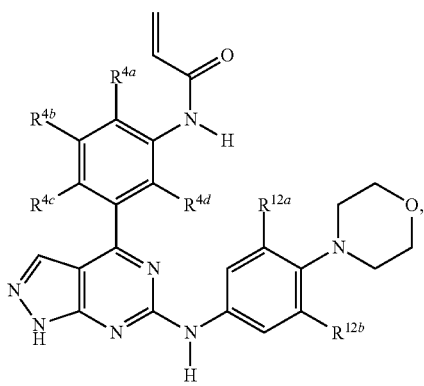

and wherein all variables are as defined herein.

In a further aspect, the compound has a structure represented by a formula:

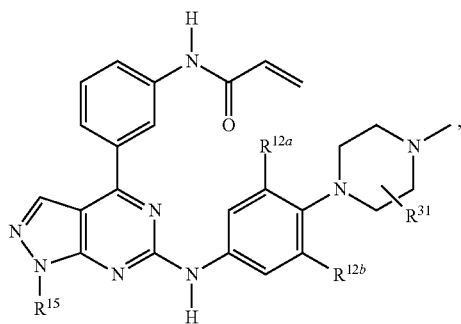

wherein $R^{15}$ is selected from hydrogen, C1-C6 alkyl, C1-C6 haloalkyl, and C1-C6 polyhaloalkyl; wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

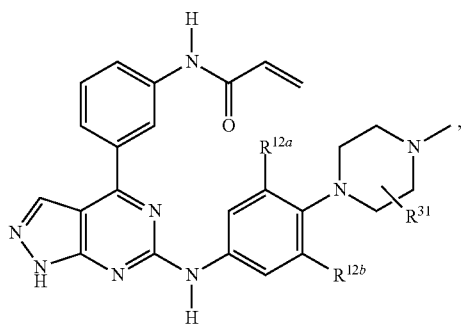

wherein $R^{15}$ is selected from hydrogen, C1-C6 alkyl, C1-C6 haloalkyl, and C1-C6 polyhaloalkyl; wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

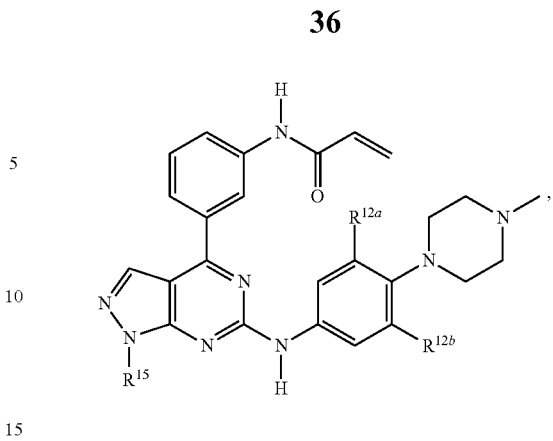

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

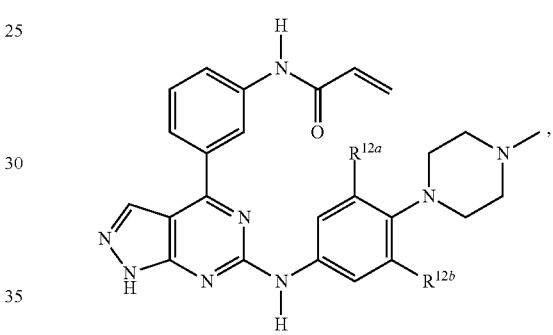

and wherein all variables are as defined herein.

In a further aspect, the compound has a structure represented by a formula:

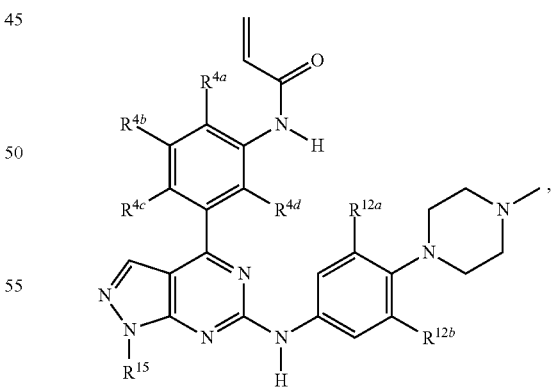

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

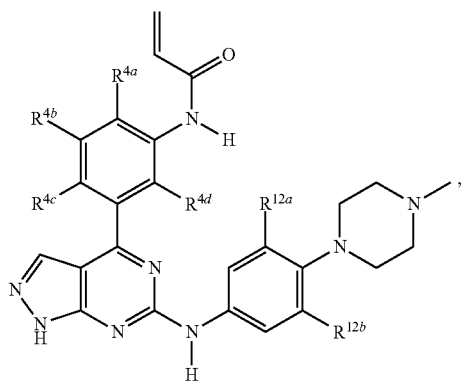

and wherein all variables are as defined herein.

In a further aspect, the compound has a structure represented by a formula:

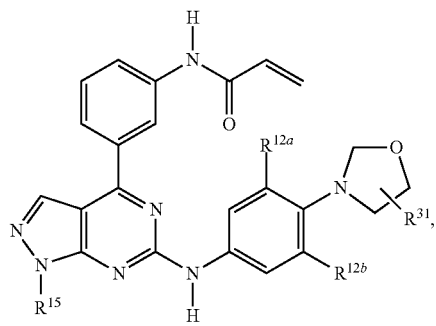

wherein $R^{15}$ is selected from hydrogen, C1-C6 alkyl, C1-C6 haloalkyl, and C1-C6 polyhaloalkyl; and wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

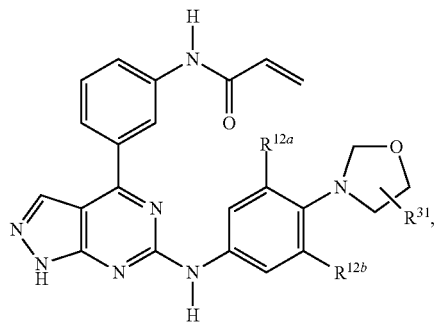

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

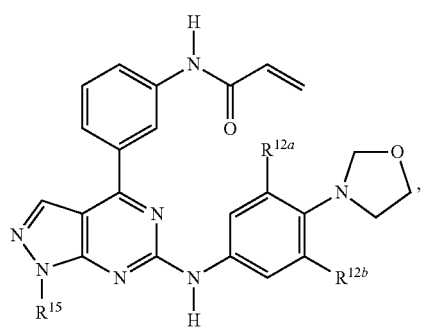

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

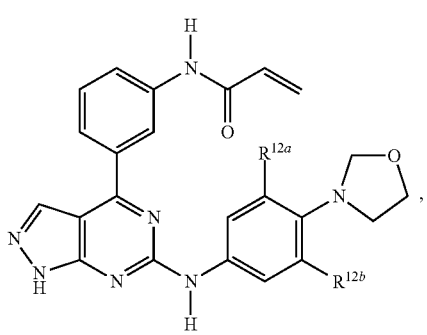

and wherein all variables are as defined herein.

In a further aspect, the compound has a structure represented by a formula:

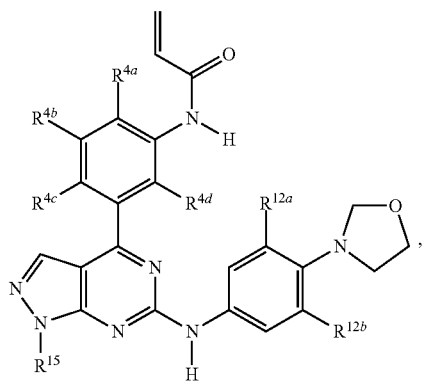

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

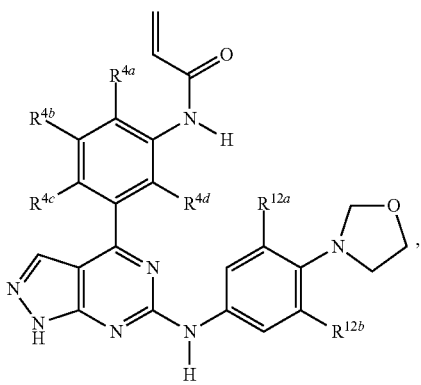

and wherein all variables are as defined herein.

In a further aspect, the compound has a structure represented by a formula:

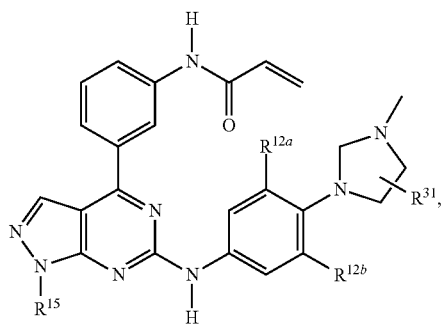

wherein $R^{15}$ is selected from hydrogen, C1-C6 alkyl, C1-C6 haloalkyl, and C1-C6 polyhaloalkyl; wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

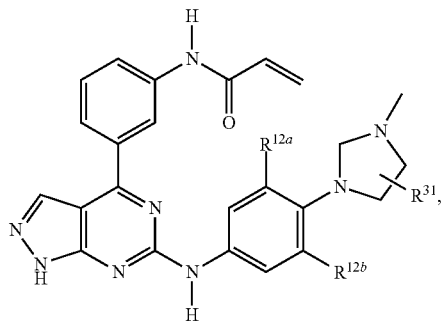

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

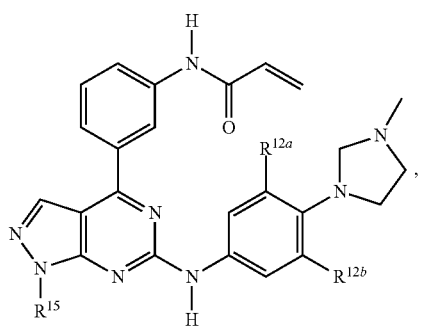

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

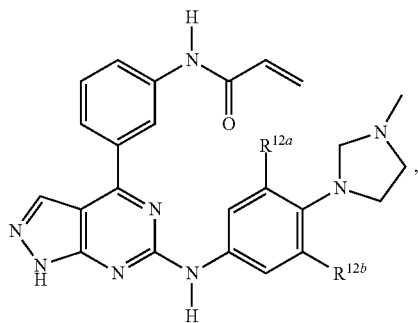

and wherein all variables are as defined herein.

In a further aspect, the compound has a structure represented by a formula:

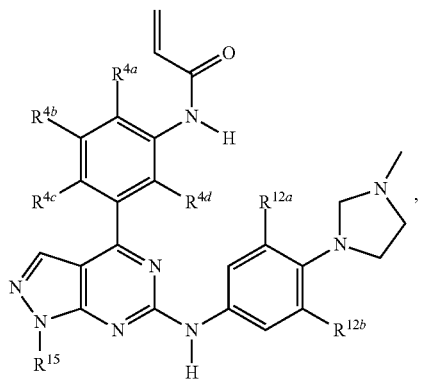

wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

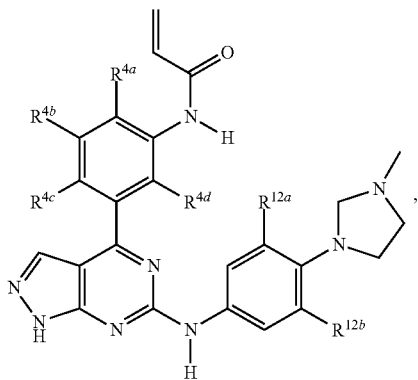

and wherein all variables are as defined herein.

In a further aspect, the compound has a structure represented by a formula:

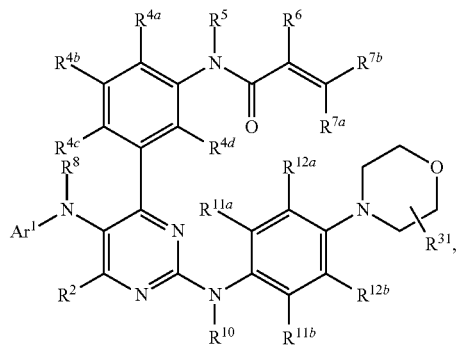

wherein $R^{15}$ is selected from hydrogen, C1-C6 alkyl, C1-C6 haloalkyl, and C1-C6 polyhaloalkyl; wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

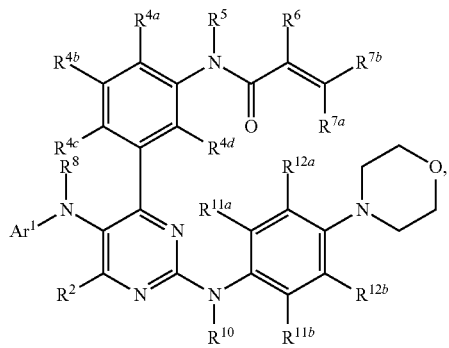

and wherein all variables are as defined herein.

In a further aspect, the compound has a structure represented by a formula:

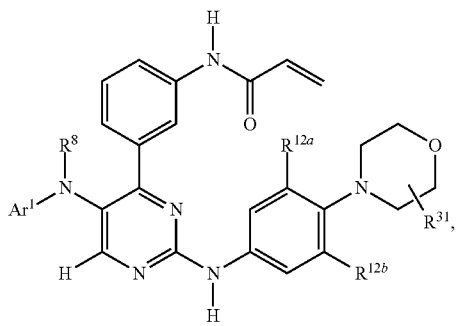

and wherein all variables are as defined herein.

In a further aspect, the compound has a structure represented by a formula:

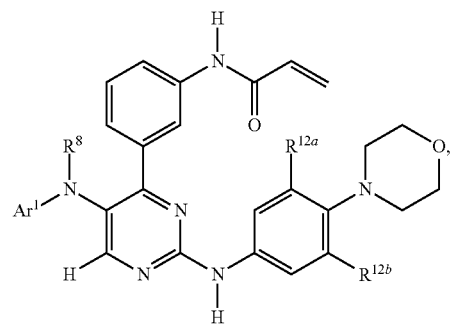

and wherein all variables are as defined herein.

In a further aspect, the compound has a structure represented by a formula:

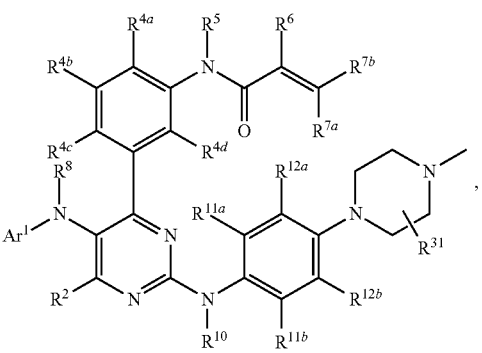

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

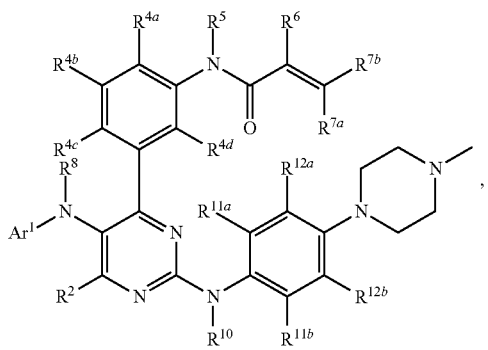

and wherein all variables are as defined herein.

In a further aspect, the compound has a structure represented by a formula:

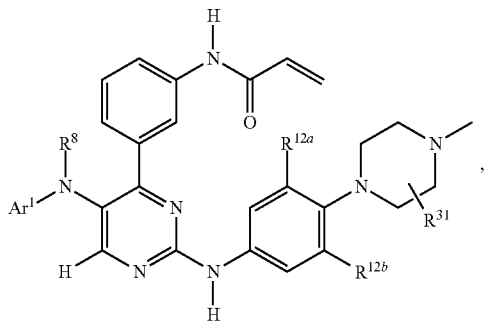

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen; and wherein all variables are as defined herein.

In a further aspect, the compound has a structure represented by a formula:

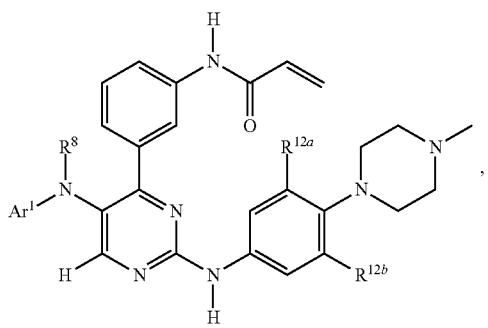

and wherein all variables are as defined herein.

In a further aspect, the compound has a structure represented by a formula:

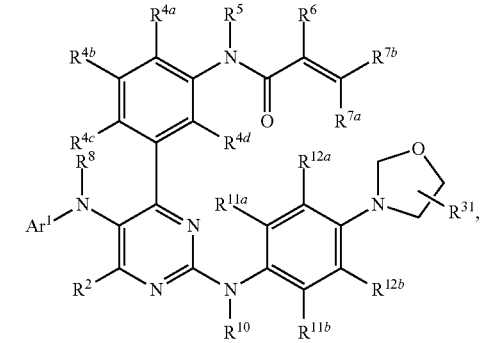

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

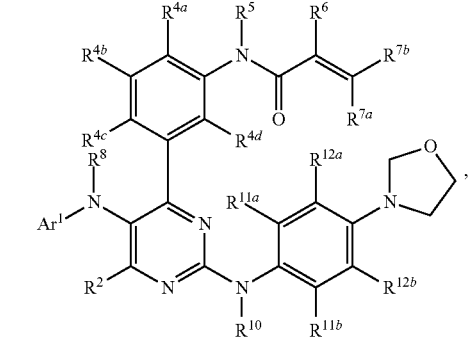

and wherein all variables are as defined herein.

In a further aspect, the compound has a structure represented by a formula:

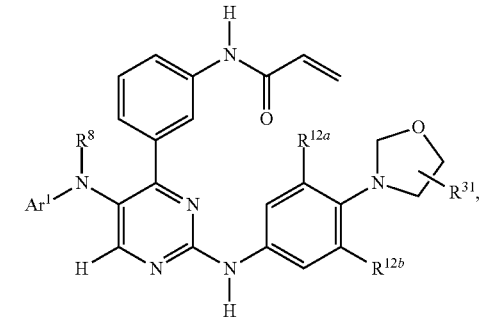

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

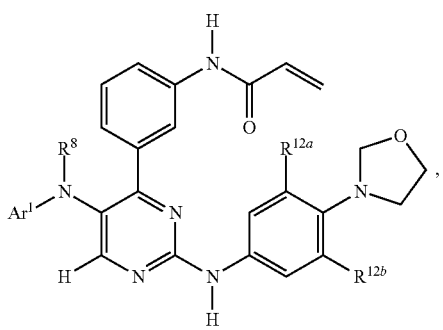

and wherein all variables are as defined herein.

In a further aspect, the compound has a structure represented by a formula:

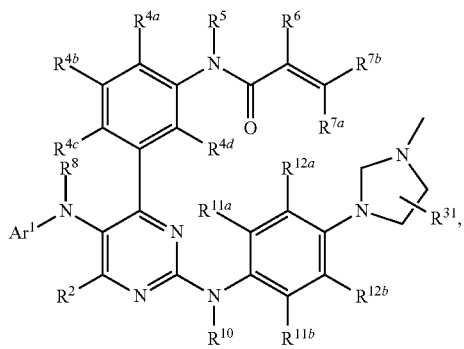

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

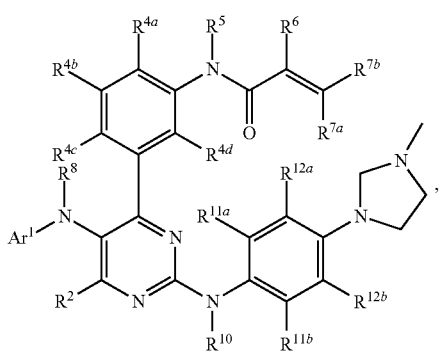

and wherein all variables are as defined herein.

In a further aspect, the compound has a structure represented by a formula:

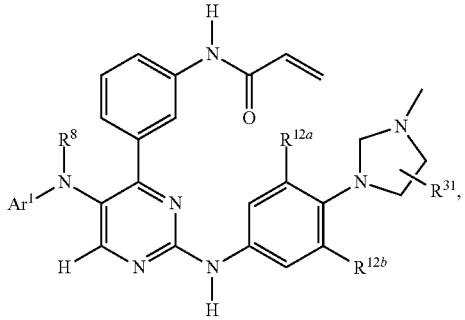

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl; and wherein all variables are as defined herein.

In a further aspect, the compound has a structure represented by a formula:

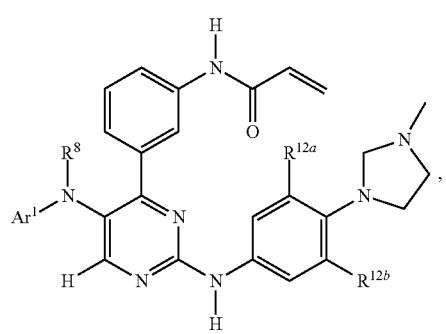

and wherein all variables are as defined herein.

In a further aspect, the compound has a structure represented by a formula:

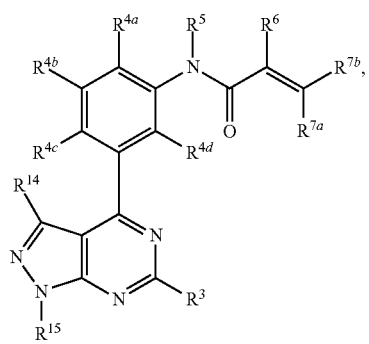

wherein $R^{14}$ is selected from hydrogen and C1-C6 alkyl; wherein $R^{15}$ is selected from hydrogen, C1-C6 alkyl, C1-C6 haloalkyl, and C1-C6 polyhaloalkyl; and wherein all variables are as defined herein.

In a further aspect, the compound has a structure represented by a formula:

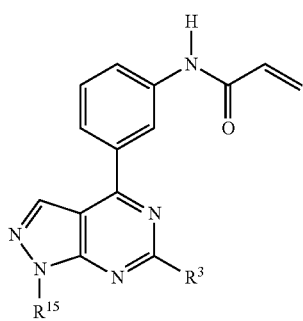
In a further aspect, the compound has a structure represented by a formula:
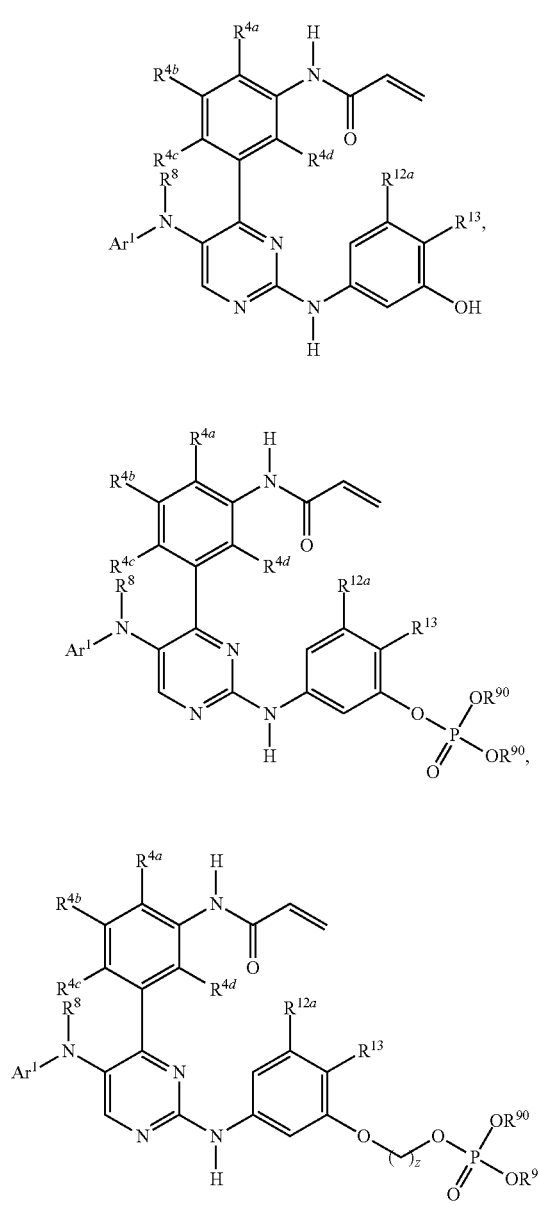
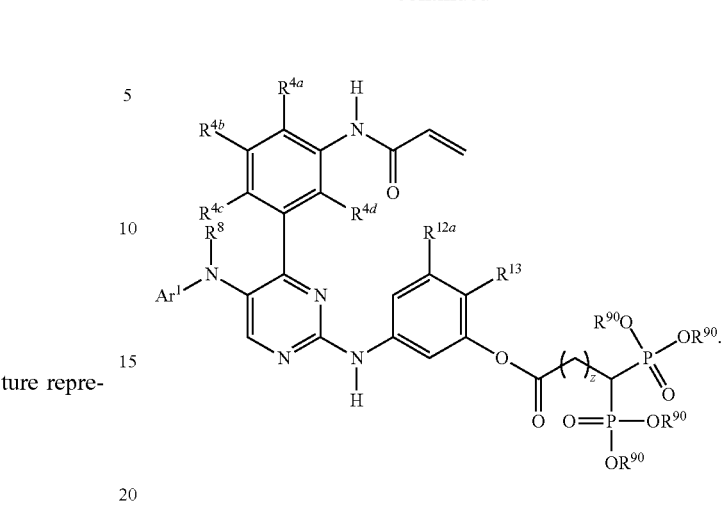
and wherein all variables are as defined herein.
In a further aspect, the compound has a structure represented by a formula:
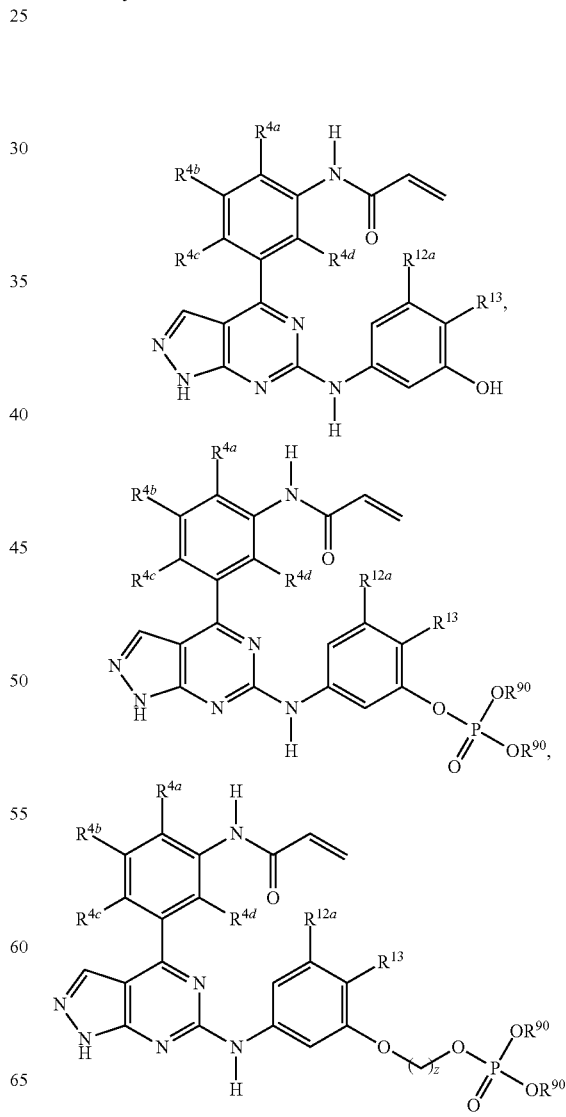

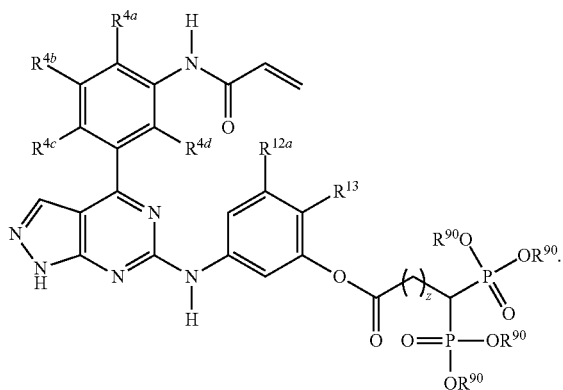
and wherein all variables are as defined herein.
In a further aspect, the compound has a structure represented by a formula:
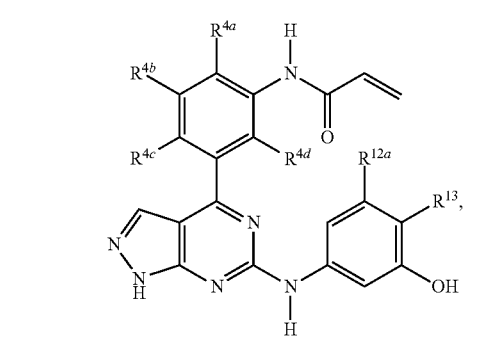
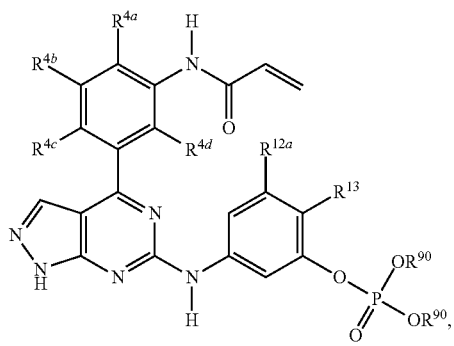
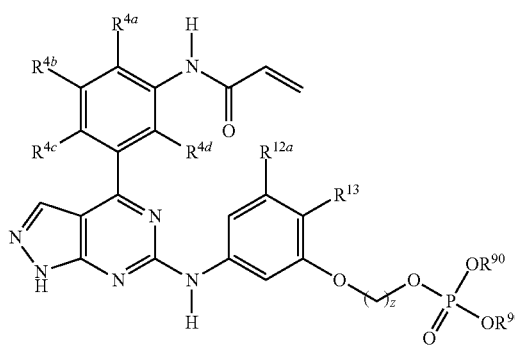
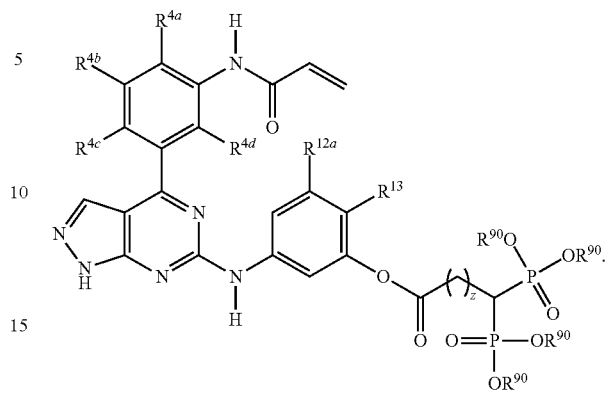
and wherein all variables are as defined herein.
In a further aspect, the compound has a structure represented by a formula:
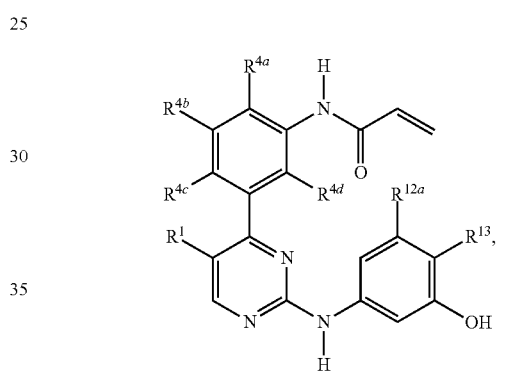
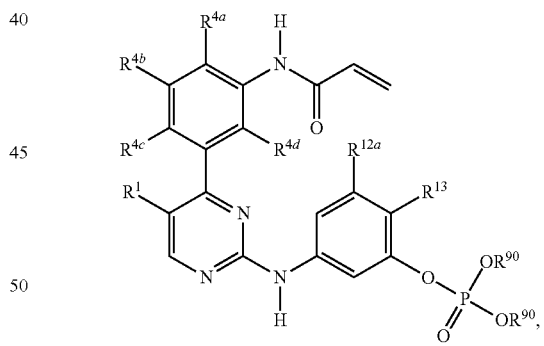
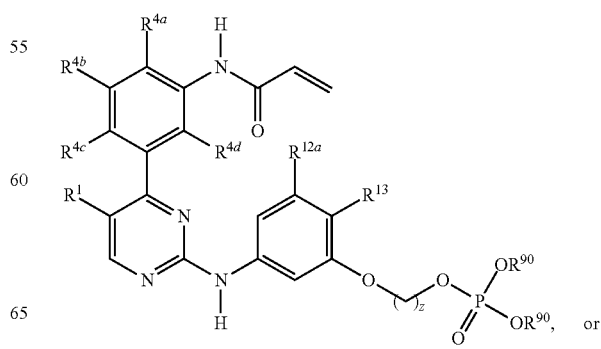

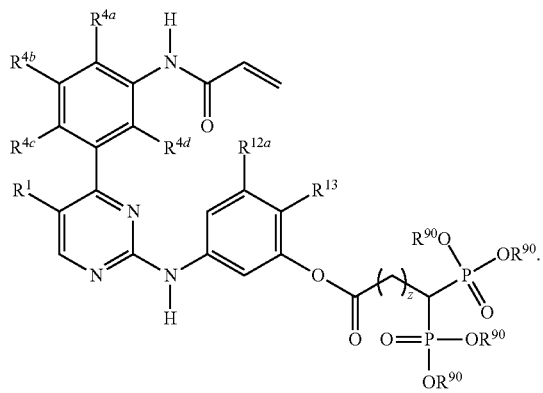
and wherein all variables are as defined herein.
In a further aspect, the compound has a structure represented by a formula:
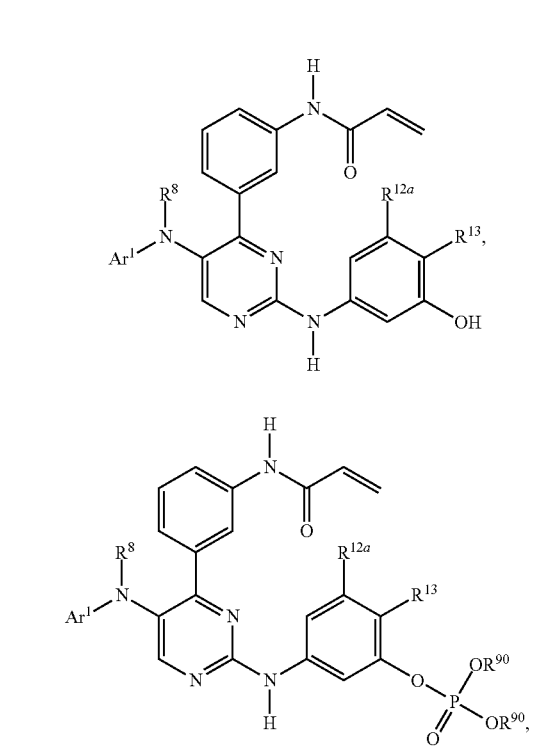
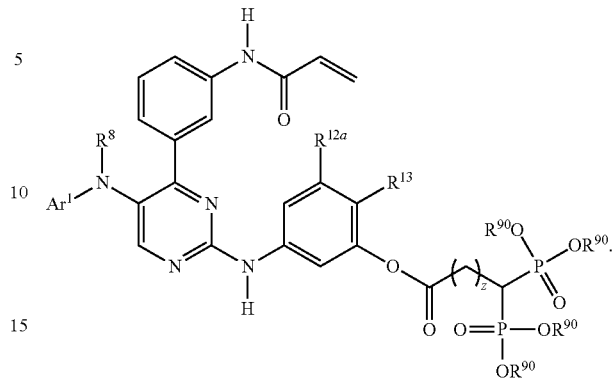
and wherein all variables are as defined herein.
In a further aspect, the compound has a structure represented by a formula:

53
-continued
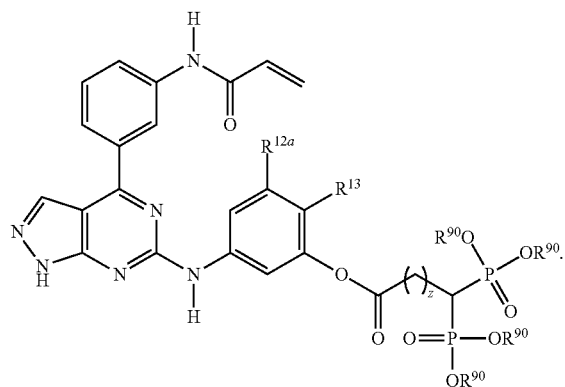
and wherein all variables are as defined herein.
In a further aspect, the compound has a structure represented by a formula:
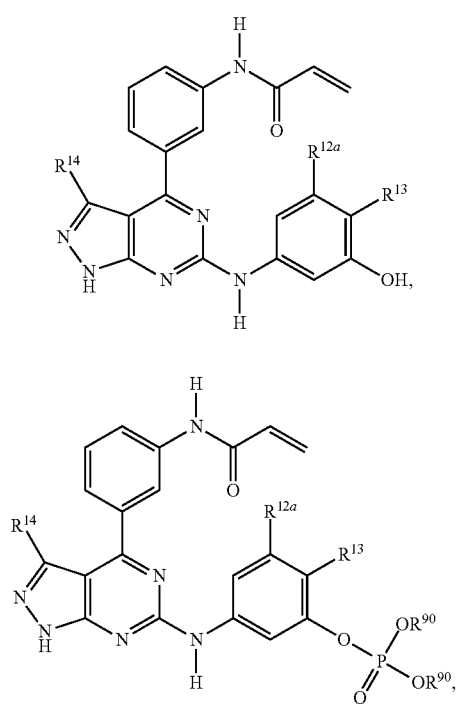
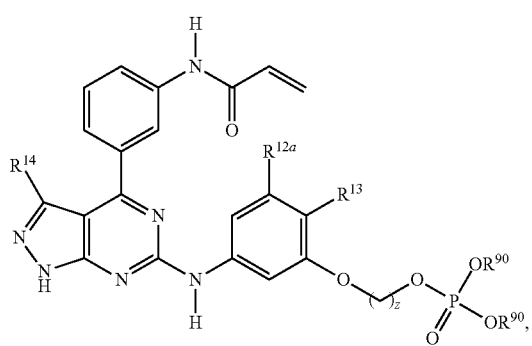
54
-continued
or
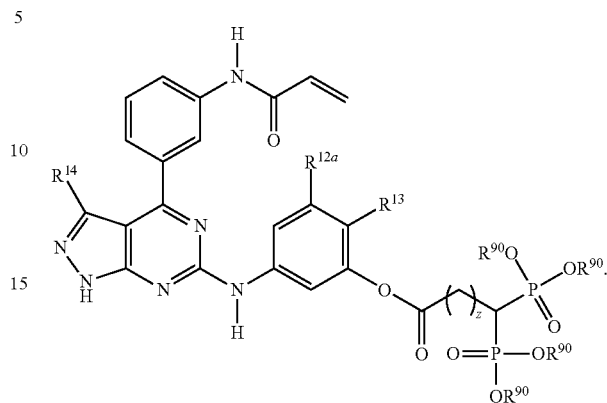
and wherein all variables are as defined herein.
In a further aspect, the compound has a structure represented by a formula:
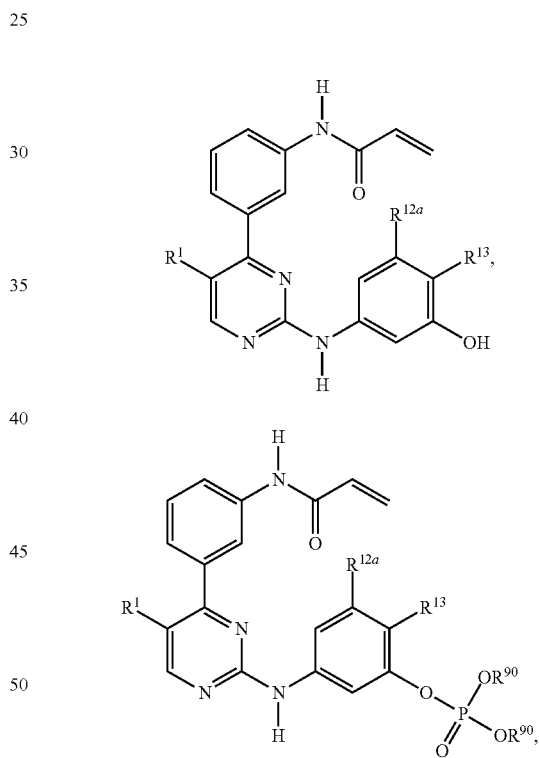
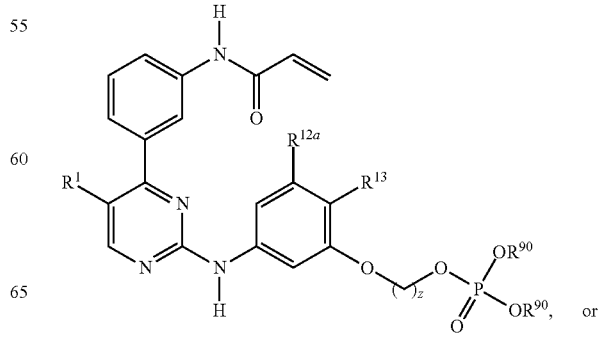
or

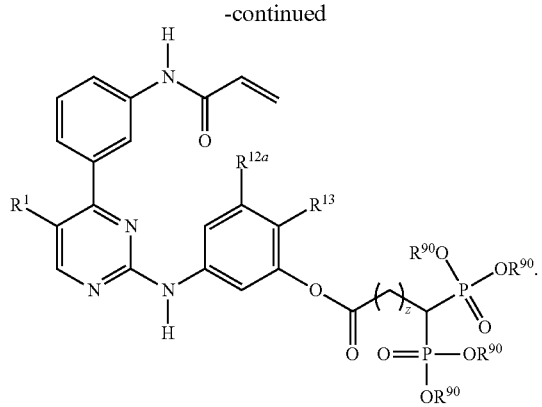
and wherein all variables are as defined herein.
In a further aspect, the compound has a structure represented by a formula:
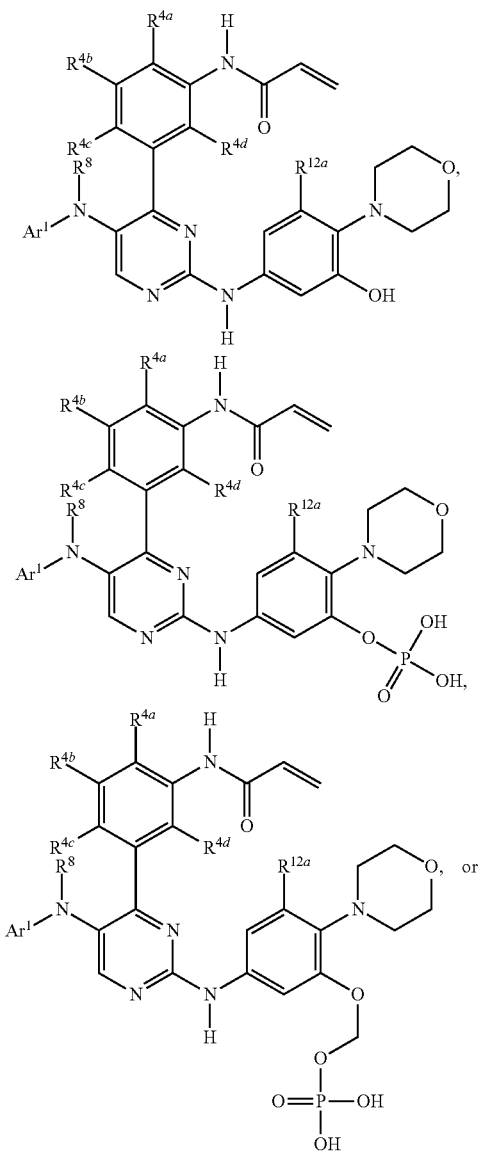
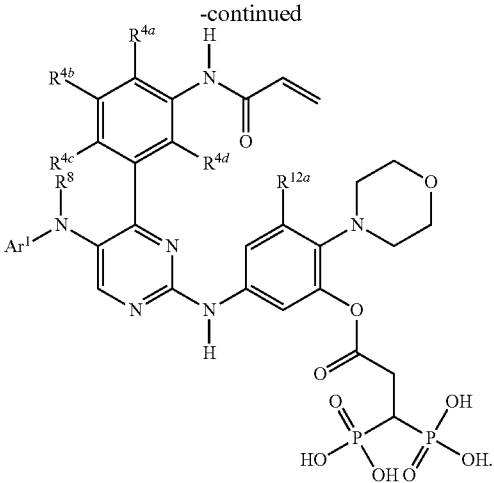
and wherein all variables are as defined herein.
In a further aspect, the compound has a structure represented by a formula:
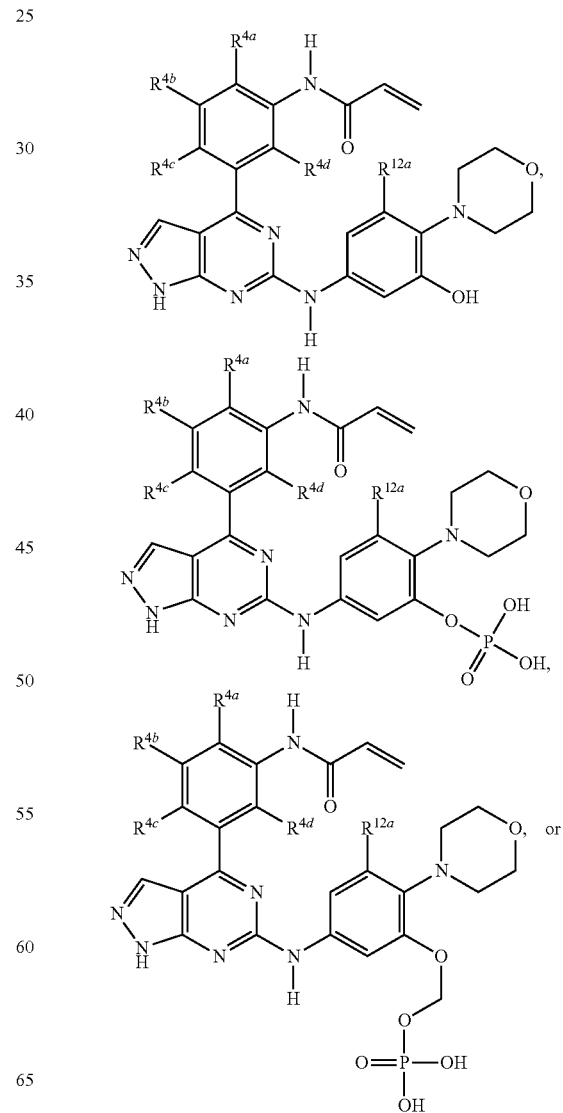

-continued
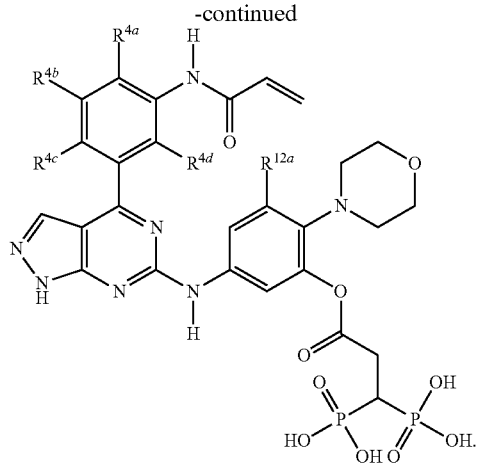
and wherein all variables are as defined herein.
In a further aspect, the compound has a structure represented by a formula:
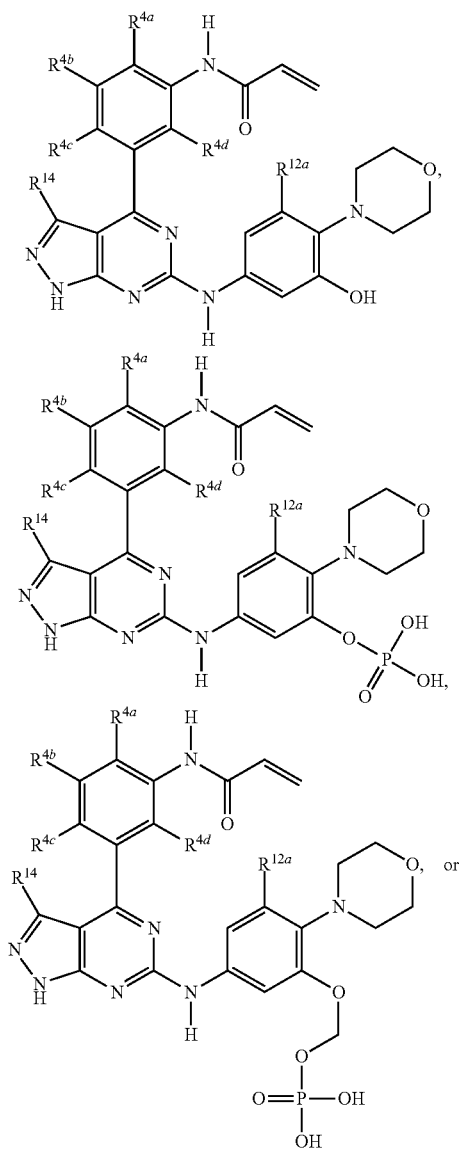
-continued
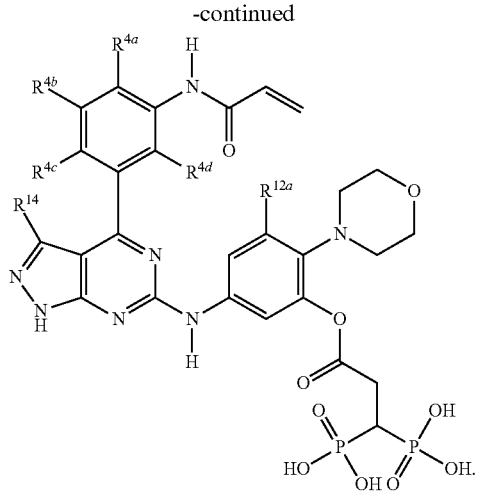
and wherein all variables are as defined herein.
In a further aspect, the compound has a structure represented by a formula:
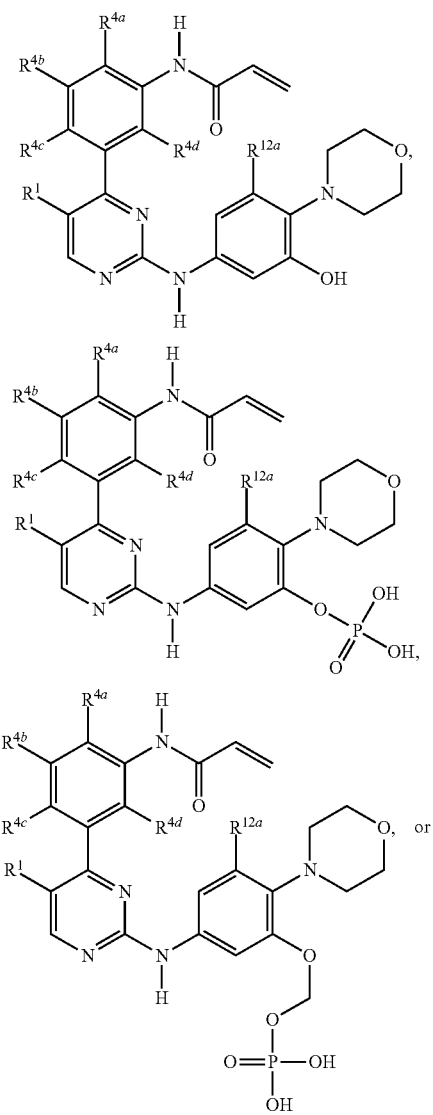

-continued
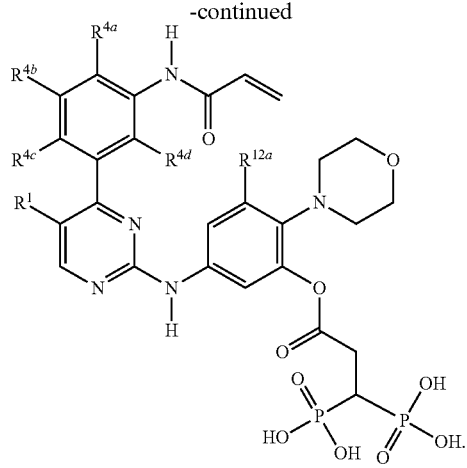
and wherein all variables are as defined herein.
In a further aspect, the compound has a structure represented by a formula:
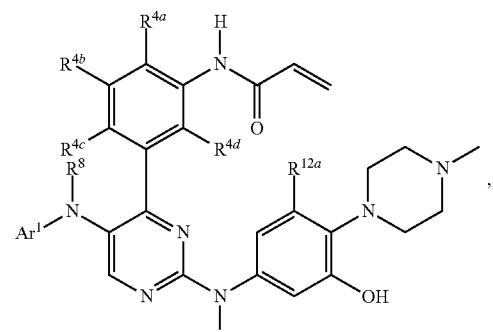
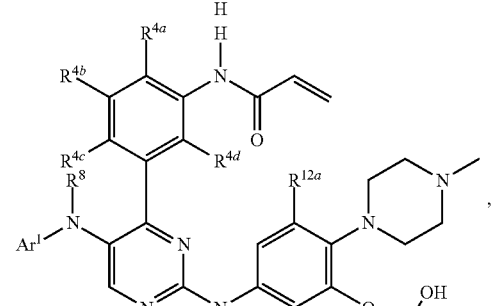
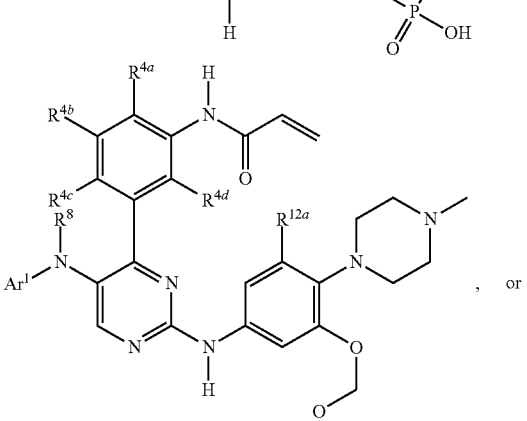
-continued
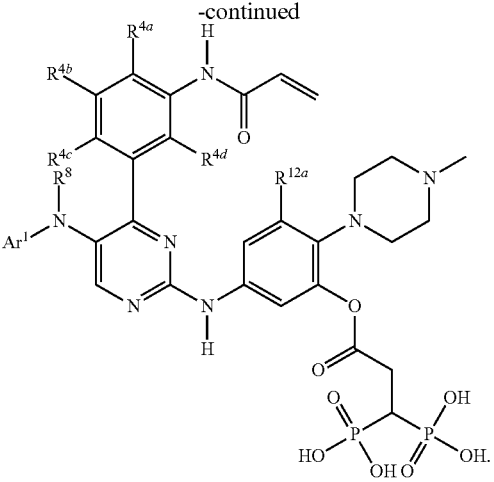
and wherein all variables are as defined herein.
In a further aspect, the compound has a structure represented by a formula:
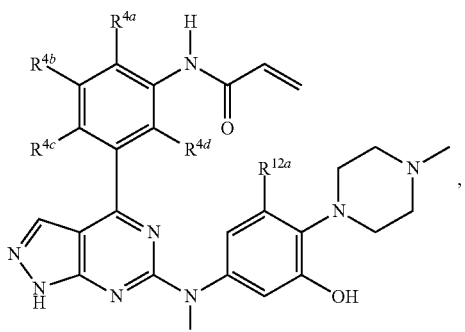
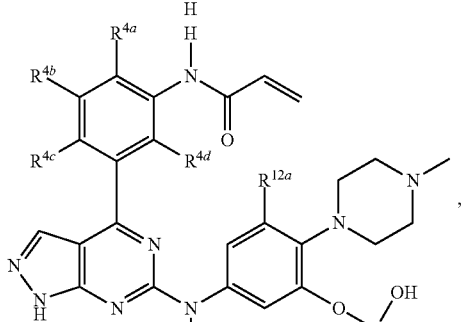
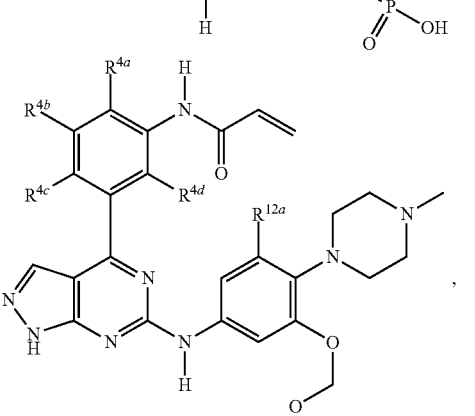
, or -continued
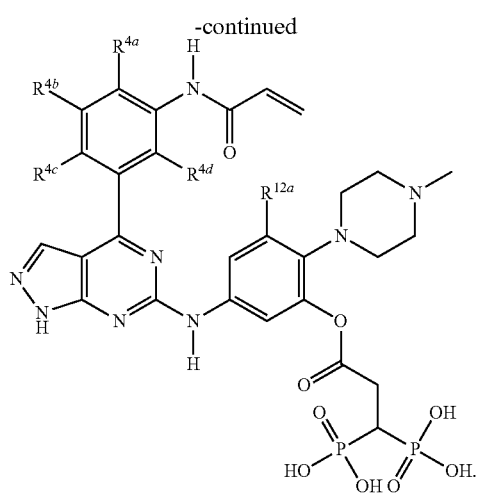
and wherein all variables are as defined herein.
In a further aspect, the compound has a structure represented by a formula:
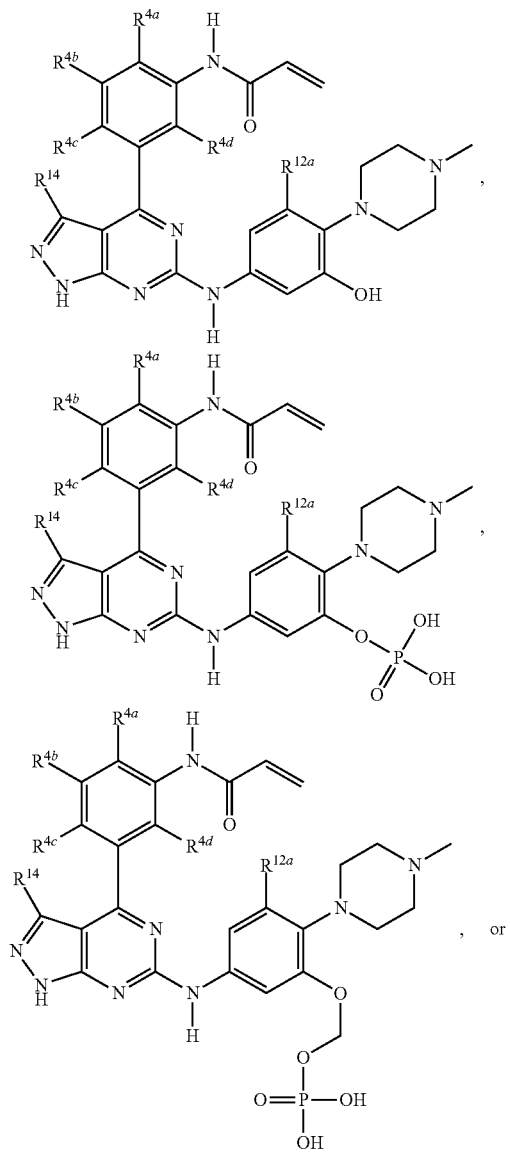
-continued
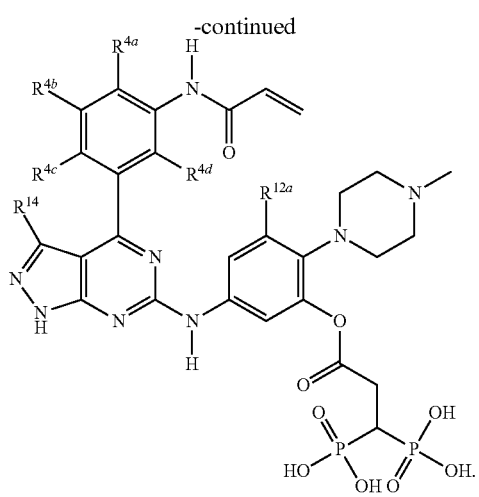
and wherein all variables are as defined herein.
In a further aspect, the compound has a structure represented by a formula:
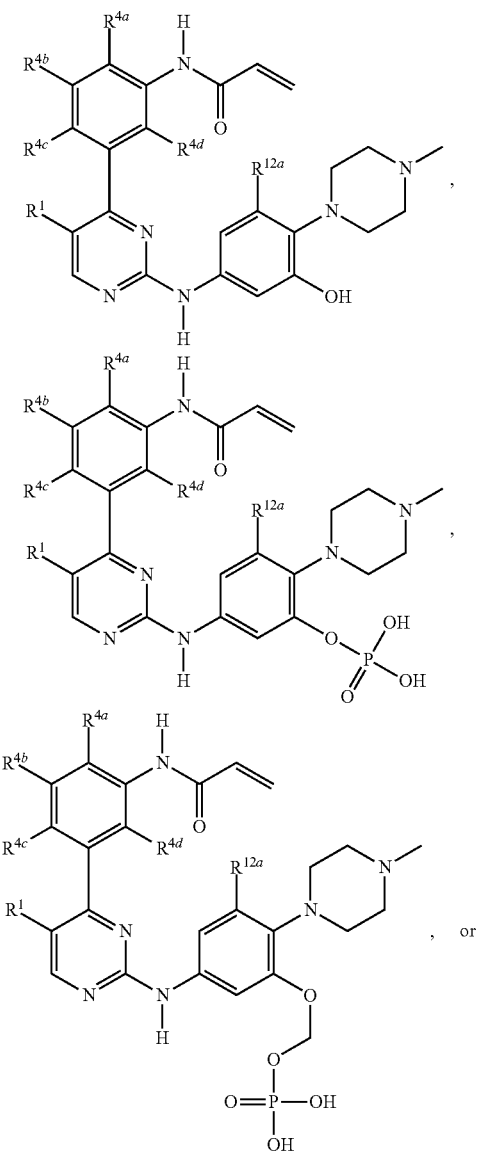
, or -continued

[Chemical structure with substituents $R^{4a}$, $R^{4b}$, $R^{4c}$, $R^{4d}$, $R^1$, $R^{12a}$]

and wherein all variables are as defined herein.

Suitable substituents are described below.

a. $Ar^1$ Groups

In one aspect, $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino.

In a further aspect, $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino. In a further aspect, $Ar^1$ is phenyl substituted with 1-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino. In a further aspect, $Ar^1$ is phenyl substituted with 1-2 groups independently selected from cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is phenyl substituted with a group selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino.

In a further aspect, $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino. In a further aspect, $Ar^1$ is monocyclic heteroaryl substituted with 1-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino. In a further aspect, $Ar^1$ is monocyclic heteroaryl substituted with 1-2 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino. In a further aspect, $Ar^1$ is monocyclic heteroaryl substituted with a group selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino.

In a further aspect, $Ar^1$ is selected from pyridinyl, pyrimidinyl; pyridazinyl, and pyrazinyl; and $Ar^1$ is substituted with 0-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is selected from pyridinyl, pyrimidinyl; pyridazinyl, and pyrazinyl; and $Ar^1$ is substituted with 1-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is selected from pyridinyl, pyrimidinyl; pyridazinyl, and pyrazinyl; and $Ar^1$ is substituted with 1-2 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is selected from pyridinyl, pyrimidinyl; pyridazinyl, and pyrazinyl; and $Ar^1$ is monosubstituted with a group selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino.

In a further aspect, $Ar^1$ is pyridinyl and substituted with 0-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyridinyl and substituted with 1-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyridinyl and substituted with 1-2 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyridinyl monosubstituted with a group selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino.

In a further aspect, $Ar^1$ is pyrimidinyl and substituted with 0-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyrimidinyl and substituted with 1-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyrimidinyl and substituted with 1-2 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyrimidinyl monosubstituted with a group selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino.

In a further aspect, $Ar^1$ is pyridazinyl and substituted with 0-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyridazinyl and substituted with 1-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyridazinyl and substituted with 1-2 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyridazinyl monosubstituted with a group selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino.

In a further aspect, $Ar^1$ is pyrazinyl and substituted with 0-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyrazinyl and substituted with 1-3 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyrazinyl and substituted with 1-2 groups independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino. In a further aspect, $Ar^1$ is pyrazinyl monosubstituted with a group selected from halo, cyano, C1-C6 alkyl, C1-C6 haloalkyoxy, C1-C6 haloalkyl, and C1-C6 polyhaloalkyl, C1-C6 cyanoalkyl, $SO_2R^9$, C1-C3 alkylamine, and C1-C3 dialkylamino.

In a further aspect, $Ar^1$ is phenyl substituted with 0-3 groups independently selected from halo, cyano, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, and —$NHCH(CH_3)_2$. In a still further aspect, $Ar^1$ is phenyl substituted with 0-3 groups independently selected from —F, —Cl, —Br, cyano, methyl, ethyl, propyl, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$N(CH_3)_2$, and —$N(CH_3)CH_2CH_3$. In a yet further aspect, $Ar^1$ is phenyl substituted with 0-3 groups independently selected from —F, —Cl, —Br, cyano, methyl, ethyl, propyl, —$CH_2F$, —$CH_2Cl$, —$CH_2Br$, —$CHF_2$, —$CF_3$, —$CHCl_2$, —$CCl_3$, —$CHBr_2$, —$CBr_3$, —$CI_3$, —$OCH_3$, —$NHCH_3$, and —$N(CH_3)_2$.

In a further aspect, $Ar^1$ is phenyl substituted with 1-3 groups independently selected from halo, cyano, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, and —$NHCH(CH_3)_2$. In a still further aspect, $Ar^1$ is phenyl substituted with 1-3 groups independently selected from —F, —Cl, —Br, cyano, methyl, ethyl, propyl, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$N(CH_3)_2$, and —$N(CH_3)CH_2CH_3$. In a yet further aspect, $Ar^1$ is phenyl substituted with 1-3 groups independently selected from —F, —Cl, —Br, cyano, methyl, ethyl, propyl, —$CH_2F$, —$CH_2Cl$, —$CH_2Br$, —$CHF_2$, —$CF_3$, —$CHCl_2$, —$CCl_3$, —$CHBr_2$, —$CBr_3$, —$CI_3$, —$OCH_3$, —$NHCH_3$, and —$N(CH_3)_2$.

In a further aspect, $Ar^1$ is phenyl substituted with 1-2 groups independently selected from halo, cyano, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$OCH_3$, —$OCH_2CH_3$, —$O(CH_2)_2CH_3$, —$OCH(CH_3)_2$, —$OCH(CH_2CH_3)(CH_3)$, —$NHCH_3$, —$NHCH_2CH_3$, —$NH(CH_2)_2CH_3$, and —$NHCH(CH_3)_2$. In a still further aspect, $Ar^1$ is phenyl substituted with 1-2 groups independently selected from —F, —Cl, —Br, cyano, methyl, ethyl, propyl, —$CH_2F$, —$CH_2Cl$, —$CH_2Br$, —$CH_2CH_2F$, —$CH_2CH_2Cl$, —$CH_2CH_2Br$, —$(CH_2)_2CH_2F$, —$(CH_2)_2CH_2Cl$, —$(CH_2)_2CH_2Br$, —$CHF_2$, —$CF_3$, —$CHCl_2$, —$CCl_3$, —$CHBr_2$, —$CBr_3$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$OCH_3$, —$OCH_2CH_3$, —$O(CH_2)_2CH_3$, —$OCH(CH_3)_2$, —$NHCH_3$, —$NHCH_2CH_3$, —$NH(CH_2)_2CH_3$, —$NHCH(CH_3)_2$, —$N(CH_3)_2$, and —$N(CH_3)CH_2CH_3$. In a yet further aspect, $Ar^1$ is phenyl substituted with 1-2 groups independently selected from —F, —Cl, —Br, cyano, methyl, ethyl, propyl, —$CH_2F$, —$CH_2Cl$, —$CH_2Br$, —$CHF_2$, —$CF_3$, —$CHCl_2$, —$CCl_3$, —$CHBr_2$, —$CBr_3$, —$CI_3$, —$OCH_3$, —$NHCH_3$, and —$N(CH_3)_2$.

In a further aspect, $Ar^1$ is phenyl monosubstituted with a group selected from halo, cyano, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —OCH$_3$, —OCH$_2$CH$_3$, —O(CH$_2$)$_2$CH$_3$, —OCH(CH$_3$)$_2$, —OCH(CH$_2$CH$_3$)(CH$_3$), —NHCH$_3$, —NHCH$_2$CH$_3$, —NH(CH$_2$)$_2$CH$_3$, and —NHCH(CH$_3$)$_2$. In a still further aspect, Ar$^1$ is phenyl monosubstituted with a group selected from —F, —Cl, —Br, cyano, methyl, ethyl, propyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —OCH$_3$, —OCH$_2$CH$_3$, —O(CH$_2$)$_2$H$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, and —N(CH$_3$)CH$_2$CH$_3$. In a yet further aspect, Ar$^1$ is phenyl monosubstituted with a group selected from —F, —Cl, —Br, cyano, methyl, ethyl, propyl, —CH$_2$F, —CH$_2$Cl, —CH$_2$Br, —CHF$_2$, —CF$_3$, —CHCl$_2$, —CCl$_3$, —CHBr$_2$, —CBr$_3$, —OCH$_3$, —NHCH$_3$, and —N(CH$_3$)$_2$.

In a further aspect, Ar$^1$ is phenyl monosubstituted with a group selected from —F, —Cl, and —Br. In a still further aspect, Ar$^1$ is phenyl monosubstituted with a group selected from methyl, —CH$_2$F, —CH$_2$Cl, —CH$_2$Br, —CHF$_2$, —CF$_3$, —CHCl$_2$, —CCl$_3$, —CHBr$_2$, and —CBr$_3$. In a still further aspect, Ar$^1$ is phenyl monosubstituted with a group selected from —OCH$_3$, —NHCH$_3$, and —N(CH$_3$)$_2$. In an even further aspect, Ar$^1$ is phenyl monosubstituted with a group selected from methyl, —CH$_2$F, —CH$_2$Cl, —CHF$_2$, —CF$_3$, —CHCl$_2$, and —CCl$_3$. In a still further aspect, Ar$^1$ is phenyl monosubstituted with a group selected from methyl, —CH$_2$F, —CHF$_2$, and —CF$_3$.

In a further aspect, Ar$^1$ is phenyl substituted with 0-3 groups independently selected from —F, —Cl, and —Br. In a still further aspect, Ar$^1$ is phenyl substituted with 1-3 groups independently selected from —F, —Cl, and —Br. In a yet further aspect, Ar$^1$ is phenyl substituted with 1-2 groups independently selected from —F, —Cl, and —Br.

In a further aspect, Ar$^1$ is phenyl substituted with 0-3 —F groups. In a still further aspect, Ar$^1$ is phenyl substituted with 1-3 —F groups. In a yet further aspect, Ar$^1$ is phenyl substituted with 1-2 —F groups. In an even further aspect, Ar$^1$ is phenyl monosubstituted with a —F group.

b. R$^1$ Groups

In one aspect, R$^1$ is halogen, NR$^8$Ar$^1$, or R$^1$ and R$^2$ are covalently bonded and, together with the intermediate carbons, comprise an optionally substituted fused five-membered or six-membered C2-C5 heterocyclic ring. In a further aspect, R$^1$ is NR$^8$Ar$^1$, or R$^1$ and R$^2$ are covalently bonded and, together with the intermediate carbons, comprise an optionally substituted fused five-membered or six-membered C2-C5 heterocyclic ring.

In a further aspect, R$^1$ is NR$^8$Ar$^1$.

In a further aspect, R$^1$ is halogen. In a still further aspect, R$^1$ is selected from —F, —Cl, and —Br. In a yet further aspect, R$^1$ is selected from —F and —Cl. In an even further aspect, R$^1$ is selected from —F and —Br. In a still further aspect, R$^1$ is selected from —Cl and —Br. In a yet further aspect, R$^1$ is —F. In an even further aspect, R$^1$ is —Cl. In a still further aspect, R$^1$ is —Br.

In a further aspect, R$^1$ and R$^2$ are covalently bonded and, together with the intermediate carbons, comprise an optionally substituted fused five-membered or six-membered C2-C5 heterocyclic ring.

In a further aspect, the heterocyclic ring is a five-membered ring. In a further aspect, the heterocyclic ring is a six-membered ring. In a further aspect, the heterocyclic ring is a C2-C4 ring. In a further aspect, the heterocyclic ring is a C3-05 ring. In a further aspect, the heterocyclic ring is a C3-C4 ring. In a further aspect, the heterocyclic ring is an optionally substituted pyrazole ring. In a further aspect, the heterocyclic ring is an optionally substituted pyrrole ring.

In a further aspect, the heterocyclic ring is an optionally substituted ring selected from a triazoline ring, furan ring, pyrrole ring, imidazole ring, pyrazole ring, triazole ring, isoxazole ring, oxazole ring, and thiophene ring. In a still further aspect, the heterocyclic ring is an optionally substituted pyrrazole ring. In a yet further aspect, the heterocyclic ring is an optionally substituted pyrrole ring.

In a further aspect, R$^1$ and R$^2$ are covalently bonded and, together with the intermediate carbons, comprise a ring with structure represented by the formula:

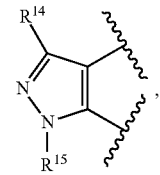

R$^{14}$ is selected from hydrogen and C1-C6 alkyl; and R$^{15}$ is selected from hydrogen, C1-C6 alkyl, C1-C6 haloalkyl, and C1-C6 polyhaloalkyl.

In a further aspect, R$^1$ and R$^2$ are covalently bonded and, together with the intermediate carbons, comprise a ring with structure represented by the formula:

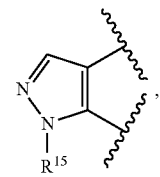

and R$^{15}$ is selected from hydrogen, C1-C6 alkyl, C1-C6 haloalkyl, and C1-C6 polyhaloalkyl.

In a further aspect, R$^1$ and R$^2$ are covalently bonded and, together with the intermediate carbons, comprise a ring with structure represented by the formula:

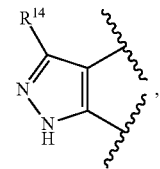

and R$^{14}$ is selected from hydrogen and C1-C6 alkyl.

In a further aspect, c. R$^2$ Groups

In one aspect, R$^2$ is hydrogen, or R$^1$ and R$^2$ are covalently bonded and, together with the intermediate carbons, comprise an optionally substituted fused five-membered or six-membered C2-C5 heterocyclic ring. In a further aspect, R$^2$ is hydrogen.

d. R³ Groups

In one aspect, R³ is a group having a structure represented by the formula:

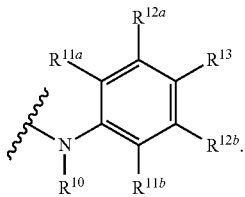

In a further aspect, R³ is a group having a structure represented by the formula:

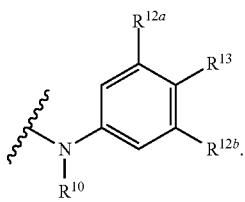

In a further aspect, R³ is a group having a structure represented by the formula:

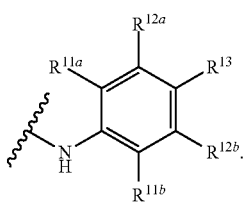

In a further aspect, R³ is a group having a structure represented by the formula:

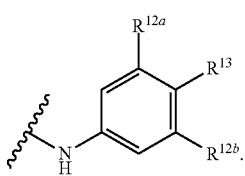

In a further aspect, R³ is a group having a structure represented by the formula:

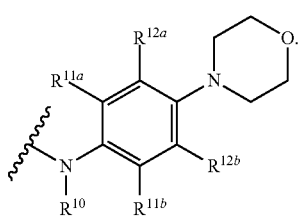

In a further aspect, R³ is a group having a structure represented by the formula:

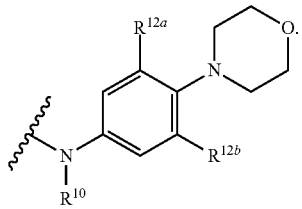

In a further aspect, R³ is a group having a structure represented by the formula:

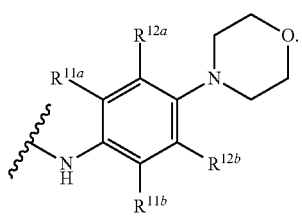

In a further aspect, R³ is a group having a structure represented by the formula:

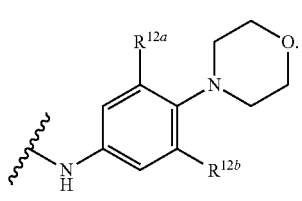

In a further aspect, R³ is a group having a structure represented by the formula:

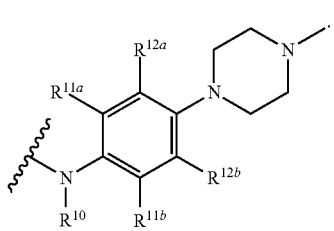

In a further aspect, R³ is a group having a structure represented by the formula:

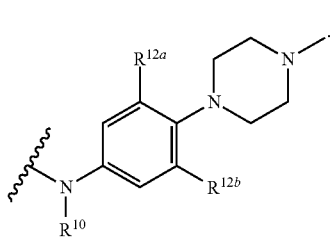

In a further aspect, R³ is a group having a structure represented by the formula:

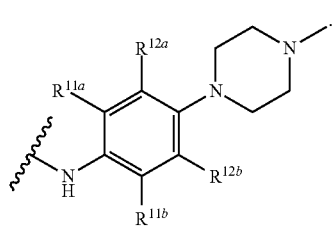

In a further aspect, R³ is a group having a structure represented by the formula:

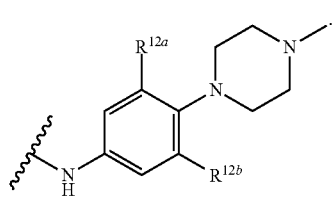

In a further aspect, R³ is a group having a structure represented by the formula:

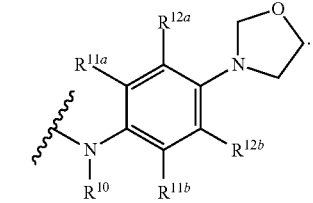

In a further aspect, R³ is a group having a structure represented by the formula:

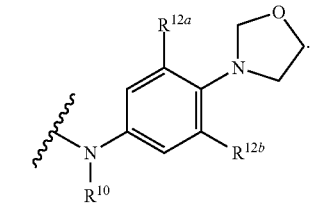

In a further aspect, R³ is a group having a structure represented by the formula:

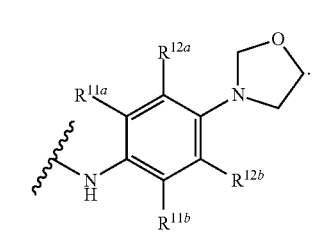

In a further aspect, R³ is a group having a structure represented by the formula:

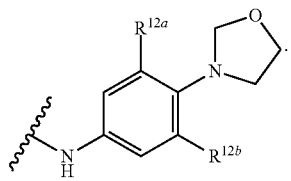

In a further aspect, R³ is a group having a structure represented by the formula:

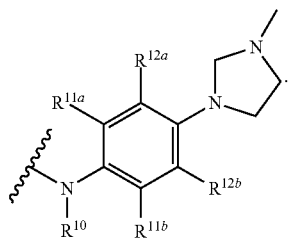

In a further aspect, R³ is a group having a structure represented by the formula:

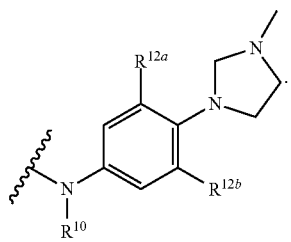

In a further aspect, R³ is a group having a structure represented by the formula:

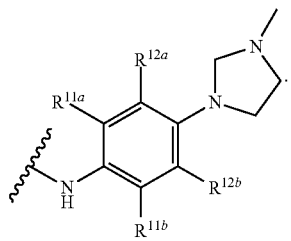

In a further aspect, R³ is a group having a structure represented by the formula:

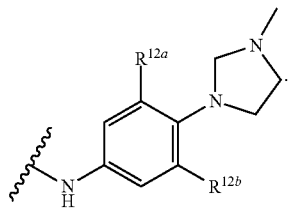

In a further aspect, R³ is a group having a structure represented by the formula:

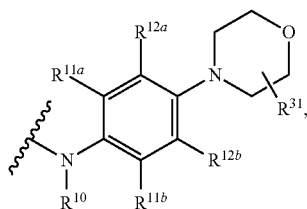

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

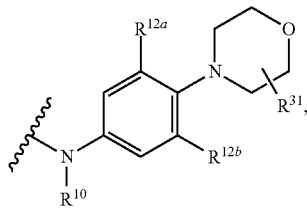

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

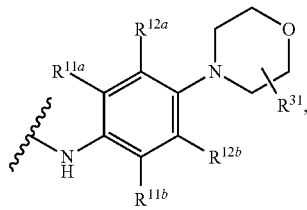

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

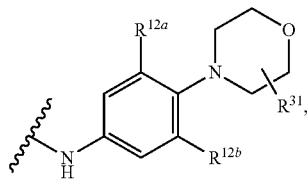

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

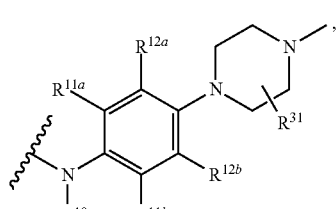

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

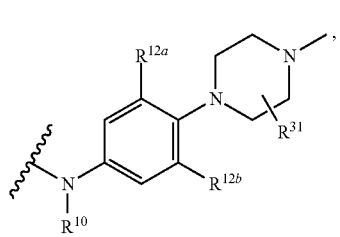

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

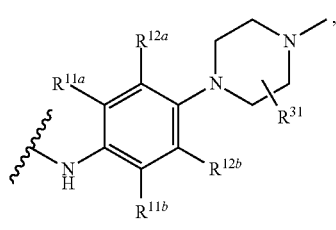

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

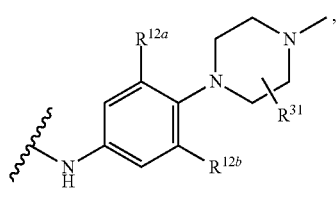

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

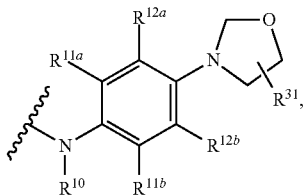

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

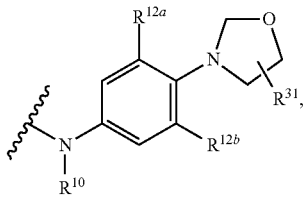

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

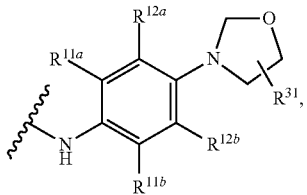

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

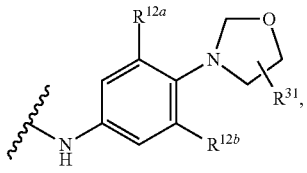

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

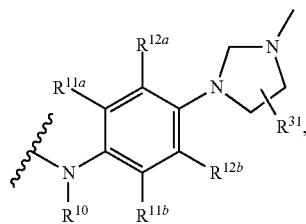

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

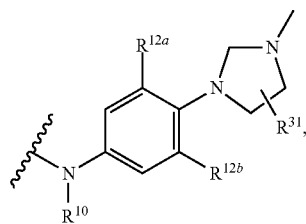

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

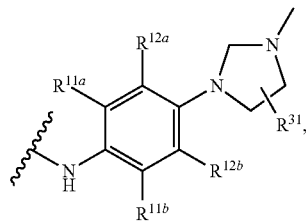

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

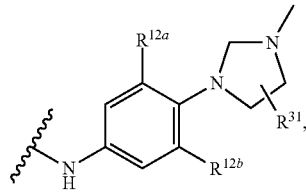

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

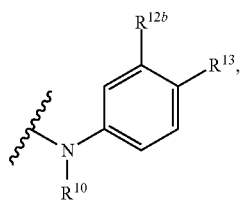

In a further aspect, R³ is a group having a structure represented by the formula:

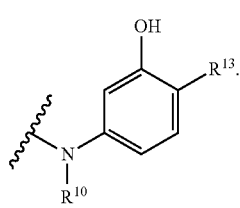

In a further aspect, R³ is a group having a structure represented by the formula:

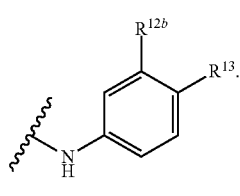

In a further aspect, R³ is a group having a structure represented by the formula:

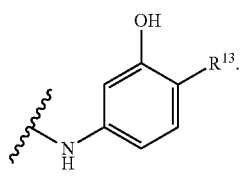

In a further aspect, R³ is a group having a structure represented by the formula:

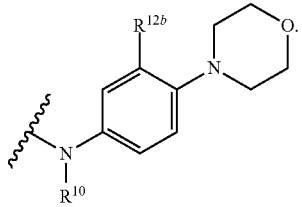

In a further aspect, R³ is a group having a structure represented by the formula:

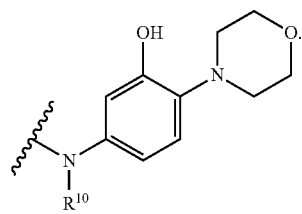

In a further aspect, R³ is a group having a structure represented by the formula:

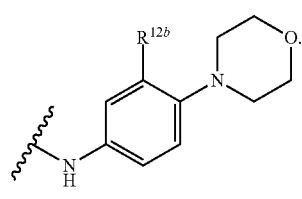

In a further aspect, R³ is a group having a structure represented by the formula:

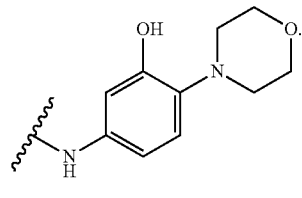 [SMILES: *Nc1ccc(N2CCOCC2)c(O)c1]

In a further aspect, R³ is a group having a structure represented by the formula:

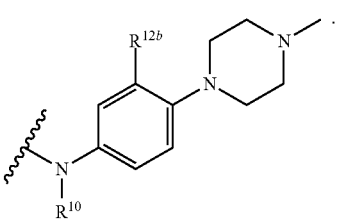

In a further aspect, R³ is a group having a structure represented by the formula:

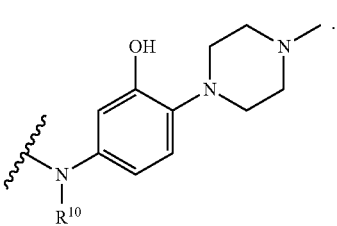

In a further aspect, R³ is a group having a structure represented by the formula:

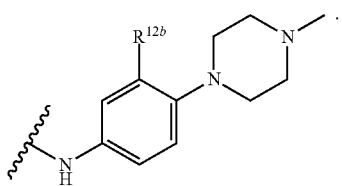

In a further aspect, R³ is a group having a structure represented by the formula:

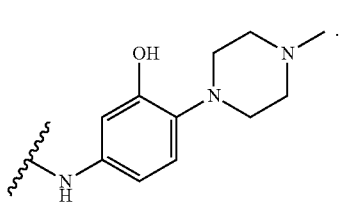 [SMILES: *Nc1ccc(N2CCN(C)CC2)c(O)c1]

In a further aspect, R³ is a group having a structure represented by the formula:

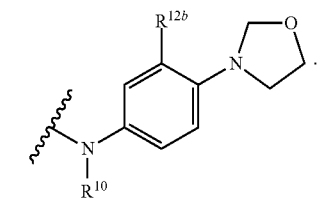

In a further aspect, R³ is a group having a structure represented by the formula:

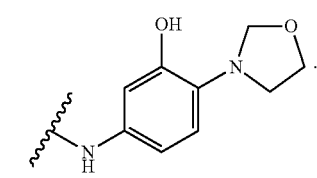 [SMILES: *Nc1ccc(N2CCOC2)c(O)c1]

In a further aspect, R³ is a group having a structure represented by the formula:

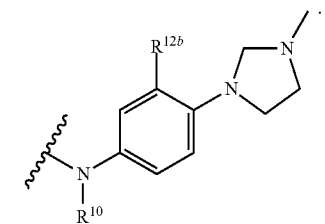

In a further aspect, R³ is a group having a structure represented by the formula:

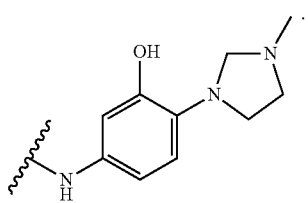 [SMILES: *Nc1ccc(N2CCN(C)C2)c(O)c1]

In a further aspect, R³ is a group having a structure represented by the formula:

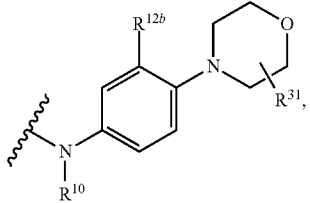

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, R³ is a group having a structure represented by the formula:

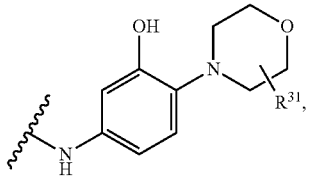

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, R³ is a group having a structure represented by the formula:

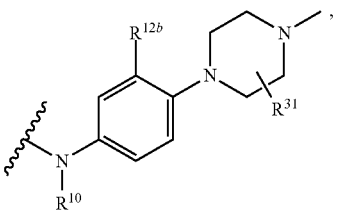

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, R³ is a group having a structure represented by the formula:

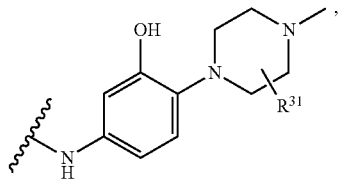

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen.

In a further aspect, $R^3$ is a group having a structure represented by the formula:

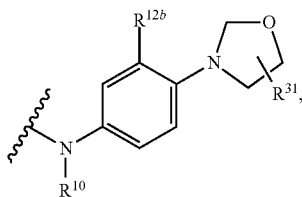

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

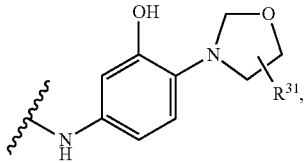

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

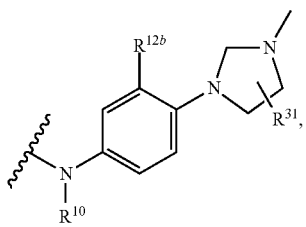

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

In a further aspect, $R^3$ is a group having a structure represented by the formula:

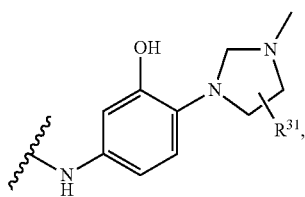

wherein each occurrence of $R^{31}$ is selected from hydrogen, halogen, cyano, C1-C6 alkyl, C1-C6 haloalkyoxy, C1-C6 haloalkyl, and C1-C6 polyhaloalkyl.

e. $R^4$ Groups

In one aspect, each $R^4$ group (i.e., any of $R^{4a}$, $R^{4b}$, $R^{4c}$, and $R^{4d}$) is independently selected from hydrogen, halogen, and C1-C6 alkyl, for example, C1-C4 alkyl. In a further aspect, $R^{4a}$ is hydrogen. In a further aspect, $R^{4a}$ is halogen or C1-C6 alkyl. In a further aspect, $R^{4b}$ is hydrogen. In a further aspect, $R^{4b}$ is halogen or C1-C6 alkyl. In a further aspect, $R^{4c}$ is hydrogen. In a further aspect, $R^{4c}$ is halogen or C1-C6 alkyl. In a further aspect, $R^{4d}$ is hydrogen. In a further aspect, $R^{4d}$ is halogen or C1-C6 alkyl.

In a further aspect, $R^{4a}$, $R^{4c}$, and $R^{4d}$ are hydrogen. In a still further aspect, $R^{4a}$, $R^{4b}$, $R^{4c}$, and $R^{4d}$ are hydrogen. In a yet further aspect, $R^{4a}$ and $R^{4b}$ are hydrogen. In a still further aspect, $R^{4a}$ and $R^{4c}$ are hydrogen. In an even further aspect, $R^{4a}$ and $R^{4d}$ are hydrogen.

In a still further aspect, $R^{4a}$, $R^{4b}$, and $R^{4d}$ are hydrogen. In a yet further aspect, $R^{4a}$, $R^{4c}$, and $R^{4d}$ are hydrogen. In an even further aspect, $R^{4b}$, $R^{4c}$, and $R^{4d}$ are hydrogen.

In a further aspect, each of $R^{4a}$, $R^{4b}$, $R^{4c}$, and $R^{4d}$, when present is independently selected from hydrogen, halogen methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, each of $R^{4a}$, $R^{4b}$, $R^{4c}$, and $R^{4d}$, when present is independently selected from hydrogen, —F, —Cl, methyl, ethyl, propyl, isopropyl, tert-butyl, sec-butyl, isobutyl, and tert-butyl. In a yet further aspect, each of $R^{4a}$, $R^{4b}$, $R^{4c}$, and $R^{4d}$, when present is independently selected from hydrogen, —F, —Cl, methyl, ethyl, propyl, and isopropyl. In an even further aspect, each of $R^{4a}$, $R^{4b}$, $R^{4c}$, and $R^{4d}$, when present is independently selected from hydrogen, —F, and methyl.

In a further aspect, each of $R^{4a}$, $R^{4b}$, $R^{4c}$, and $R^{4d}$, when present is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, each of $R^{4a}$, $R^{4b}$, $R^{4c}$, and $R^{4d}$, when present is independently selected from hydrogen, methyl, ethyl, propyl, isopropyl, tert-butyl, sec-butyl, isobutyl, and tert-butyl. In a yet further aspect, each of $R^{4a}$, $R^{4b}$, $R^{4c}$, and $R^{4d}$, when present is independently selected from hydrogen, methyl, ethyl, propyl, and isopropyl. In an even further aspect, each of $R^{4a}$, $R^{4b}$, $R^{4c}$, and $R^{4d}$, when present is independently selected from hydrogen and methyl.

In a further aspect, each of $R^{4a}$, $R^{4b}$, $R^{4c}$, and $R^{4d}$, when present is independently selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, each of $R^{4a}$, $R^{4b}$, $R^{4c}$, and $R^{4d}$, when present is independently selected from methyl, ethyl, propyl, isopropyl, tert-butyl, sec-butyl, isobutyl, and tert-butyl. In a yet further aspect, each of $R^{4a}$, $R^{4b}$, $R^{4c}$, and $R^{4d}$, when present is independently selected from methyl, ethyl, propyl, and isopropyl. In an even further aspect, each of $R^{4a}$, $R^{4b}$, $R^{4c}$, and $R^{4d}$, when present is methyl.

In a further aspect, each of $R^{4a}$, $R^{4b}$, $R^{4c}$, and $R^{4d}$, when present is independently selected from hydrogen and halogen. In a still further aspect, each of $R^{4a}$, $R^{4b}$, $R^{4c}$, and $R^{4d}$, when present is independently selected from hydrogen, —F, —Cl, and —Br. In a yet further aspect, each of $R^{4a}$, $R^{4b}$, $R^{4c}$, and $R^{4d}$, when present is independently selected from hydrogen, —F, and —Cl. In an even further aspect, each of $R^{4a}$, $R^{4b}$, $R^{4c}$, and $R^{4d}$, when present is independently selected from hydrogen and —F. In a still further aspect, each of $R^{4a}$, $R^{4b}$, $R^{4c}$, and $R^{4d}$, when present is independently selected from hydrogen and —Cl.

f. $R^5$ Groups

In one aspect, $R^5$ is selected from hydrogen and C1-C6 alkyl. In a further aspect, $R^5$ is hydrogen. In a further aspect, $R^5$ is C1-C6 alkyl, for example, C1-C4 alkyl.

In a further aspect, $R^5$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^5$ is selected from hydrogen, methyl, ethyl, propyl, isopropyl, tert-butyl, sec-butyl, isobutyl, and tert-butyl. In a yet further aspect, $R^5$ is selected from hydrogen, methyl, ethyl, propyl, and isopropyl. In an even further aspect, $R^5$ is selected from hydrogen and methyl.

In a further aspect, $R^5$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^5$ is selected from methyl, ethyl, propyl, isopropyl, tert-butyl, sec-butyl, isobutyl, and tert-butyl. In a yet further aspect, $R^5$ is selected from methyl, ethyl, propyl, and isopropyl. In an even further aspect, $R^5$ is methyl.

g. $R^6$ Groups

In one aspect, $R^6$ is selected from hydrogen and C1-C6 alkyl. In a further aspect, $R^6$ is hydrogen. In a further aspect, $R^6$ is C1-C6 alkyl, for example, C1-C4 alkyl.

In a further aspect, $R^6$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^6$ is selected from hydrogen, methyl, ethyl, propyl, isopropyl, tert-butyl, sec-butyl, isobutyl, and tert-butyl. In a yet further aspect, $R^6$ is selected from hydrogen, methyl, ethyl, propyl, and isopropyl. In an even further aspect, $R^6$ is selected from hydrogen and methyl.

In a further aspect, $R^6$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^6$ is selected from methyl, ethyl, propyl, isopropyl, tert-butyl, sec-butyl, isobutyl, and tert-butyl. In a yet further aspect, $R^6$ is selected from methyl, ethyl, propyl, and isopropyl. In an even further aspect, $R^6$ is methyl.

h. $R^7$ Groups

In one aspect, each $R^7$ group (i.e., either of $R^{7a}$ and $R^{7b}$) is independently selected from hydrogen, halogen, and C1-C6 alkyl, for example, C1-C4 alkyl. In a further aspect, $R^{7a}$ is hydrogen. In a further aspect, $R^{7a}$ is C1-C6 alkyl. In a further aspect, $R^{7b}$ is hydrogen. In a further aspect, $R^{7b}$ is C1-C6 alkyl. In a further aspect, $R^6$, $R^{7a}$, and $R^{7b}$ are all hydrogen.

In a further aspect, each of $R^{7a}$ and $R^{7a}$ is independently selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, each of $R^{7a}$ and $R^{7a}$ is independently from hydrogen, methyl, ethyl, propyl, isopropyl, ten-butyl, sec-butyl, isobutyl, and tert-butyl. In a yet further aspect, each of $R^{7a}$ and $R^{7a}$ is independently from hydrogen, methyl, ethyl, propyl, and isopropyl. In an even further aspect, each of $R^{7a}$ and $R^{7a}$ is independently from hydrogen and methyl.

In a further aspect, each of $R^{7a}$ and $R^{7a}$ is independently from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, each of $R^{7a}$ and $R^{7a}$ is independently from methyl, ethyl, propyl, isopropyl, tert-butyl, sec-butyl, isobutyl, and tert-butyl. In a yet further aspect, each of $R^{7a}$ and $R^{7a}$ is independently from methyl, ethyl, propyl, and isopropyl. In an even further aspect, each of $R^{7a}$ and $R^{7a}$ is methyl.

In a further aspect, $R^{7a}$ is hydrogen and $R^{7a}$ is selected from hydrogen, methyl, ethyl, propyl, isopropyl, tert-butyl, sec-butyl, isobutyl, neopentyl, isopentyl, sec-pentyl, ten-pentyl, 3,3-dimethylbutan-2-yl, 2,3-dimethylbutan-2-yl. In a still further aspect, $R^{7a}$ is hydrogen and $R^{7a}$ is selected from hydrogen, methyl, ethyl, propyl, isopropyl, tert-butyl, sec-butyl, isobutyl, and tert-butyl. In a yet further aspect, $R^{7a}$ is hydrogen and $R^{7a}$ is selected from hydrogen, methyl, ethyl, propyl, and isopropyl. In an even further aspect, $R^{7a}$ is hydrogen and $R^{7a}$ is selected from hydrogen and methyl.

In a further aspect, $R^{7a}$ is hydrogen and $R^{7a}$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^{7a}$ is hydrogen and $R^{7a}$ is selected from methyl, ethyl, propyl, isopropyl, tert-butyl, sec-butyl, isobutyl, and tert-butyl. In a yet further aspect, $R^{7a}$ is hydrogen and $R^{7a}$ is selected from methyl, ethyl, propyl, and isopropyl. In an even further aspect, $R^{7a}$ is hydrogen and $R^{7a}$ is methyl.

In a further aspect, $R^{7b}$ is hydrogen and $R^{7a}$ is selected from hydrogen, methyl, ethyl, propyl, isopropyl, tert-butyl, sec-butyl, isobutyl, neopentyl, isopentyl, sec-pentyl, ten-pentyl, 3,3-dimethylbutan-2-yl, 2,3-dimethylbutan-2-yl. In a still further aspect, $R^{7b}$ is hydrogen and $R^{7a}$ is selected from hydrogen, methyl, ethyl, propyl, isopropyl, tert-butyl, sec-butyl, isobutyl, and tert-butyl. In a yet further aspect, $R^{7b}$ is hydrogen and $R^{7a}$ is selected from hydrogen, methyl, ethyl, propyl, and isopropyl. In an even further aspect, $R^{7b}$ is hydrogen and $R^{7a}$ is selected from hydrogen and methyl.

In a further aspect, $R^{7b}$ is hydrogen and $R^{7a}$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^{7b}$ is hydrogen and $R^{7a}$ is selected from methyl, ethyl, propyl, isopropyl, tert-butyl, sec-butyl, isobutyl, and tert-butyl. In a yet further aspect, $R^{7b}$ is hydrogen and $R^{7a}$ is selected from methyl, ethyl, propyl, and isopropyl. In an even further aspect, $R^{7b}$ is hydrogen and $R^{7a}$ is methyl.

i. $R^8$ Groups

In one aspect, $R^8$ is selected from hydrogen and C1-C6 alkyl. In a further aspect, $R^8$ is hydrogen. In a further aspect, $R^8$ is C1-C6 alkyl, for example, C1-C4 alkyl.

In a further aspect, $R^8$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^8$ is selected from hydrogen, methyl, ethyl, propyl, isopropyl, tert-butyl, sec-butyl, isobutyl, and tert-butyl. In a yet further aspect, $R^8$ is selected from hydrogen, methyl, ethyl, propyl, and isopropyl. In an even further aspect, $R^8$ is selected from hydrogen and methyl.

In a further aspect, $R^8$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^8$ is selected from methyl, ethyl, propyl, isopropyl, tert-butyl, sec-butyl, isobutyl, and tert-butyl. In a yet further aspect, $R^8$ is selected from methyl, ethyl, propyl, and isopropyl. In an even further aspect, $R^8$ is methyl.

j. $R^9$ Groups

In one aspect, $R^9$ is selected from hydrogen and C1-C6 alkyl. In a further aspect, $R^9$ is hydrogen. In a further aspect, $R^9$ is C1-C6 alkyl, for example, C1-C4 alkyl.

In a further aspect, $R^9$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^9$ is selected from hydrogen, methyl, ethyl, propyl, isopropyl, tert-butyl, sec-butyl, isobutyl, and tert-butyl. In a yet further aspect, $R^9$ is selected from hydrogen, methyl, ethyl, propyl, and isopropyl. In an even further aspect, $R^9$ is selected from hydrogen and methyl.

In a further aspect, $R^9$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^9$ is selected from methyl, ethyl, propyl, isopropyl, tert-butyl, sec-butyl, isobutyl, and tert-butyl. In a yet further aspect, $R^9$ is selected from methyl, ethyl, propyl, and isopropyl. In an even further aspect, $R^9$ is methyl.

k. $R^{10}$ Groups

In one aspect, $R^{10}$ is selected from hydrogen and C1-C6 alkyl. In a further aspect, $R^{10}$ is hydrogen. In a further aspect, $R^{10}$ is C1-C6 alkyl, for example, C1-C4 alkyl.

In a further aspect, $R^{10}$ is selected from hydrogen, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^{10}$ is selected from hydrogen, methyl, ethyl, propyl, isopropyl, tert-butyl, sec-butyl, isobutyl, and tert-butyl. In a yet further aspect, $R^{10}$ is selected from hydrogen, methyl, ethyl, propyl, and isopropyl. In an even further aspect, $R^{10}$ is selected from hydrogen and methyl.

In a further aspect, $R^{10}$ is selected from methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl. In a still further aspect, $R^{10}$ is selected from methyl, ethyl, propyl, isopropyl, tert-butyl, sec-butyl, isobutyl, and tert-butyl. In a yet further aspect, $R^{10}$ is selected from methyl, ethyl, propyl, and isopropyl. In an even further aspect, $R^{10}$ is methyl.

l. $R^{11}$ Groups

In one aspect, each $R^{11}$ group (i.e., either of $R^{11a}$ and $R^{11b}$) is independently selected from hydrogen, halogen, and C1-C6 alkyl, for example, C1-C4 alkyl. In a further aspect, $R^{11a}$ is hydrogen. In a further aspect, $R^{11}$ is C1-C6 alkyl. In a further aspect, $R^{11b}$ is hydrogen. In a further aspect, both $R^{11a}$ and $R^{11b}$ are hydrogen.

m. $R^{12A}$ Groups

In one aspect, $R^{12a}$ is selected from hydrogen, halogen, and C1-C6 alkyl, for example, C1-C4 alkyl. In a further aspect, $R^{12a}$ is hydrogen. In a further aspect, $R^{12a}$ is C1-C6 alkyl.

In a further aspect, all of $R^{11a}$, $R^{11b}$, and $R^{12a}$ are hydrogen.

n. $R^{12B}$ Groups

In one aspect, $R^{12b}$ is selected from hydroxyl and a group having a structure represented by a formula:

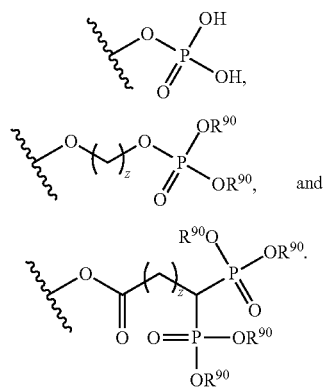

In a further respect, $R^{12b}$ is hydroxyl. In a still further aspect, $R^{12b}$ is a group having a structure represented by a formula:

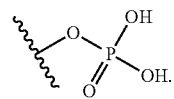 [SMILES: *OP(=O)(O)O]

In a further aspect, $R^{12b}$ is a group having a structure represented by a formula:

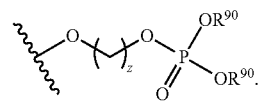

In a further aspect, $R^{12b}$ is a group having a structure represented by a formula:

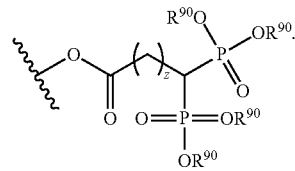

In a further aspect, $R^{12b}$ is selected from a group having a structure represented by a formula:

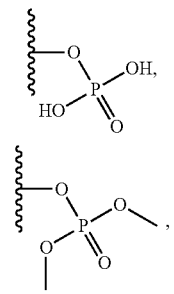

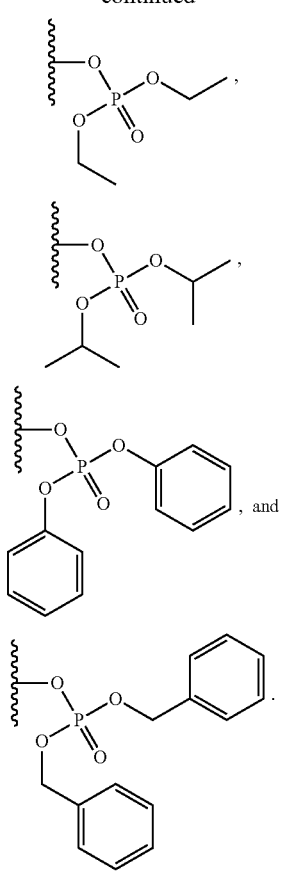
In a further aspect, $R^{12b}$ is selected from a group having a structure represented by a formula:
In a further aspect, $R^{12b}$ is selected from a group having a structure represented by a formula:

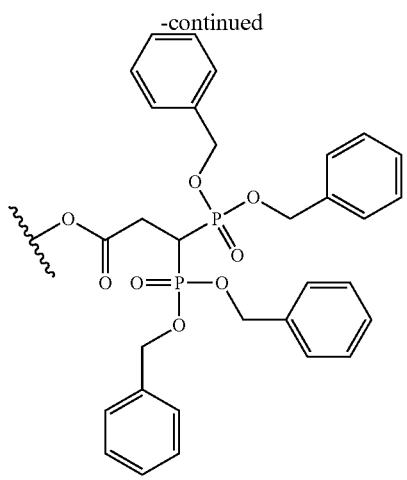

In a further aspect, $R^{12b}$ is selected from a group having a structure represented by a formula:

In a further aspect, $R^{12b}$ is selected from a group having a structure represented by a formula:

In a further aspect, all of $R^{11a}$, $R^{11b}$, and $R^{12b}$ are hydrogen, and $R^{12b}$ is hydroxyl.

In a further aspect, all of $R^{11a}$, $R^{11b}$, and $R^{12b}$ are hydrogen, and $R^{12b}$ is a group having a structure represented by a formula:

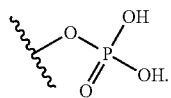

In a further aspect, all of $R^{11a}$, $R^{11b}$, and $R^{12b}$ are hydrogen, and $R^{12b}$ is a group having a structure represented by a formula:

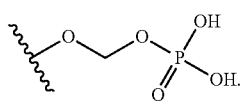 [SMILES: *OCOP(=O)(O)O]

In a further aspect, all of $R^{11a}$, $R^{11b}$, and $R^{12b}$ are hydrogen, and $R^{12b}$ is a group having a structure represented by a formula:

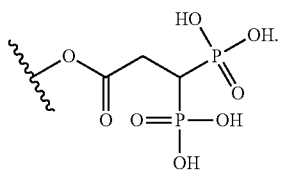 [SMILES: *OC(=O)CC(P(=O)(O)O)P(=O)(O)O]

o. $R^{13}$ Groups

In one aspect, $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl. In a further aspect, $R^{13}$ is a five-membered heterocycle. In a further aspect, $R^{13}$ is a six-membered heterocycle. In a further aspect, $R^{13}$ is a C4 heterocycle. In a further aspect, $R^{13}$ is a C5 heterocycle. In a further aspect, $R^{13}$ is unsubstituted. In a further aspect, $R^{13}$ is monosubstituted. In a further aspect, $R^{13}$ is disubstituted.

In a further aspect, $R^{13}$ is substituted with 1-3 groups selected from halogen, cyano, C1-C6 alkyl, C1-C6 haloalkyoxy, C1-C6 haloalkyl, and C1-C6 polyhaloalkyl. In a further aspect, $R^{13}$ is substituted with 1-2 groups selected from halogen, cyano, C1-C6 alkyl, C1-C6 haloalkyoxy, C1-C6 haloalkyl, and C1-C6 polyhaloalkyl. In a further aspect, $R^{13}$ is substituted with 1-3 groups selected from C1-C6 alkyl, C1-C6 haloalkyoxy, C1-C6 haloalkyl, and C1-C6 polyhaloalkyl.

In a further aspect, $R^{13}$ is selected from 4-methylpiperazin-1-yl, piperazin-1-yl, morpholinyl, piperidin-1-yl, 1,3-oxazinan-3-yl, 1,3,5-dioxazinan-5-yl, 1,3,5-triazinan-1-yl, tetrahydropyrimidin-1(2H)-yl, and thiomorpholinyl. In a further aspect, $R^{13}$ is selected from 3-methylimidazolidin-1-yl, imidazolidin-1-yl, oxazolidin-3-yl, and thiazolidin-3-yl.

p. $R^{14}$ Groups

In one aspect, $R^{14}$ is selected from hydrogen and C1-C6 alkyl. In a further aspect, $R^{14}$ is hydrogen. In a further aspect, $R^{14}$ is selected from hydrogen and C1-C6 alkyl, for example, C1-C4 alkyl.

q. $R^{15}$ Groups

In one aspect, wherein $R^{15}$ is selected from hydrogen, C1-C6 alkyl, C1-C6 haloalkyl, and C1-C6 polyhaloalkyl. In a further aspect, $R^{15}$ is hydrogen or C1-C6 alkyl, for example, C1-C4 alkyl. In a further aspect, $R^{15}$ is hydrogen. In a further aspect, $R^{15}$ is C1-C6 alkyl, for example, C1-C4 alkyl. In a further aspect, $R^{15}$ is C1-C6 haloalkyl or C1-C6 polyhaloalkyl. In a further aspect, $R^{15}$ is selected from hydrogen, C1-C6 alkyl, C1-C6 haloalkyl, and C1-C6 polyhaloalkyl.

r. $R^{16}$ Groups

In one aspect, $R^{16}$ is hydrogen, a protecting group, or a group having a structure represented by a formula:

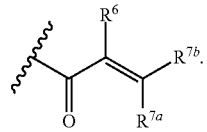

In a further aspect, $R^{16}$ is hydrogen. In a further aspect, $R^{16}$ is a protecting group, for example, an amine protecting group. In a further aspect, $R^{16}$ is a group having a structure represented by a formula:

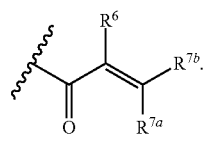

s. $R^{17}$ Groups

In one aspect, each $R^{17}$ group (i.e., $R^{17a}$ and $R^{17b}$) is independently selected from hydrogen, and C1-C6 alkyl; or $R^{17a}$ and $R^{17b}$ are covalently bonded and, together with the intermediate atoms, comprise an optionally substituted heterocyclic ring. In a further aspect, $R^{17a}$ is hydrogen or C1-C6 alkyl. In a further aspect, $R^{17a}$ is hydrogen or C1-C6 alkyl, for example, C1-C4 alkyl. In a further aspect, $R^{17b}$ is hydrogen or C1-C6 alkyl. In a further aspect, $R^{17b}$ is hydrogen or C1-C6 alkyl, for example, C1-C4 alkyl. In a further aspect, $R^{17a}$ and $R^{17b}$ are both hydrogen. In a further aspect, $R^{17a}$ and $R^{17b}$ are both C1-C6 alkyl, for example, C1-C4 alkyl.

In a further aspect, $R^{17a}$ and $R^{17b}$ are covalently bonded and, together with the intermediate atoms, comprise an optionally substituted heterocyclic ring. In a further aspect, $R^{17a}$ and $R^{17b}$ are covalently bonded and, together with the intermediate boron, comprise boronic acid pinacol ester, boronic acid trimethylene glycol ester, or 9-borabicyclo [3.3.1]nonane (9-BBN).

t. $R^{18}$ Groups

In one aspect, each $R^{18}$ group (i.e., $R^{18a}$, $R^{18b}$, and $R^{18c}$) is independently selected from C1-C6 alkyl, for example, C1-C4 alkyl. In a further aspect, $R^{18a}$, $R^{18b}$, and $R^{18c}$ are all butyl.

In a further aspect, each $R^{18}$ group (i.e., $R^{18a}$, $R^{18b}$, and $R^{18c}$) is independently selected from methyl, ethyl, propyl, isopropyl, tert-butyl, sec-butyl, isobutyl, neopentyl, isopentyl, sec-pentyl, tert-pentyl, 3,3-dimethylbutan-2-yl, and 2,3-dimethylbutan-2-yl. In a yet further aspect, each $R^{18}$ group (i.e., $R^{18a}$, $R^{18b}$, and $R^{18c}$) is independently selected from methyl, ethyl, propyl, isopropyl, tert-butyl, sec-butyl, isobutyl, and tert-butyl. In a still further aspect, each $R^{18}$ group (i.e., $R^{18a}$, $R^{18b}$, and $R^{18c}$) is independently selected from methyl, ethyl, propyl, and isopropyl.

u. $R^{31}$ Groups

In one aspect, each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that at least one occurrence is hydrogen. In a further aspect, each occurrence of $R^{31}$ is hydrogen.

In a further aspect, each occurrence of $R^{31}$ is selected from hydrogen, halogen, cyano, C1-C6 alkyl, C1-C6 haloalkyoxy, C1-C6 haloalkyl, and C1-C6 polyhaloalkyl, provided that no more than three occurrences is not hydrogen.

In a further aspect, each occurrence of $R^{31}$ is selected from hydrogen, halogen, cyano, methyl, ethyl, propyl, isopropyl, tert-butyl, sec-butyl, isobutyl, neopentyl, isopentyl, sec-pentyl, tert-pentyl, 3,3-dimethylbutan-2-yl, 2,3-dimethylbutan-2-yl, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, and —(CH$_2$)$_2$CI$_3$. In a still further aspect, each occurrence of $R^{31}$ is selected from hydrogen, —F, —Cl, —Br, methyl, ethyl, propyl, isopropyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a yet further aspect, each occurrence of $R^{31}$ is selected from hydrogen, —F, methyl, —CH$_2$F, —CHF$_2$, and —CF$_3$.

In a further aspect, each occurrence of $R^{31}$ is selected from hydrogen and halogen. In a still further, each occurrence of $R^{31}$ is selected from hydrogen, —F, and —Cl. In a yet further, each occurrence of $R^{31}$ is selected from hydrogen and —F.

For example, it is understood that a structure of a compound can be represented by a formula:

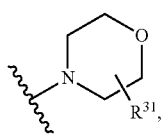

which is understood to be equivalent to a formula:

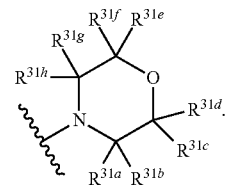

That is, $R^{31}$ is understood to represent eight independent substituents, $R^{31a}$, $R^{31b}$, $R^{31c}$, $R^{31d}$, $R^{31e}$, $R^{31f}$, $R^{31g}$, and $R^{31h}$. By "independent substituents," it is meant that each R substituent can be independently defined. For example, if in one instance $R^{31a}$ is halogen, then $R^{31b}$ is not necessarily halogen in that instance.

In another example, it is understood that a structure of a compound can be represented by a formula:

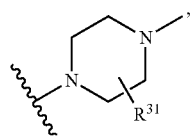

which is understood to be equivalent to a formula:

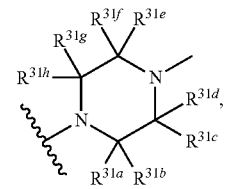

That is, $R^{31}$ is understood to represent eight independent substituents, $R^{31a}$, $R^{31b}$, $R^{31c}$, $R^{31d}$, $R^{31e}$, $R^{31f}$, $R^{31g}$, and $R^{31h}$.

In a still further example, it is understood that a structure of a compound can be represented by a formula:

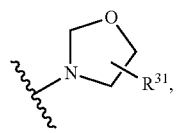

which is understood to be equivalent to a formula:

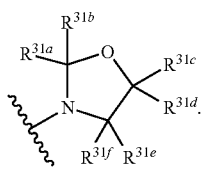

That is, $R^{31}$ is understood to represent eight independent substituents, $R^{31a}$, $R^{31b}$, $R^{31c}$, $R^{31d}$, $R^{31e}$, and $R^{31f}$.

In a yet further example, it is understood that a structure of a compound can be represented by a formula:

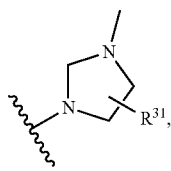

which is understood to be equivalent to a formula:

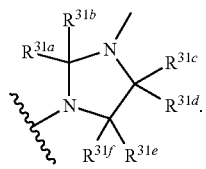

That is, $R^{31}$ is understood to represent eight independent substituents, $R^{31a}$, $R^{31b}$, $R^{31c}$, $R^{31d}$, $R^{31e}$, and $R^{31f}$.

v. $R^{90}$ Groups

In one aspect, each occurrence of $R^{90}$, when present, is independently selected from hydrogen, C1-C8 alkyl, and phenyl. In a further aspect, each occurrence of $R^{90}$, when present, is hydrogen. In a still further aspect, each occurrence of $R^{90}$, when present, is phenyl. In a yet further aspect, each occurrence of $R^{90}$, when present, is methyl. In an even further aspect, each occurrence of $R^{90}$, when present, is ethyl. In a still further aspect, each occurrence of $R^{90}$, when present, is propyl. In a yet further aspect, each occurrence of $R^{90}$, when present, is isopropyl. In an even further aspect, $R^{90}$, when present, is butyl.

In various further aspects, each occurrence of $R^{90}$, when present, is independently selected from hydrogen and C1-C8 alkyl. In a still further aspect, each occurrence of $R^{90}$, when present, is independently selected from hydrogen, methyl, ethyl, propyl, isopropyl, butyl, isobutyl, tert-butyl, and sec-butyl. In a yet further aspect, each occurrence of $R^{90}$, when present, is independently selected from hydrogen, methyl, ethyl, propyl, and isopropyl. In an even further aspect, each occurrence of $R^{90}$, when present, is independently selected from hydrogen, methyl, and ethyl.

In a further aspect, each occurrence of $R^{90}$, when present, is independently selected from phenyl and C1-C8 alkyl. In a still further aspect, each occurrence of $R^{90}$, when present, is independently selected from phenyl, methyl, ethyl, propyl, isopropyl, butyl, isobutyl, tert-butyl, and sec-butyl. In a yet further aspect, each occurrence of $R^{90}$, when present, is independently selected from phenyl, methyl, ethyl, propyl, and isopropyl. In an even further aspect, each occurrence of $R^{90}$, when present, is independently selected from phenyl, methyl, and ethyl.

In a further aspect, each occurrence of $R^{90}$, when present, is independently selected from hydrogen, phenyl, and C1-C6 alkyl. In a still further aspect, each occurrence of $R^{90}$, when present, is independently selected from hydrogen, phenyl, methyl, ethyl, propyl, isopropyl, butyl, isobutyl, tert-butyl, and sec-butyl. In a yet further aspect, each occurrence of $R^{90}$, when present, is independently selected from hydrogen, phenyl, methyl, ethyl, propyl, and isopropyl. In an even further aspect, each occurrence of $R^{90}$, when present, is independently selected from hydrogen, phenyl, methyl, and ethyl.

In a further aspect, each occurrence of $R^{90}$, when present, is independently selected from hydrogen and phenyl.

w. $X^1$ Groups

In one aspect, $X^1$ is halide or pseudohalide. In a further aspect, $X^1$ is halogen, for example, fluoro, chloro, bromo, or iodo. In a further aspect, $X^1$ is chloro, bromo, or iodo. In a further aspect, $X^1$ is bromo or iodo. In a further aspect, $X^1$ is chloro. In one aspect, $X^1$ is pseudohalide, for example, triflate, mesylate, tosylate, or brosylate. In a further aspect, $X^1$ is a group capable of undergoing a transition-metal mediated coupling reaction.

x. $X^2$ Groups

In one aspect, $X^2$ is halide, pseudohalide, hydrogen, C1-C6 alkyl, or a group having a structure represented by the formula:

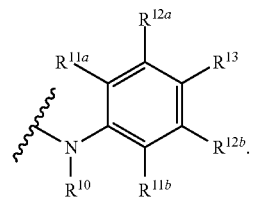

In a further aspect, $X^2$ is hydrogen or C1-C6 alkyl. In a further aspect, $X^2$ is hydrogen. In a further aspect, $X^2$ is C1-C6 alkyl, for example, C1-C4 alkyl.

In a further aspect, $X^2$ is halide or pseudohalide. In a further aspect, $X^2$ is halogen, for example, fluroro, chloro, bromo, or iodo. In a further aspect, $X^2$ is chloro, bromo, or iodo. In a further aspect, $X^2$ is bromo or iodo. In a further aspect, $X^2$ is chloro. In one aspect, $X^2$ is pseudohalide, for example, triflate, mesylate, tosylate, or brosylate. In a further aspect, $X^2$ is a group capable of undergoing a transition-metal mediated coupling reaction.

In a further aspect, $X^2$ is a group having a structure represented by the formula:

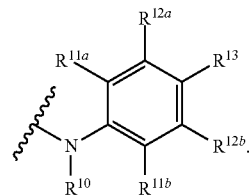

In a further aspect, both $X^1$ and $X^2$ are halide. In a further aspect, both $X^1$ and $X^2$ are chloro.

y. M Groups

In one aspect, M is a group capable of undergoing a transition-metal mediated coupling reaction. In a further aspect, M is selected from:

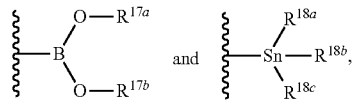

wherein each of $R^{17a}$ and $R^{17b}$ is independently selected from hydrogen, and C1-C6 alkyl; or $R^{17a}$ and $R^{17b}$ are covalently bonded and, together with the intermediate atoms, comprise an optionally substituted heterocyclic ring; and wherein each of $R^{18a}$, $R^{18b}$, and $R^{18c}$ is independently C1-C6 alkyl.

In a further aspect, M is a group having a structure

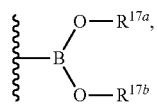

wherein each of R[17a] and R[17b] is independently selected from hydrogen, and C1-C6 alkyl; or R[17a] and R[17b] are covalently bonded and, together with the intermediate atoms, comprise an optionally substituted heterocyclic ring.

In a further aspect, M is a group having a structure:

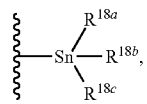

wherein each of R[18a], R[18b], and R[18c] is independently C1-C6 alkyl.

2. Example Compounds

In one aspect, a compound can be present as:

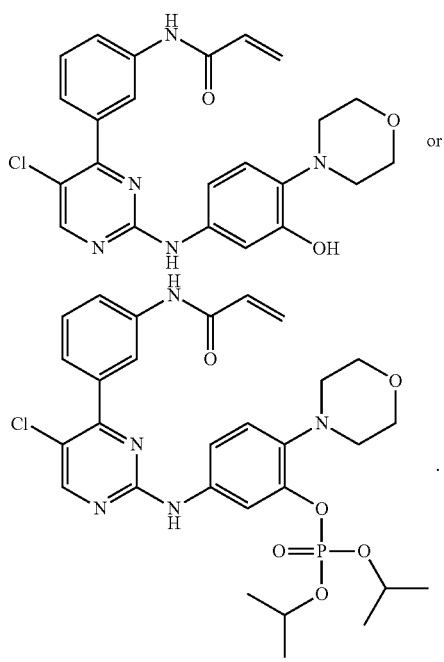

or

In one aspect, a compound can be present as:

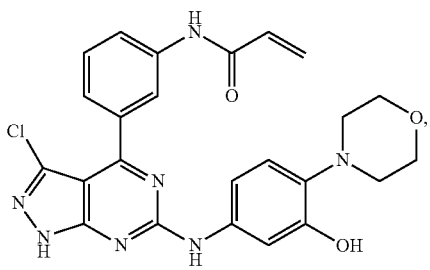

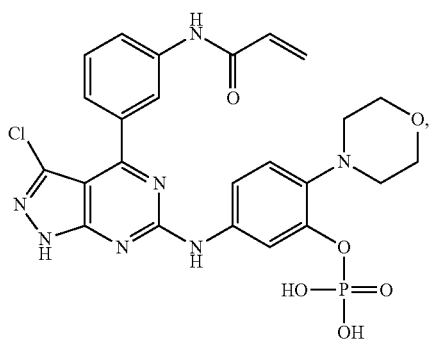

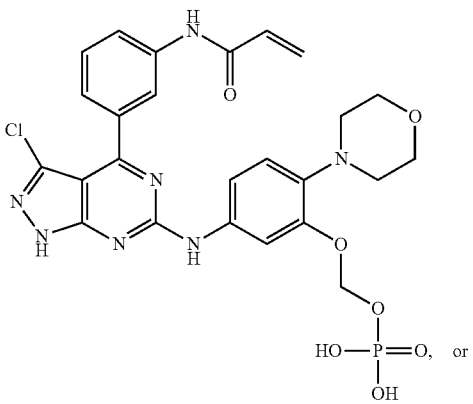

or

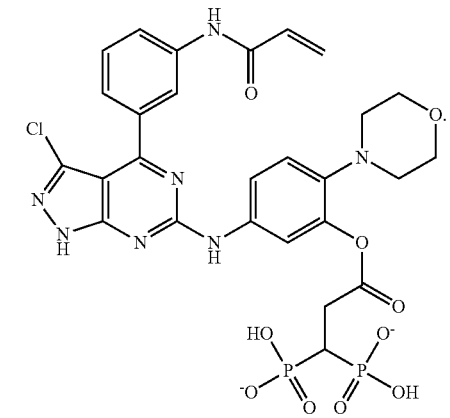

In a further aspect, a compound can be present as:

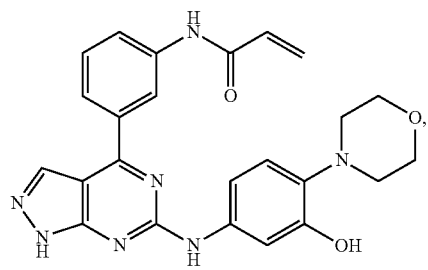

-continued
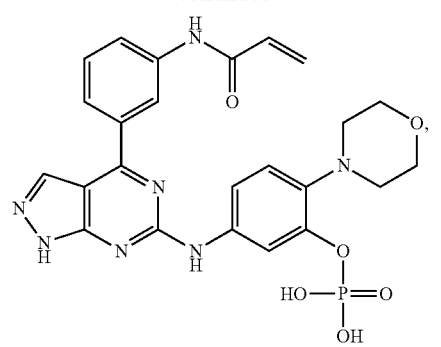
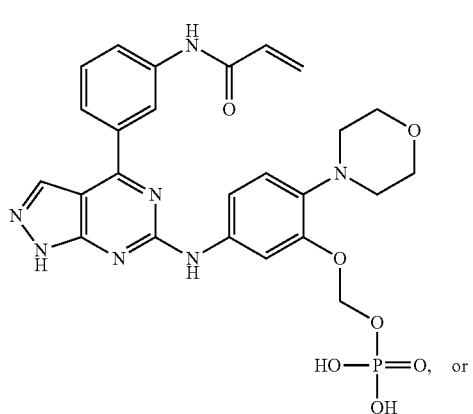
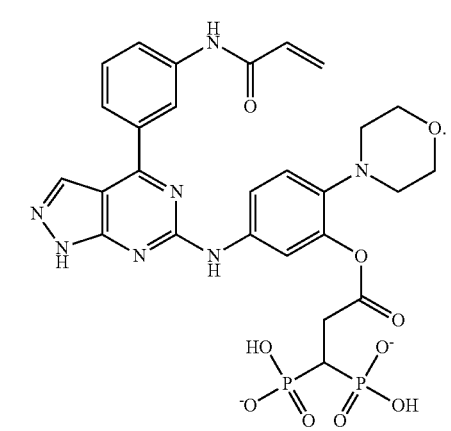
In a further aspect, a compound can be present as:
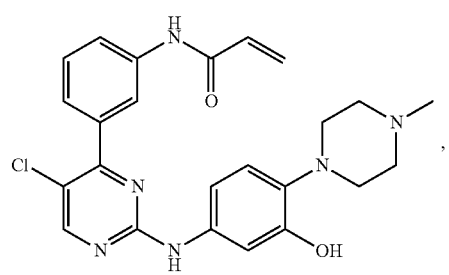
-continued
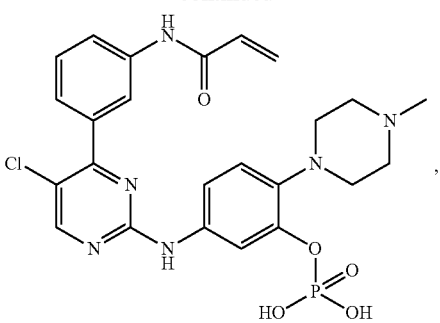
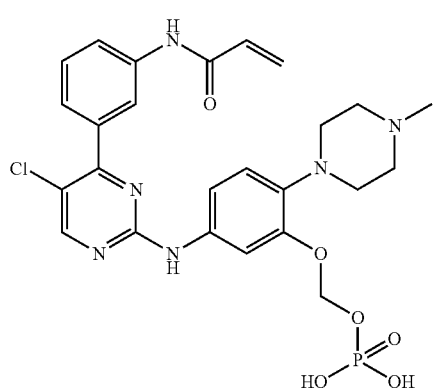
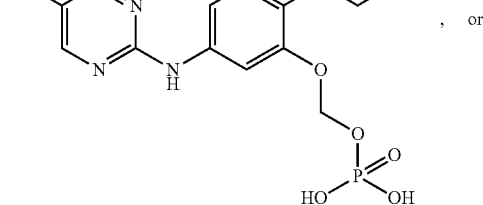
, or
In a further aspect, a compound can be present as:
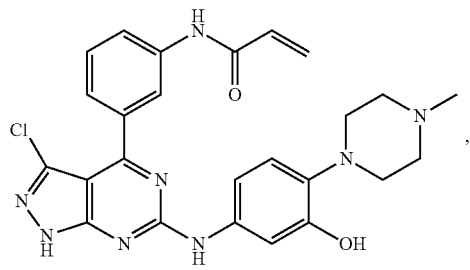

99
-continued
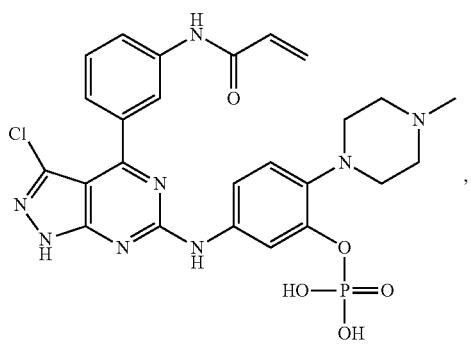
,
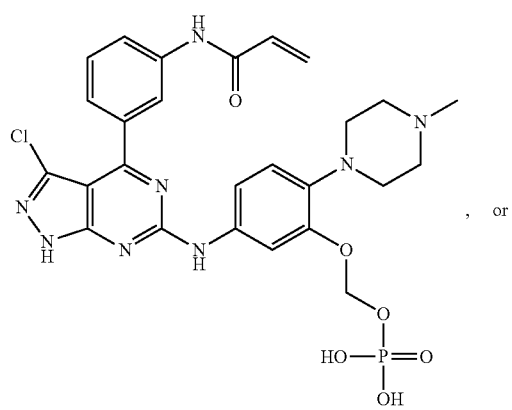
, or
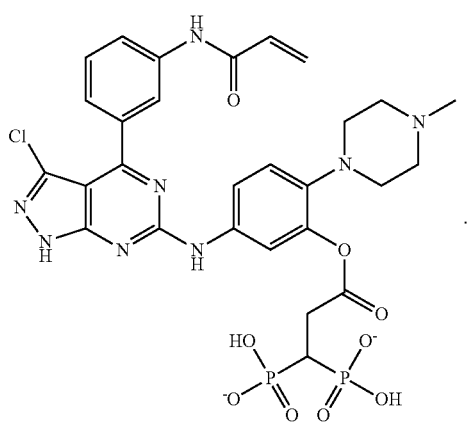
.
In a further aspect, a compound can be present as:
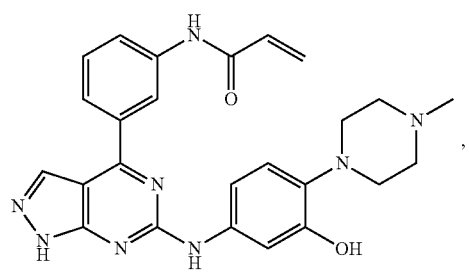
,
100
-continued
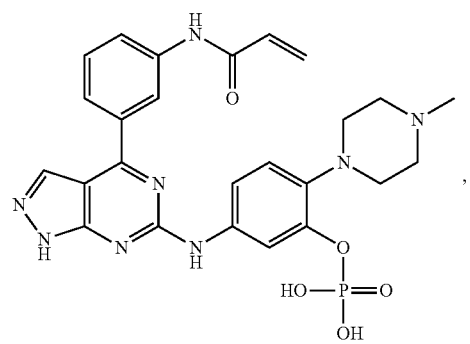
,
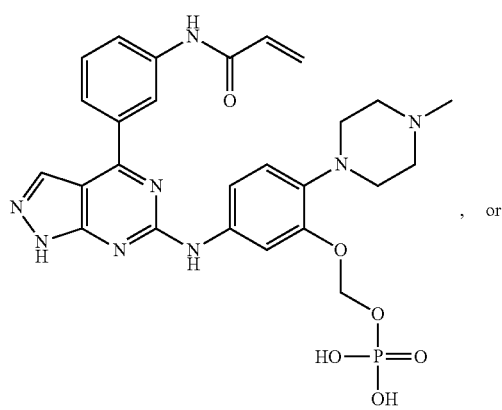
, or
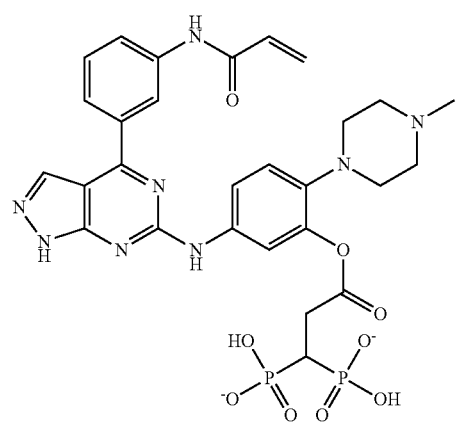
.
In a further aspect, a compound can be present as:
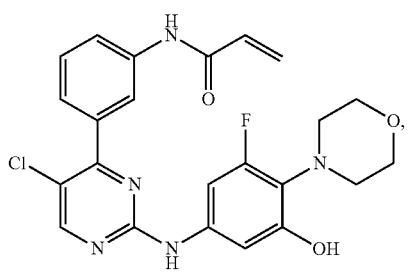
, -continued
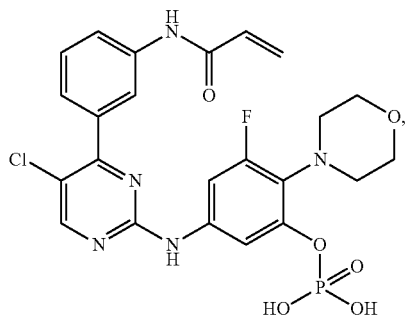
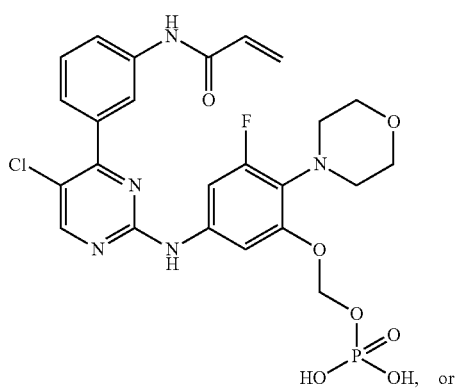
or
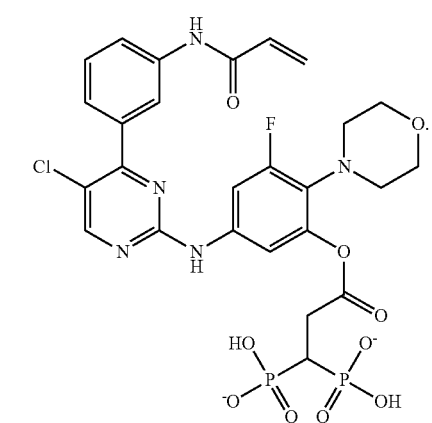
In a further aspect, a compound can be present as:
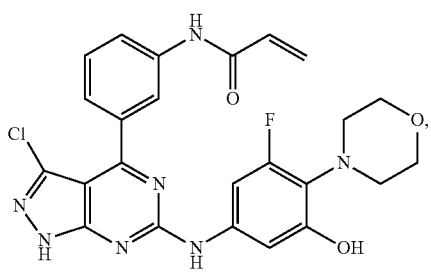
-continued
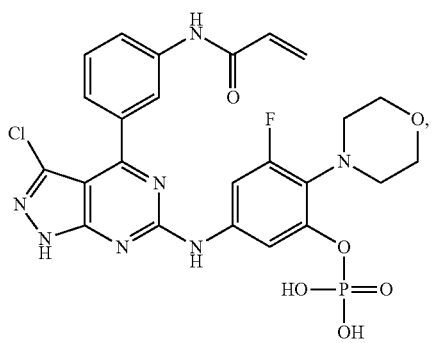
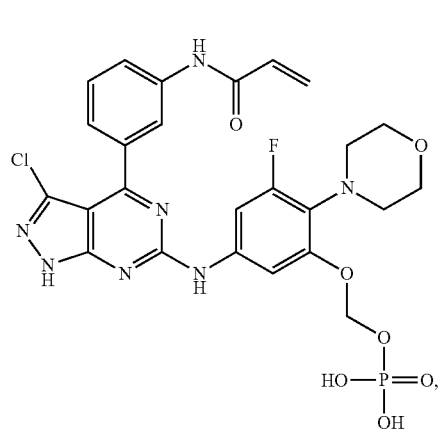
or
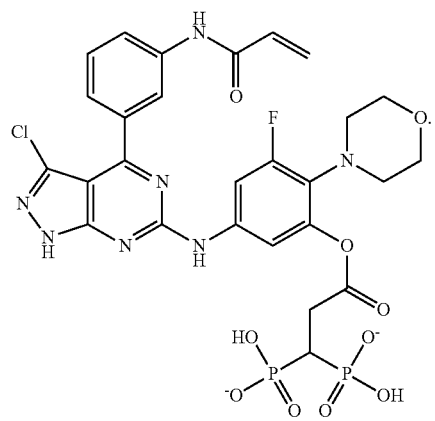
In a further aspect, a compound can be present as:
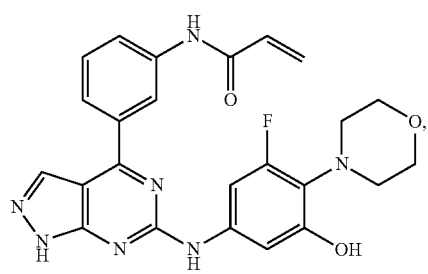

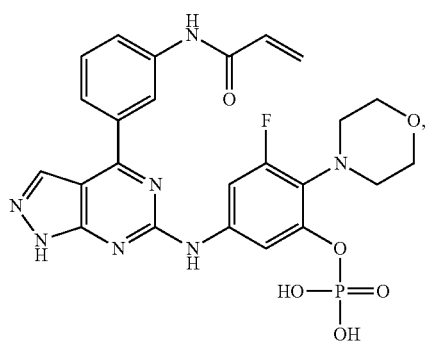
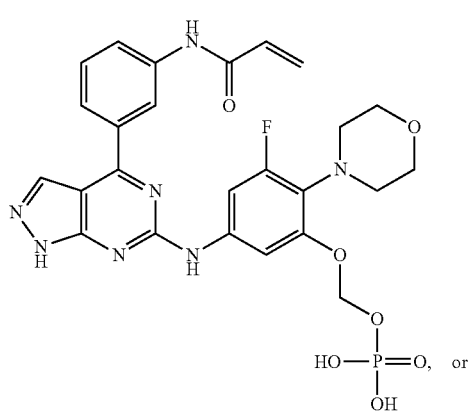
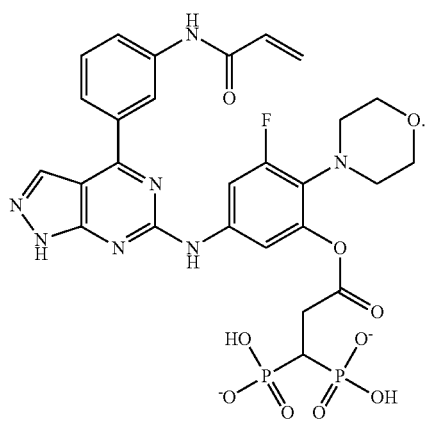
In a further aspect, a compound can be present as:
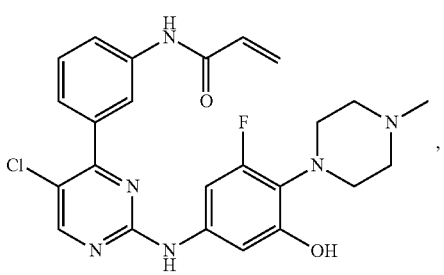
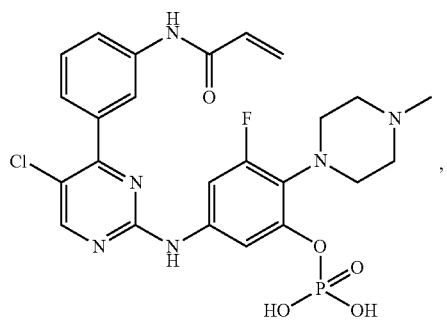
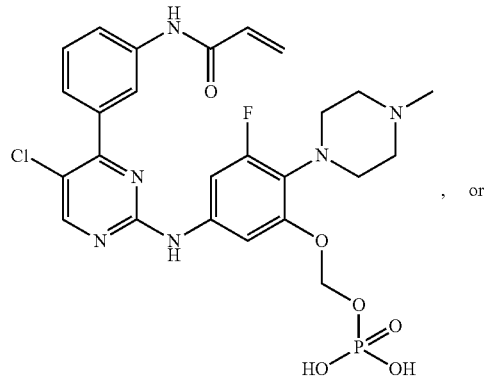
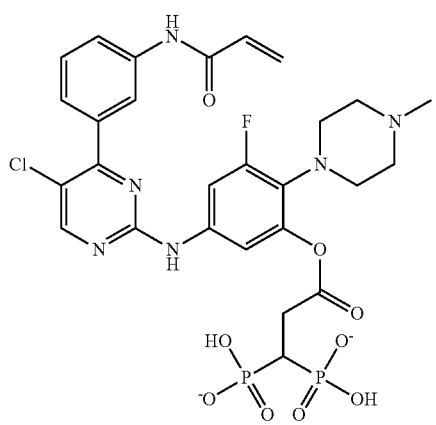
In a further aspect, a compound can be present as:
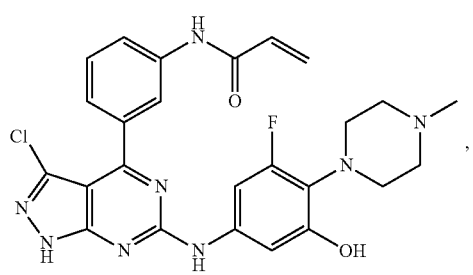

-continued

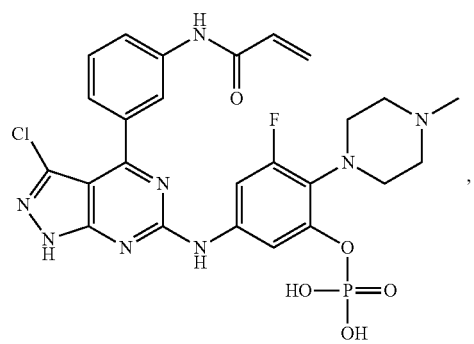

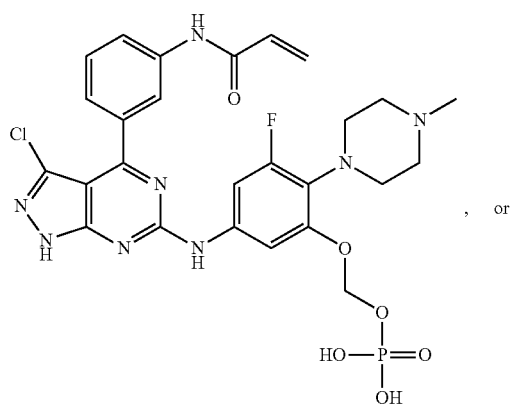

, or

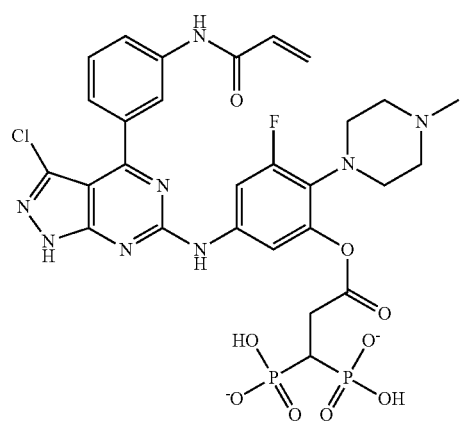

In a further aspect, a compound can be present as:

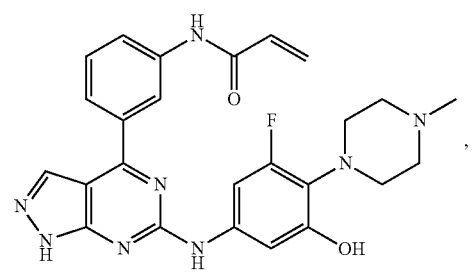

-continued

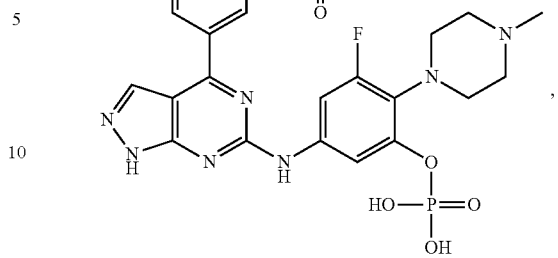

,

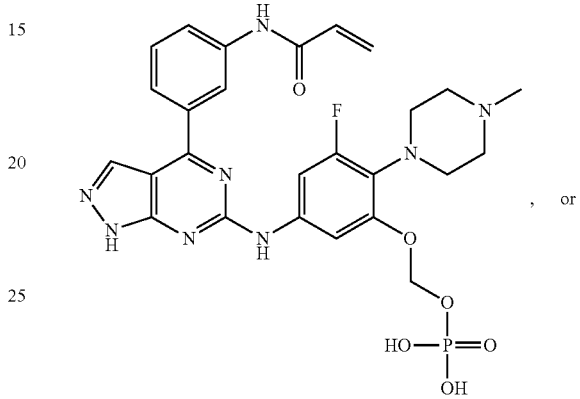

, or

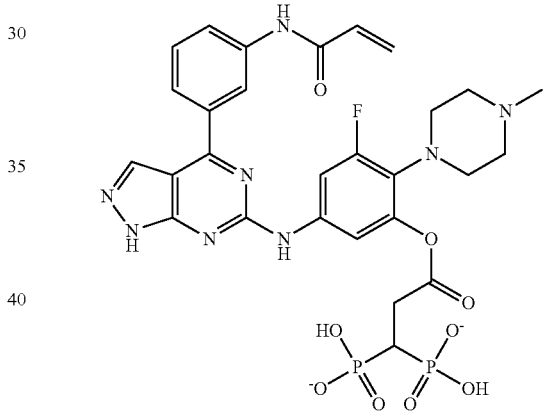

It is contemplated that one or more compounds can optionally be omitted from the disclosed invention.

3. Inhibition of Protein Kinase Activity

As discussed herein, BTK is a key regulator of B-cell development, activation, signaling and survival (e.g. see Kurosaki, T. Curr. Opin. Immunol. (2000) 12:276-281; and Schaeffer, E. M. and P. L. Schwartzberg. Curr. Opin. Immunol. (2000) 12:282-288). Moreover, B cell receptor signaling is also implicated in the survival of malignant B-cells and acts as a crucial regulator of cellular differentiation, activation, proliferation, and survival (R. W. Hendriks, Nat. Chem. Biol. (2011) 7:4-5). In addition, given the overall role of BTK in B-cell function, it is an important target for therapeutic intervention targeting inflammatory diseases involving B-cell activation, e.g. rheumatoid arthritis. Aspects of the B-cell signaling pathway are shown in FIG. 1.

Figure 2:
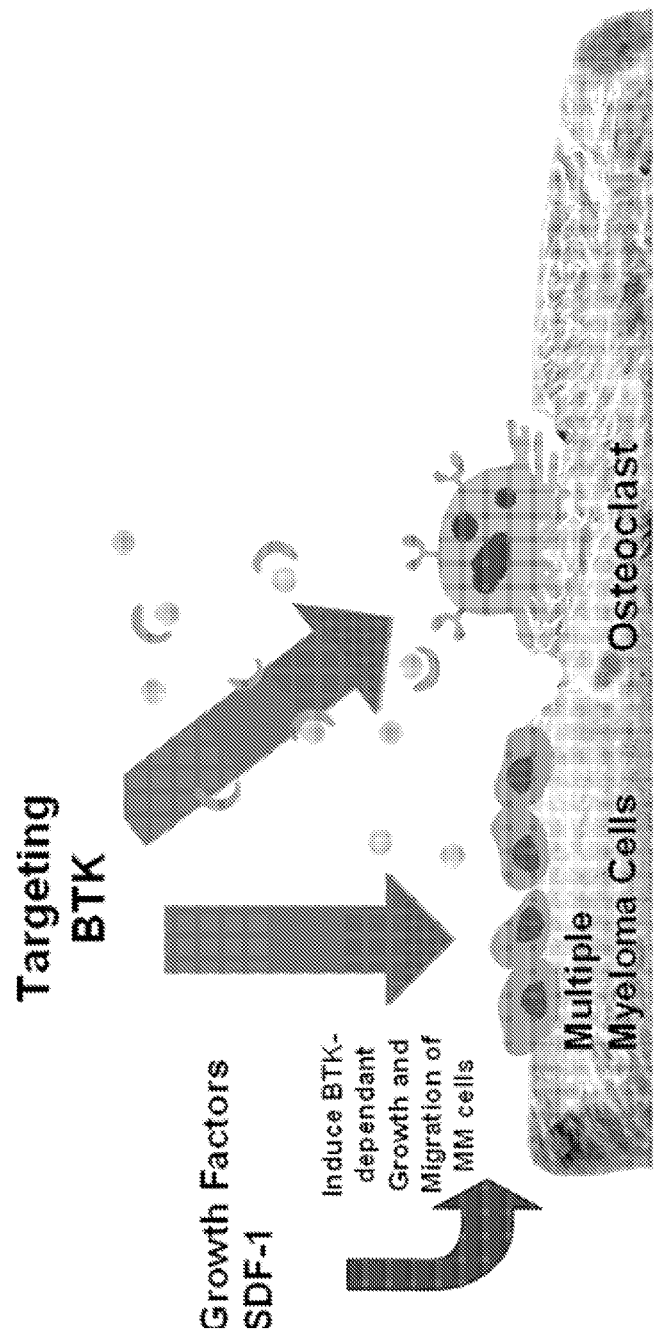
FIG. 2 shows a schematic of a model for dual effects on multiple myeloma cells and activated osteoclasts in the bone marrow from inhibition of BTK.

As shown schematically in FIG. 2, in certain aspects, targeting BTK has biological advantages for therapeutic intervention in myelomas. For example, without wishing to be bound by a particular theory, growth factors can induce BTK-dependent growth and migration of myeloma cells in the bone marrow. In addition, osteoclasts play a role in the development of myelomic diseases and BTK is expressed in osteoclasts. Thus, without wishing to be bound by a particular theory, compounds that can inhibit the activity of BTK can directly act on myeloma cells and activated osteoclasts in the bone marrow to provide a dual approach to therapeutic intervention in this disease.

Generally, the disclosed compounds exhibit modulation of the BCR signaling pathway. In a further aspect, the compound exhibits inhibition of a protein kinase.

In a further aspect, the protein kinase is a member of the Tec family of tyrosine protein kinases.

In a further aspect, the protein kinase is selected from tyrosine-protein kinase ITK/TSK, tyrosine-protein kinase BTK, cytoplasmic tyrosine-protein kinase BMX, receptor tyrosine-protein kinase erbB-4, tyrosine-protein kinase Tec, and epidermal growth factor receptor (receptor tyrosine-protein kinase erbB-1). In a further aspect, the protein kinase is selected from tyrosine-protein kinase ITK/TSK, tyrosine-protein kinase BTK, and cytoplasmic tyrosine-protein kinase BMX. In a further aspect, the protein kinase is tyrosine-protein kinase BTK.

In one aspect, the inhibition is with an $IC_{50}$ of less than about $1.0 \times 10^{-4}$ M. In a further aspect, the inhibition is with an $IC_{50}$ of less than about $1.0 \times 10^{-5}$ M. In a further aspect, the inhibition is with an $IC_{50}$ of less than about $1.0 \times 10^{-6}$ M. In a further aspect, the inhibition is with an $IC_{50}$ of less than about $1.0 \times 10^{-7}$ M. In a further aspect, the inhibition is with an $IC_{50}$ of less than about $1.0 \times 10^{-8}$ M. In a further aspect, the inhibition is with an $IC_{50}$ of less than about $1.0 \times 10^{-9}$ M.

C. Methods of Making the Compounds

In one aspect, the invention relates to methods of making compounds useful as inhibitors of protein kinase, which can be useful in the treatment of disorders of uncontrolled cellular proliferation. In a further aspect, the protein kinase is BTK.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted N-(3-(pyrimidin-4-yl)phenyl) acrylamide analogs can be prepared as shown below.

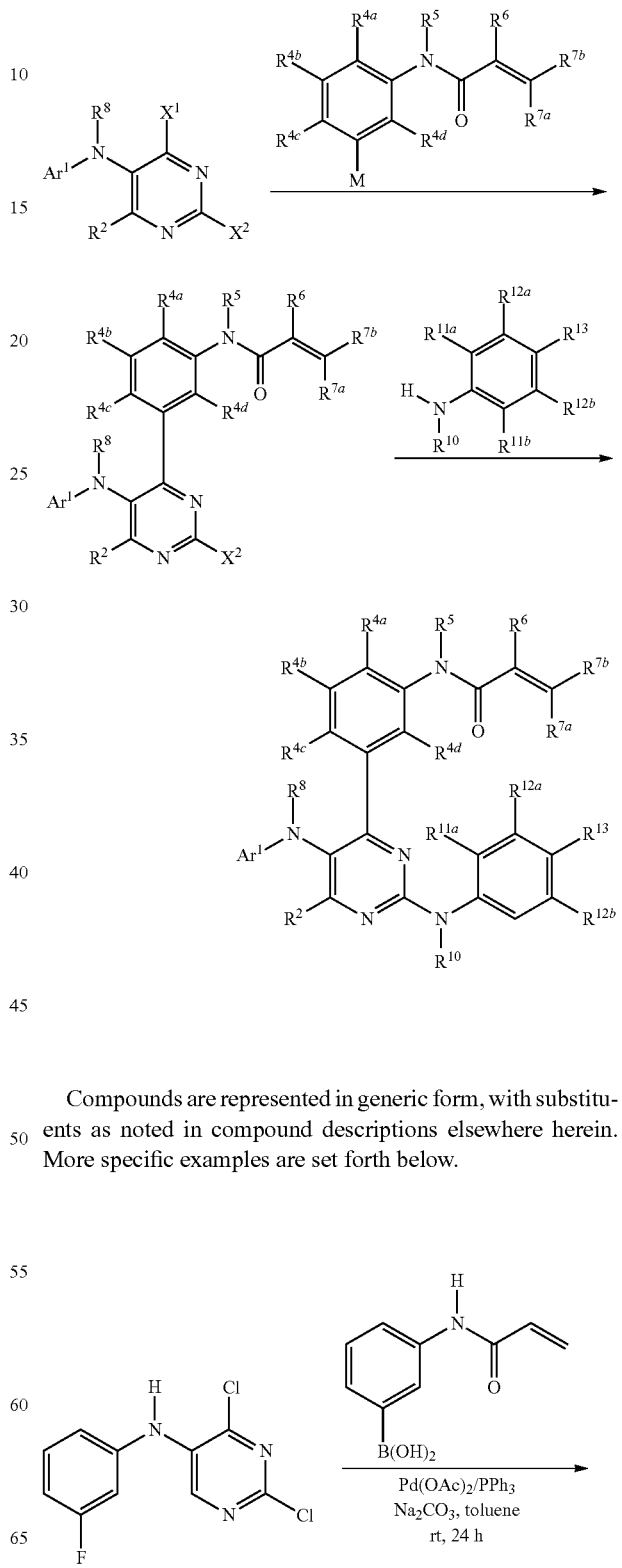

Compounds are represented in generic form, with substituents as noted in compound descriptions elsewhere herein. More specific examples are set forth below.

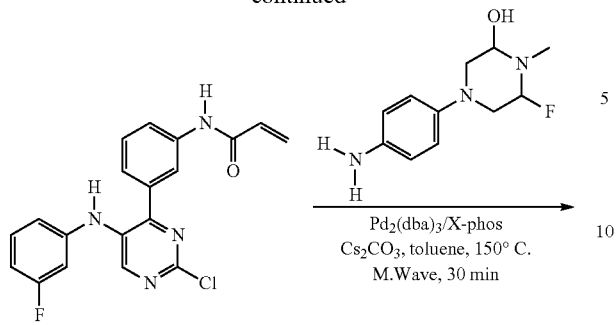

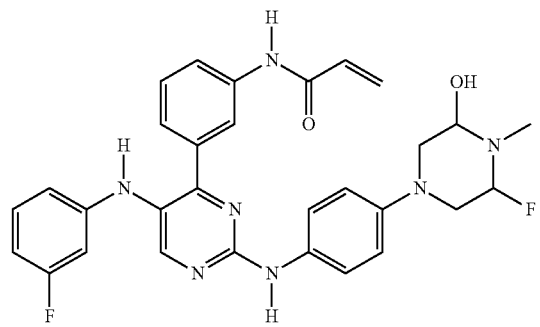

As an example, N-(3-(2-((4-(3-fluoro-5-hydroxy-4-methylpiperazin-1-yl)phenyl)amino)-5-((3-fluorophenyl)amino)pyrimidin-4-yl)phenyl)acrylamide can be prepared according to Route I. Beginning with 2,4-dichloro-N-(3-fluorophenyl)pyrimidin-5-amine, a palladium catalyzed coupling reaction with (3-acrylamidophenyl)boronic acid provides N-(3-(2-chloro-5-((3-fluorophenyl)amino)pyrimidin-4-yl)phenyl)acrylamide under mild conditions. Reaction of this product with 4-(4-aminophenyl)-6-fluoro-1-methylpiperazin-2-ol under palladium catalyzed aminolysis conditions can yield the desired product.

2. Route II

In one aspect, substituted N-(3-(pyrimidin-4-yl)phenyl)acrylamide analogs can be prepared as shown below.

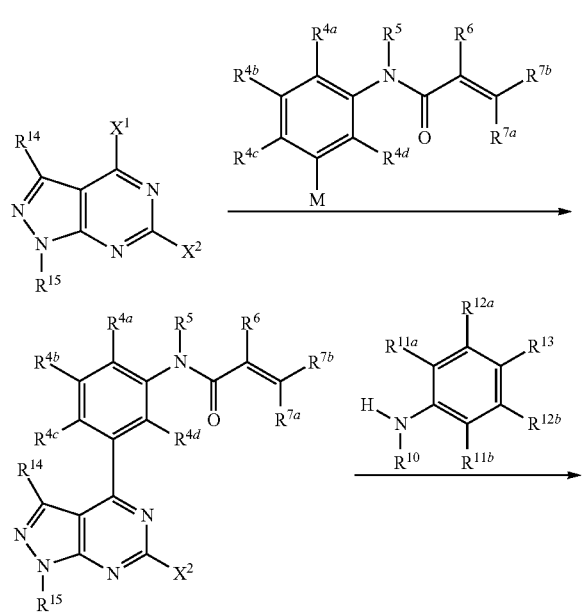

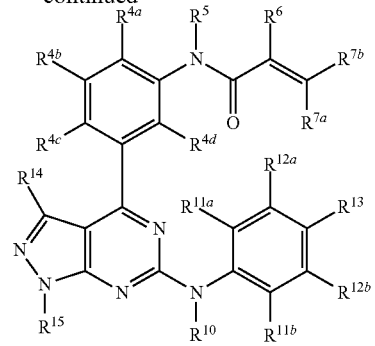

Compounds are represented in generic form, with substituents as noted in compound descriptions elsewhere herein. More specific examples are set forth below.

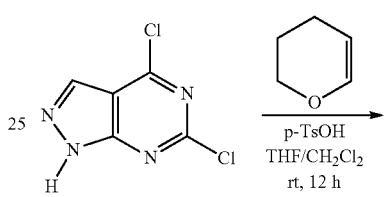

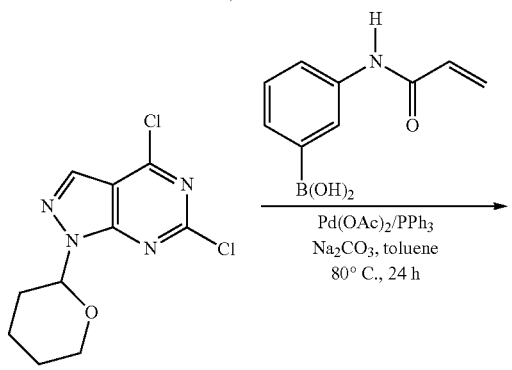

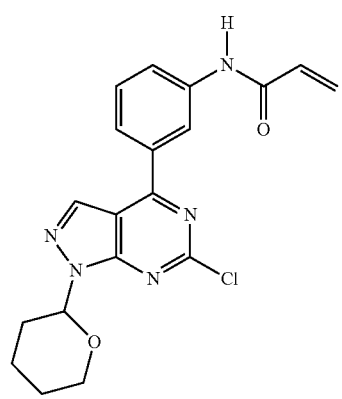

As an example, N-(3-(6-((3-fluoro-4-morpholinophenyl)amino)-1H-pyrazolo[3,4-d]pyrimidin-4-yl)phenyl)acrylamide can be prepared according to Route II. Beginning with 4,6-dichloro-1H-pyrazolo[3,4-d]pyrimidine, protection can be accomplished by reaction with 3,4-dihydro-2H-pyran in the presence of p-TsOH in a suitable solvent such as a solution of THF and methylene chloride. The reaction is carried out for a suitable period of time, e.g. about 8-18 hr, at a suitable temperature, e.g. about 15-30° C., until the reaction is complete. The completeness of the reaction can be ascertained by several convenient methods, including monitoring the reaction by TLC. The resulting 4,6-dichloro-1-(tetrahydro-2H-pyran-2-yl)-1H-pyrazolo[3,4-d]pyrimidine can then be coupled with (3-acrylamidophenyl)boronic acid under palladium catalyzed conditions to provide N-(3-(6-chloro-1-(tetrahydro-2H-pyran-2-yl)-1H-pyrazolo[3,4-d]pyrimidin-4-yl)phenyl)acrylamide.

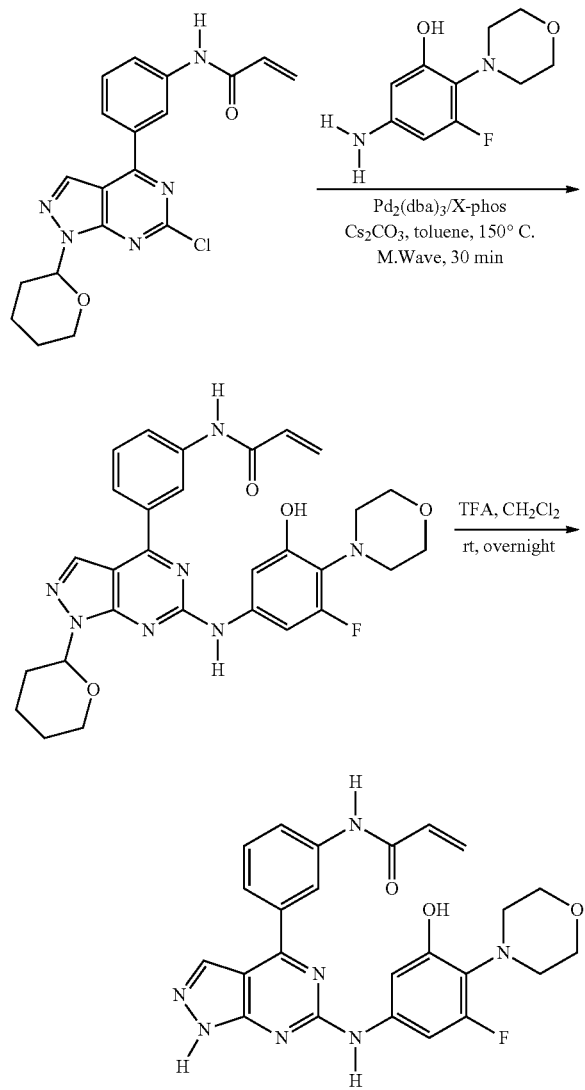

N-(3-(6-Chloro-1-(tetrahydro-2H-pyran-2-yl)-1H-pyrazolo[3,4-d]pyrimidin-4-yl)phenyl)acrylamide can then be reacted with 5-amino-3-fluoro-2-morpholinophenol under palladium catalyzed aminolysis conditions to yield N-(3-(6-((3-fluoro-5-hydroxy-4-morpholinophenyl)amino)-1-(tetrahydro-2H-pyran-2-yl)-1H-pyrazolo[3,4-d]pyrimidin-4-yl)phenyl)acrylamide, which can be deprotected under mild acidic conditions to provide N-(3-(6-((3-fluoro-5-hydroxy-4-morpholinophenyl)amino)-1H-pyrazolo[3,4-d]pyrimidin-4-yl)phenyl)acrylamide.

3. Route III

In one aspect, substituted N-(3-(pyrimidin-4-yl)phenyl) acrylamide analogs can be prepared as shown below.

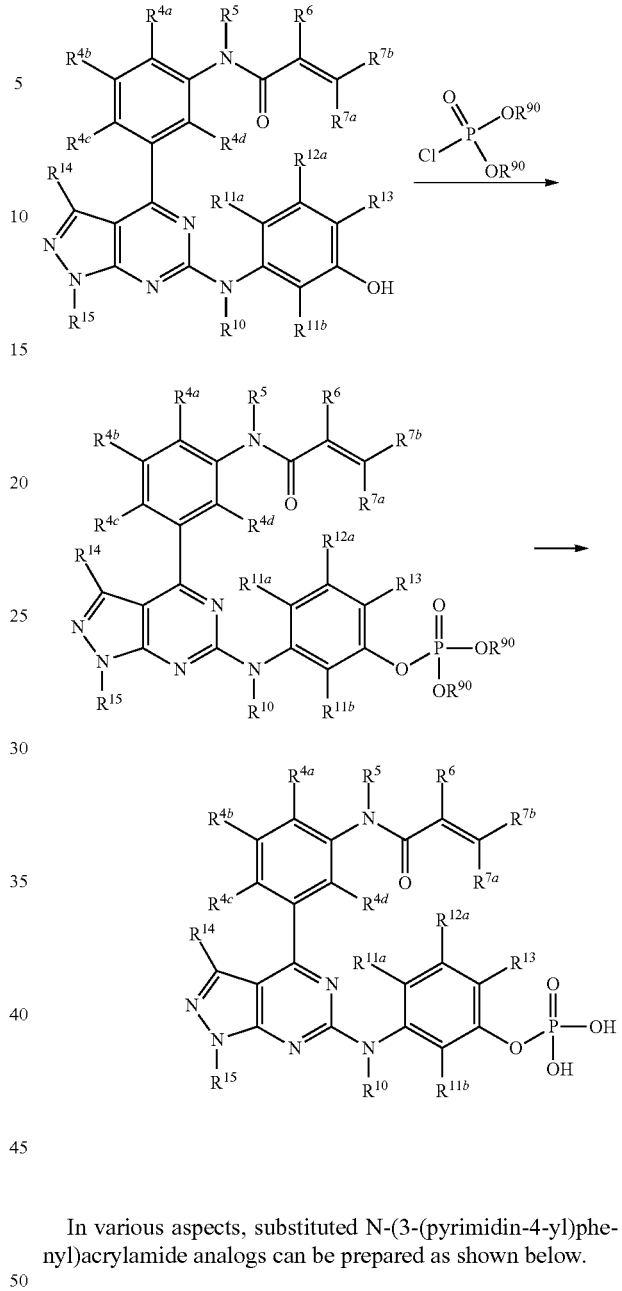

In various aspects, substituted N-(3-(pyrimidin-4-yl)phenyl)acrylamide analogs can be prepared as shown below.

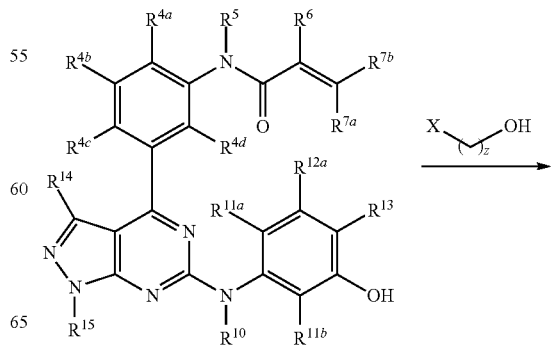

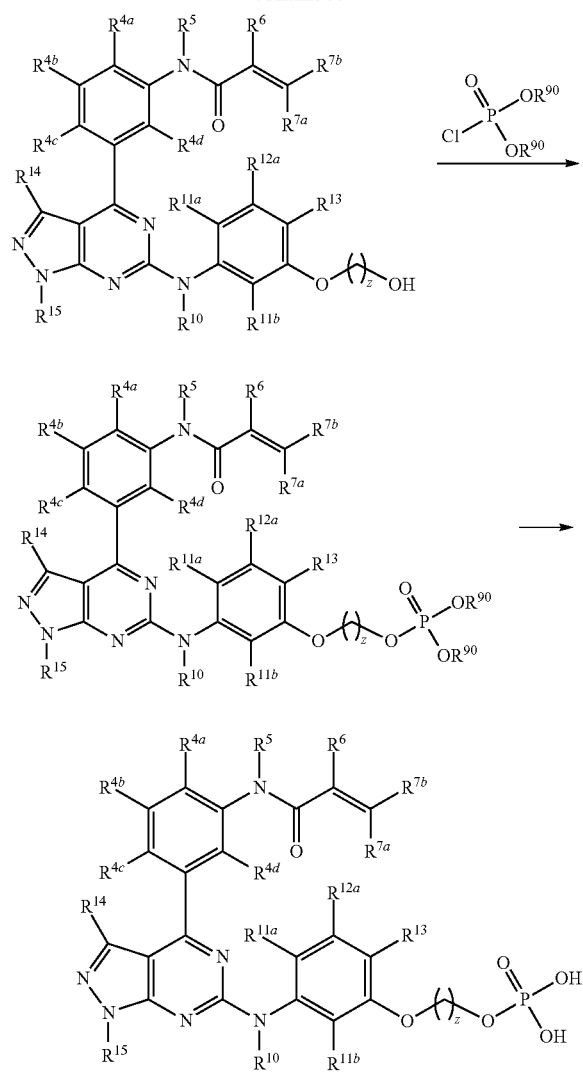
X: halogen
In various aspects, substituted N-(3-(pyrimidin-4-yl)phenyl)acrylamide analogs can be prepared as shown below.
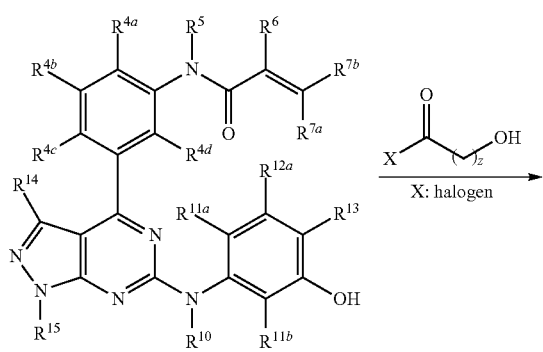
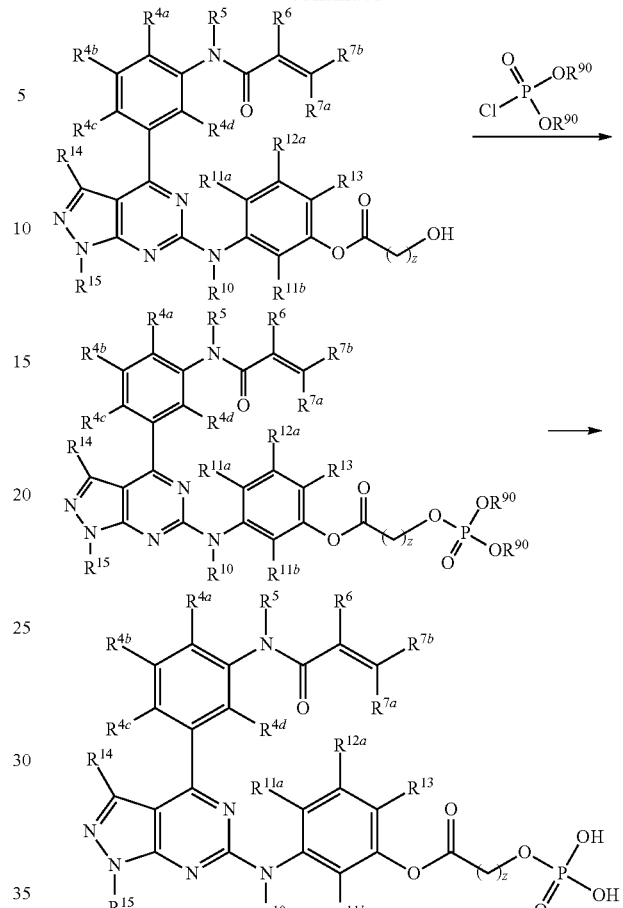
Compounds are represented in generic form, with substituents as noted in compound descriptions elsewhere herein. More specific examples are set forth below.
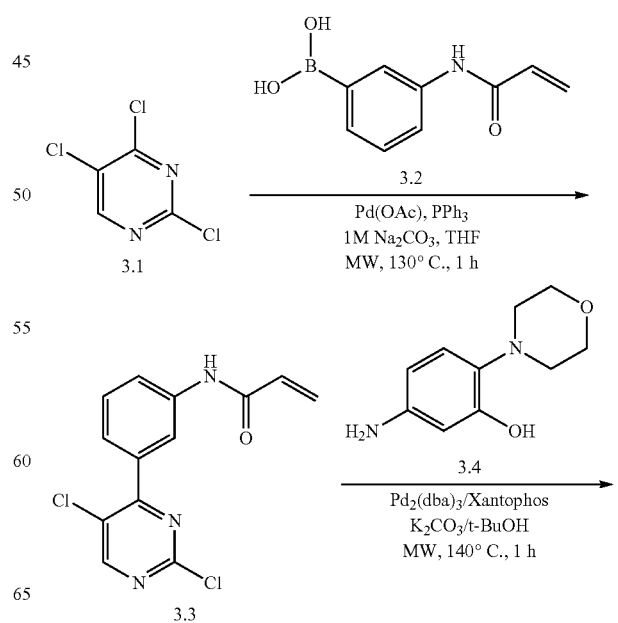

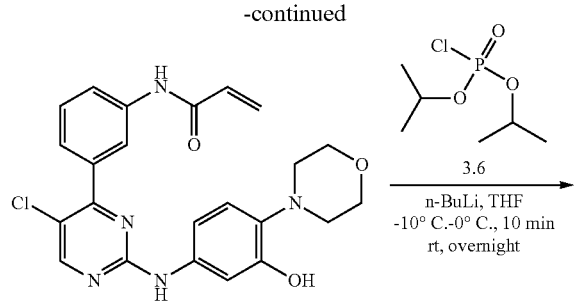
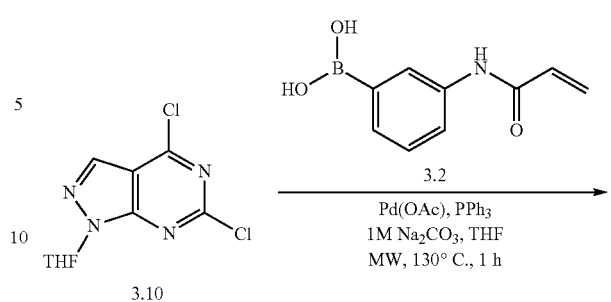
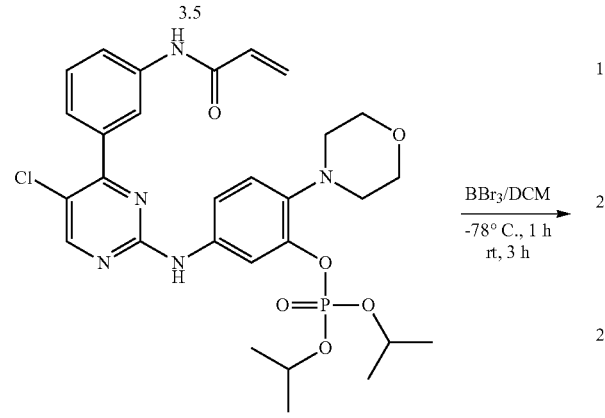
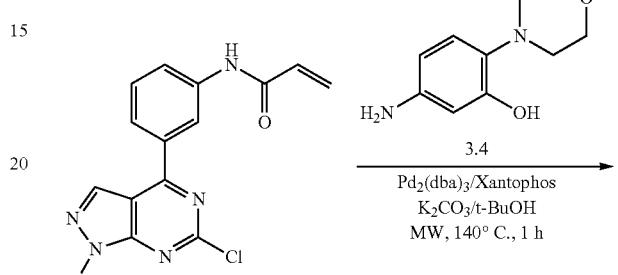
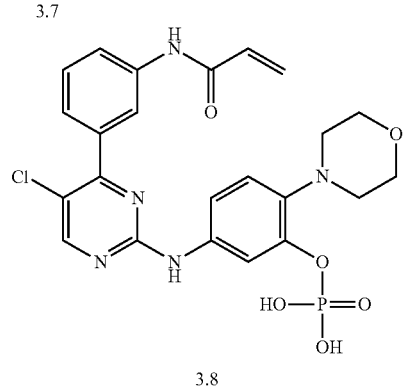
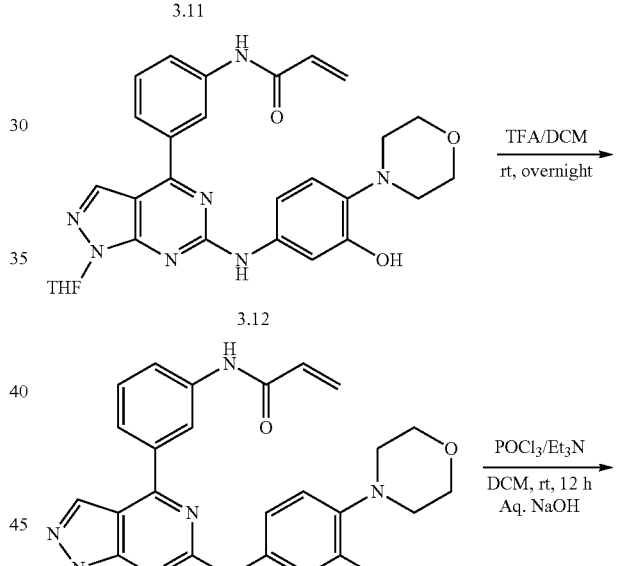
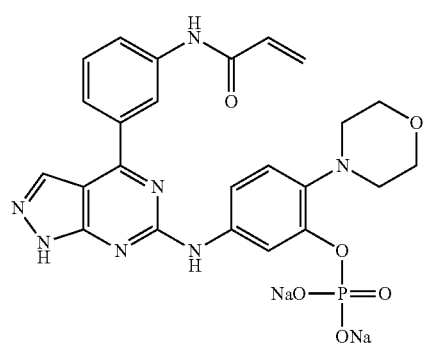

The phosphate compound of type (3.8) can be prepared as described in the reaction herein above. For example, beginning with a suitable trihalopyrimidine of type (3.1), a palladium catalyzed coupling reaction with a compound of type (3.2) under mild conditions is carried to provide a compound of type (3.3). Reaction of this product with a compound of type (3.4) under palladium catalyzed aminolysis conditions can yield the desired product, a compound of type (3.5). The hydroxyl moiety of the morpholinophenyl group is modified with a suitable alkyl phosphorohalidate, e.g. a compound of type (3.6) such as diisopropyl phosphorochloridate, under suitable reaction conditions as indicated in the reaction scheme, although variations are possible and can be required depending upon the specific reactants involved. Such variations of reaction conditions are within the skill of one skilled in the art. The reaction provides a compound of type (3.7). Such compounds can be dealkylated as appropriate, and dealkylation can be accomplished using reaction conditions such as those described in the reaction scheme, although variations are possible and can be required depending upon the specific reactants involved. Such variations of reaction conditions are within the skill of one skilled in the art.

Alternatively, compounds of type (3.14) can be prepared as shown in the reaction scheme herein above. The initial steps from a compound of type (3.10) to a compound of type (3.13) are similar to those previously described herein. A phosphate group can be introduced at the hydroxyl moiety of the morpholinophenyl group as shown above using phosphoryl chloride as an alternative to a dialkyl phosphorohalidate as described previously. Appropriate reaction conditions are as shown, although variations are possible and can be required depending upon the specific reactants involved. Such variations of reaction conditions are within the skill of one skilled in the art.

In a further aspect, the compound produced exhibits inhibition of the BCR signaling pathway. In a still further aspect, the compound produced exhibits inhibition of cell viability.

In a further aspect, the compound produced exhibits inhibition of a protein kinase. In a still further aspect, the protein kinase is a member of the Tec family of tyrosine protein kinases. In yet further aspect, the protein kinase is selected from tyrosine-protein kinase ITK/TSK, tyrosine-protein kinase BTK, cytoplasmic tyrosine-protein kinase BMX, receptor tyrosine-protein kinase erbB-4, tyrosine-protein kinase Tec, and epidermal growth factor receptor (receptor tyrosine-protein kinase erbB-1). In an even further aspect, the protein kinase is selected from tyrosine-protein kinase ITK/TSK, tyrosine-protein kinase BTK, and cytoplasmic tyrosine-protein kinase BMX. In a still further aspect, the protein kinase is tyrosine-protein kinase BTK.

In a further aspect, the compound produced exhibits inhibition with an $IC_{50}$ of less than about $1.0 \times 10^{-4}$ M. In a still further aspect, the compound produced exhibits inhibition with an $IC_{50}$ of less than about $1.0 \times 10^{-5}$ M. In a yet further aspect, the compound produced exhibits inhibition with an $IC_{50}$ of less than about $1.0 \times 10^{-6}$ M. In an even further aspect, the compound produced exhibits inhibition with an $IC_{50}$ of less than about $1.0 \times 10^{-7}$ M. In a still further aspect, the compound produced exhibits inhibition with an $IC_{50}$ of less than about $1.0 \times 10^{-8}$ M. In a yet further aspect, the compound produced exhibits inhibition with an $IC_{50}$ of less than about $1.0 \times 10^{-9}$ M.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, a pharmaceutical composition can comprise a pharmaceutically acceptable carrier and an effective amount of a compound represented by a formula:

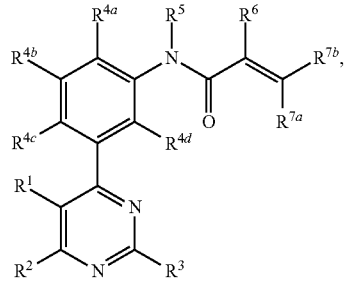

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

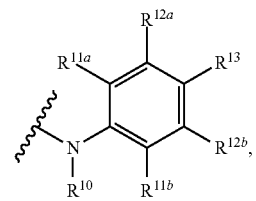

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

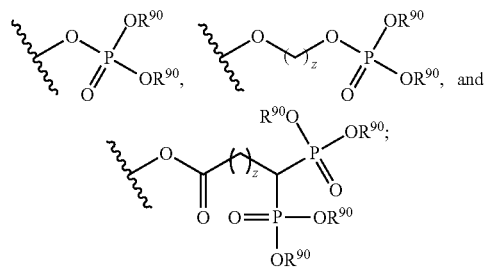

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders of uncontrolled cellular proliferation. In one aspect, the disorder of uncontrolled cellular proliferation is associated with a protein kinase dysfunction. In a further aspect, the protein kinase dysfunction is dysregulation of the BTK.

Examples of disorders associated with such a dysfunction include cancers such as leukemias, lymphomas, and solid tumors. In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer.

A. Treatment of a Disorder of Uncontrolled Cellular Proliferation

In one aspect, the invention relates to a method for the treatment of a disorder of uncontrolled cellular proliferation in a mammal, the method comprising the step of administering to the mammal an effective amount of least one compound having a structure represented by a formula:

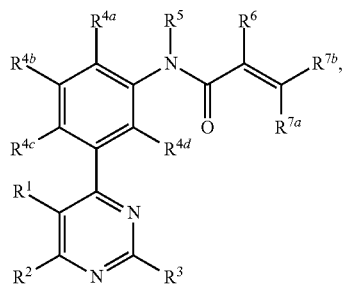

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

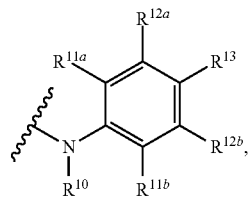

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

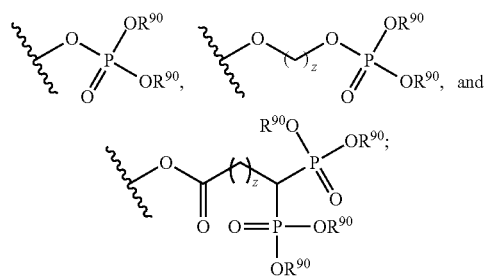

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is associated with a protein kinase dysfunction. In a still further aspect, the disorder of uncontrolled cellular proliferation is a cancer. In a yet further aspect, the cancer is a leukemia. In an even further aspect, the cancer is a lymphoma. In a further aspect, the cancer is selected from chronic lymphocytic leukemia, small lymphocytic lymphoma, B-cell non-Hodgkin lymphoma, and large B-cell lymphoma. In a yet further aspect, the cancer is a solid tumor. In a still further aspect, the cancer is selected from cancers of the blood, brain, genitourinary tract, gastrointestinal tract, colon, rectum, breast, kidney, lymphatic system, stomach, lung, pancreas, and skin. In an even further aspect, the cancer is selected from prostate cancer, glioblastoma multiforme, endometrial cancer, breast cancer, and colon cancer.

B. Treatment of a Disorder of Inflammation

In one aspect, the invention relates to a method for the treatment of an inflammatory disorder in a mammal, the method comprising the step of administering to the mammal an effective amount of least one compound having a structure represented by a formula:

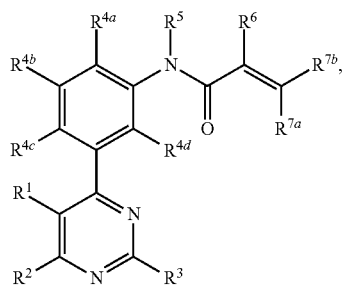

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

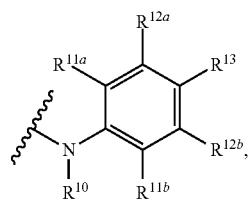

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

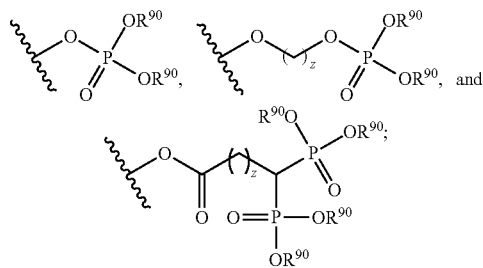

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, the mammal is a human. In further aspect, the method further comprises the step of identifying a mammal in need of treatment of a disorder of inflammation. In a still further aspect, the mammal has been diagnosed with a need for treatment of an inflammation disorder prior to the administering step.

In a further aspect, the inflammatory disorder is associated with a protein kinase dysfunction. In a further aspect, the inflammatory disorder is an autoimmune disorder. In a further aspect, the inflammatory disorder is an arthritic disease. In a further aspect, the arthritic disease is selected from inflammatory arthritis, osteoarthritis, lymphocyte-independent arthritis, and rheumatoid arthritis.

C. Decreasing Kinase Activity

In one aspect, the invention relates to a method for decreasing kinase activity in a mammal, the method comprising the step of administering to the mammal an effective amount of at least one compound having a structure represented by a formula:

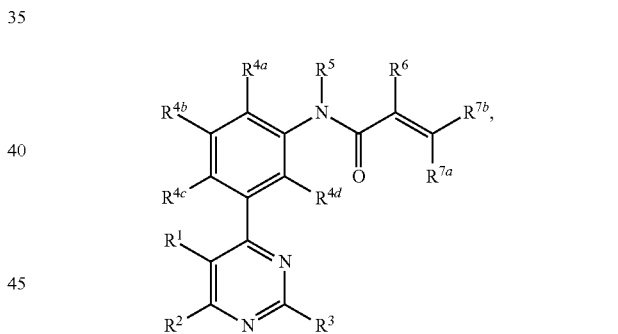

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

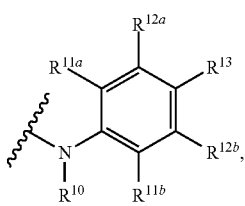

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

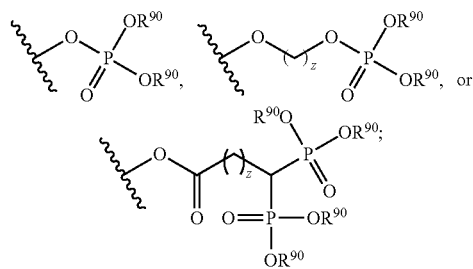

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of decreasing kinase activity. In a still further aspect, the mammal has been diagnosed with a need for decreasing kinase activity prior to the administering step.

In a further aspect, the need for decreasing kinase activity is associated with treatment of a disorder of uncontrolled cellular proliferation. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the blood, brain, genitourinary tract, gastrointestinal tract, colon, rectum, breast, kidney, lymphatic system, stomach, lung, pancreas, and skin. In an even further aspect, the cancer is selected from prostate cancer, glioblastoma multiforme, endometrial cancer, breast cancer, and colon cancer.

In a further aspect, the need for decreasing kinase activity is associated with treatment of an inflammation disorder. In a further aspect, the inflammatory disorder is associated with a protein kinase dysfunction. In a further aspect, the inflammatory disorder is an autoimmune disorder. In a further aspect, the inflammatory disorder is an arthritic disease. In a further aspect, the arthritic disease is selected from inflammatory arthritis, osteoarthritis, lymphocyte-independent arthritis, and rheumatoid arthritis.

D. Decreasing Kinase Activity in Cells

In one aspect, the invention relates to a method for decreasing kinase activity in at least one cell, the method comprising the step of contacting the at least one cell with an effective amount of least one compound having a structure represented by a formula:

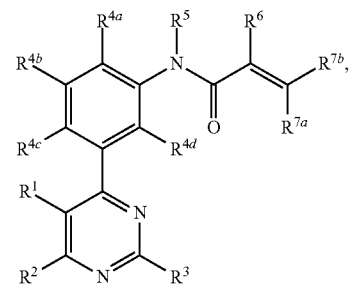

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

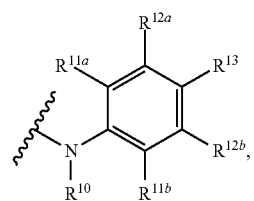

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

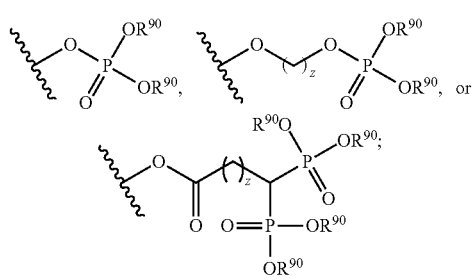

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In a further aspect, the compound is a disclosed compound or a product of a disclosed method of making a compound. In a still further aspect, the effective amount is a therapeutically effective amount. In a yet still further aspect, the effective amount is a prophylactically effective amount.

In a further aspect, the cell is mammalian. In a still further aspect, the cell is human. In a yet further aspect, contacting is via administration to a mammal. In a further aspect, the method further comprises the step of identifying the mammal as having a need of decreasing kinase activity in a cell. In a still further aspect, the mammal has been diagnosed with a need for decreasing kinase activity prior to the administering step.

In a further aspect, the need for decreasing kinase activity in a cell is associated with a disorder of uncontrolled cellular. In a still further aspect, the disorder of uncontrolled cellular proliferation is a cancer. In a yet further aspect, the cancer is a leukemia. In an even further aspect, the cancer is a lymphoma. In a still further aspect, the cancer is a solid tumor. In a yet further aspect, the cancer is selected from cancers of the blood, brain, genitourinary tract, gastrointestinal tract, colon, rectum, breast, kidney, lymphatic system, stomach, lung, pancreas, and skin. In an even further aspect, the cancer is selected from prostate cancer, glioblastoma multiforme, endometrial cancer, breast cancer, and colon cancer.

In a further aspect, the need for decreasing kinase activity in a cell is associated with treatment of an inflammation disorder. In a further aspect, the inflammatory disorder is associated with a protein kinase dysfunction. In a further aspect, the inflammatory disorder is an autoimmune disorder. In a further aspect, the inflammatory disorder is an arthritic disease. In a further aspect, the arthritic disease is selected from inflammatory arthritis, osteoarthritis, lymphocyte-independent arthritis, and rheumatoid arthritis.

2. Manufacture of a Medicament

In one aspect, the invention relates to a method for the manufacture of a medicament for inhibition of BTK in a mammal comprising combining a therapeutically effective amount of a disclosed compound or product of a disclosed method with a pharmaceutically acceptable carrier or diluent.

3. Use of Compounds

In one aspect, the invention relates to the use of a compound having a structure represented by a formula:

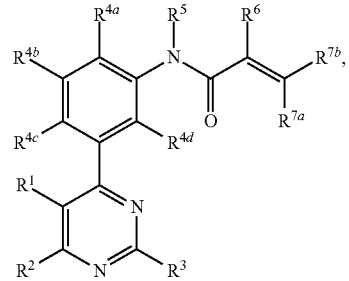

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

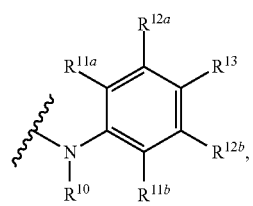

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

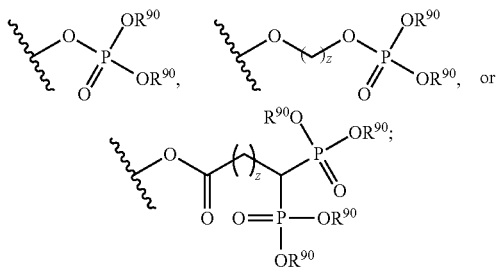

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

In a further aspect, the compound is a disclosed compound or a product of a disclosed method of making a compound. In a further aspect, the mammal is a human. In a further aspect, the need for decreasing kinase activity is associated with treatment of a disorder of uncontrolled cellular proliferation. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the blood, brain, genitourinary tract, gastrointestinal tract, colon, rectum, breast, kidney, lymphatic system, stomach, lung, pancreas, and skin. In an even further aspect, the cancer is selected from prostate cancer, glioblastoma multiforme, endometrial cancer, breast cancer, and colon cancer.

In a further aspect, the need for decreasing kinase activity is associated with treatment of an inflammation disorder. In a further aspect, the inflammatory disorder is associated with a protein kinase dysfunction. In a further aspect, the inflammatory disorder is an autoimmune disorder. In a further aspect, the inflammatory disorder is an arthritic disease. In a further aspect, the arthritic disease is selected from inflammatory arthritis, osteoarthritis, lymphocyte-independent arthritis, and rheumatoid arthritis.

4. Kits

In one aspect, the invention relates to a kit comprising at least one compound having a structure represented by a formula:

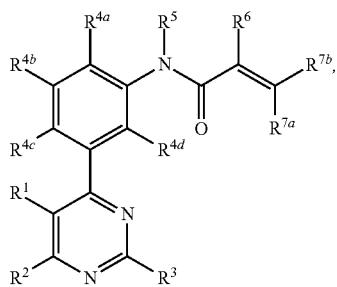

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

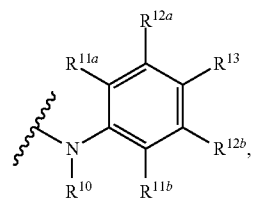

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

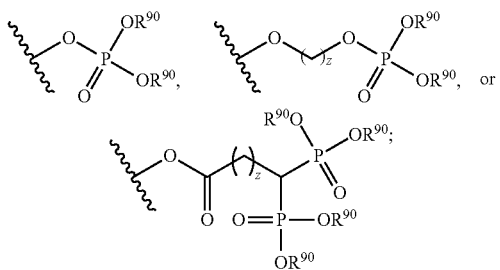

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof, and one or more of:

(a) at least one agent known to increase kinase activity;
(b) at least one agent known to decrease kinase activity;
(c) at least one agent known to treat a disorder of uncontrolled cellular proliferation; or
(d) instructions for treating a disorder associated with uncontrolled cellular proliferation.

In a further aspect, the compound is a disclosed compound or a product of a disclosed method of making a compound. In a further aspect, the mammal is a human.

In a further aspect, the disorder of uncontrolled cellular proliferation is associated with a kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the blood, brain, genitourinary tract, gastrointestinal tract, colon, rectum, breast, kidney, lymphatic system, stomach, lung, pancreas, and skin. In an even further aspect, the cancer is selected from prostate cancer, glioblastoma multiforme, endometrial cancer, breast cancer, and colon cancer.

In a further aspect, the need for decreasing kinase activity is associated with treatment of an inflammation disorder. In a further aspect, the inflammatory disorder is associated with a protein kinase dysfunction. In a further aspect, the inflammatory disorder is an autoimmune disorder. In a further aspect, the inflammatory disorder is an arthritic disease. In a further aspect, the arthritic disease is selected from inflammatory arthritis, osteoarthritis, lymphocyte-independent arthritis, and rheumatoid arthritis.

In a further aspect, the at least one compound or the at least one product and the at least one agent are co-formulated. In a further aspect, the at least one compound or the at least one product and the at least one agent are co-packaged.

In a further aspect, the at least one agent is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent. In a yet further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In a yet further aspect, the mitotic inhibitor agent is selected from one or more of the group consisting of irinotecan, topotecan, rubitecan, cabazitaxel, docetaxel, paclitaxel, etoposide, vincristine, ixabepilone, vinorelbine, vinblastine, and teniposide, or a pharmaceutically acceptable salt, hydrate, solvate, or polymorph thereof. In an even further aspect, the mTor inhibitor agent is selected from one or more of the group consisting of everolimus, siroliumus, and temsirolimus, or a pharmaceutically acceptable salt, hydrate, solvate, or polymorph thereof.

5. Non-Medical Uses

Also provided are the uses of the disclosed compounds and products as pharmacological tools in the development and standardization of in vitro and in vivo test systems for the evaluation of the effects of inhibitors of BTK activity in laboratory animals such as cats, dogs, rabbits, monkeys, rats and mice, as part of the search for new therapeutic agents that inhibit BTK.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods

All routine reagents and solvents were purchased from Sigma Aldrich and used as received. They were of reagent grade, purity≥99%. Specialty chemicals and building blocks obtained from several suppliers were of the highest offered purity (always ≥95%).

NMR spectroscopy was performed on a Mercury 400 MHz operating at 400 MHz, equipped with a 5 mm broadband probe and using standard pulse sequences. Chemical shifts (δ) are reported in parts-per-million (ppm) relative to the residual solvent signals. Coupling constants (J-values) are expressed in Hz.

Mass spectrometry was performed on a Waters Quattro-II triple quadrupole mass spectrometer. All samples were analyzed by positive ESI-MS and the mass-to-charge ratio (m/z) of the protonated molecular ion is reported.

Microwave-assisted reactions were performed on a Biotage Initiator 2.5 at various powers.

Hydrogenation reactions were performed on a standard Parr hydrogenation apparatus.

Reactions were monitored by TLC on Baker flexible-backed plates coated with 200 µm of silica gel containing a fluorescent indicator. Preparative TLC was performed on 20 cm×20 cm Analtech Uniplates coated with a 1000 or 2000 µm silica gel layer containing a fluorescent (UV 254) indicator. Elution mixtures are reported as v:v. Spot visualization was achieved using UV light.

Flash chromatography was performed on a Teledyne Isco CombiFlash® RF 200 using appropriately sized Redisep Rf Gold® or Standard normal-phase silica or reversed-phase C-18 columns. Crude compounds were adsorbed on silica gel, 70-230 mesh 40 Å (for normal phase) or Celite 503 (for reversed-phase) and loaded into solid cartridges. Elution mixtures are reported as v:v.

2. Preparation of N-(3-(2,5-Dichloropyrimidin-4-Yl)Phenyl)Acrylamide

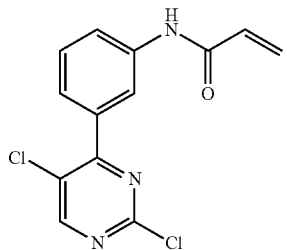 [SMILES: C=CC(=O)Nc1cccc(-c2nc(Cl)ncc2Cl)c1]

5-bromo-2,4-dichloropyrimidine (200 mg, 1.090 mmol), (3-acrylamidophenyl)boronic acid (188 mg, 0.984 mmol) and triphenylphosphine (12 mg, 0.046 mmol) were dissolved in a mixture of toluene (10 mL) and potassium carbonate (165 mg, 1.194 mmol), after which palladium(II) acetate (4.8 mg, 0.021 mmol) was added. The reaction mixture was allowed to stir overnight at 40° C. The reaction was monitored by TLC, and after completion of the reaction the solvent was removed in vacuo. The crude material was purified by flash chromatography (EtOAc/Hexane 20%) to give the title compound. $^1$H NMR (400 MHz, CDCl$_3$): δ 8.58 (s, 1H), 8.07 (s, 1H), 7.79 (d, 1H, J=8.0 Hz), 7.56 (m, 1H), 7.39 9t, 1H, J=8.4 Hz), 6.38 (m, 1H), 6.29-6.22 (m, 1H), 5.70 (d, 1H, J=10.0 Hz). ESI-MS: m/z 294.0 [M+H]$^+$.

3. Preparation of 4,6-Dichloro-1-(Tetrahydro-2H-Pyran-2-Yl)-1H-Pyrazolo[3,4-D]Pyrimidine

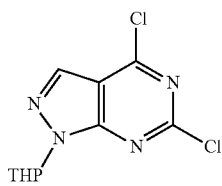

pTsOH (30.2 mg, 0.159 mmol) was added to a solution of 4,6-dichloro-1H-pyrazolo[3,4-d]pyrimidine (300 mg, 1.587 mmol) and 3,4-dihydro-2H-pyran (200 mg, 2.381 mmol) in a mixture of tetrahydrofuran (ratio: 1.000, volume: 5 ml) and CH$_2$Cl$_2$ (ratio: 1.000, volume: 5 ml). The reaction mixture was stirred for 12 h at room temperature after which the solvent was removed in vacuo. The residue was taken in CH$_2$Cl$_2$ (20 mL) and poured into water (20 ml). The organic phase was separated, the aqueous phase was extracted with CH$_2$Cl$_2$ (20 mL), and the organic phases were combined. The combined organic phases were washed with water (40 mL), washed with brine (40 mL), dried over Na$_2$SO$_4$ and then concentrated. The resulting crude material was purified by flash chromatography (CH$_2$Cl$_2$/MeOH 99/1 increasing) to yield the title compound (397 mg, 1.454 mmol, 92% yield) as a pale white oil. $^1$H NMR (400 MHz, CDCl$_3$): δ 8.19 (s, 1H), 5.99 (dd, 1H, J=2.4 & 10.4 Hz), 4.12 (m, 1H), 3.79 (m, 1H), 2.53 (m, 1H), 2.13 (m, 1H), 1.93 (m, 1H), 1.76 (m, 2H), 1.64 (m, 1H). ESI-MS: 273.0 [M+H]$^+$.

4. Preparation of 2-Morpholino-5-Nitrophenol

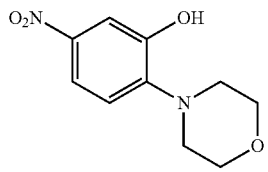 [SMILES: O=[N+]([O-])c1ccc(N2CCOCC2)c(O)c1]

Morpholine (59.9 mg, 0.688 mmol) was added to a solution of 2-bromo-5-nitrophenol (100 mg, 0.459 mmol) and triethylamine (0.070 ml, 0.505 mmol) in NMP. The reaction mixture was heated via microwave irradiation to 200° C. for 1 h. The reaction was monitored by TLC. After completion of the reaction and following cooling, the solvent was removed in vacuo and the resulting crude material was purified by flash column chromatography (2% CH$_3$OH/CH$_2$Cl$_2$) to provide the title compound as a solid. 1H NMR: (CDCl3, 400 MHz): δ 7.82-7.79 (m, 2H), 7.20 (m, 1H), 6.69 (bs, 1H), 3.89 (m, 4H), 2.95 (m, 4H). ESI-MS: 225.1 [M+H]$^+$.

5. Preparation of 5-Amino-2-Morpholinophenol

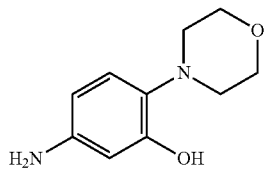

10% Palladium on carbon (10 mg, 0.892 mmol) was added to 2-morpholino-5-nitrophenol (prepared as described herein above; 200 mg, 0.892 mmol) in ethanol (20 mL), hydrogen gas was added (40 psi), and the reaction allowed to proceed for 12 h at room temperature. The reaction was monitored by TLC. After completion of the reaction, the reaction mixture filtered through Celite®, and the solvent removed in vacuo. The residue was purified by flash column chromatography (2% CH$_3$OH/CH$_2$Cl$_2$) to provide the title compound 5-amino-2-morpholinophenol (200 mg, 0.937 mmol, 105% yield) as a solid.

6. Preparation of N-(3-(6-Chloro-1-(Tetrahydro-2H-Pyran-2-Yl)-1H-Pyrazolo[3,4-D]Pyrimidin-4-Yl) Phenyl)Acrylamide

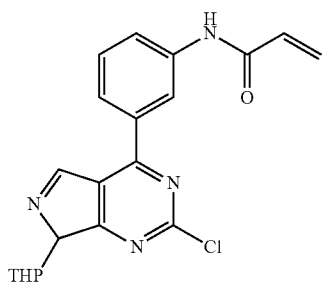

4,6-dichloro-1-(tetrahydro-2H-pyran-2-yl)-1H-pyrazolo[3,4-d]pyrimidine (100 mg, 0.366 mmol), (3-acrylamidophenyl)boronic acid (70 mg, 0.366 mmol) and triphenylphosphine (4 mg, 0.015 mmol) were dissolved in a mixture of toluene (7 mL) and 1 M sodium carbonate (39 mg, 0.367 mmol). Palladium(II) acetate (2.0 mg, 0.009 mmol) was then added and the reaction mixture was stirred for 12 h at 80° C. The reaction mixture was then allowed to cool to room temperature and the solvent was removed in vacuo. The residue was dissolved in EtOAc (20 mL) and washed with water (10 mL). The organic layer was separated, the aqueous layer was extracted with EtOAc (20 ml), and organic layers were combined. The combined organic layers were washed with brine (20 mL), dried over Na$_2$SO$_4$ and then concentrated. The crude material was purified by flash chromatography (EtOAc/hexane 20%) to yield the title compound (70%). $^1$H NMR (400 MHz, CDCl$_3$): δ 8.45 (m, 2H), 7.88 (d, 1H, J=8.0 Hz), 7.85 (d, 1H, J=8.0 Hz), 7.68 (s, 1H), 7.49 (t, 1H, J=8.0 Hz), 6.46 (m, 1H), 6.27 (m, 1H), 6.06 (d, 1H, J=10.4 Hz), 5.79 (d, 1H, J=10.0 Hz), 4.12 (m, 1H), 3.82 (t, 1H, J=10.0 Hz), 2.58 (m, 1H), 2.14 (m, 1H), 1.95 (m, 1H), 1.78 (m, 2H), 1.62 (m, 1H). ESI-MS: 384.10 [M+H]$^+$.

7. Preparation of N-(3-(6-((3-Hydroxy-4-Morpholinophenyl)Amino)-1-(Tetrahydro-2H-Pyran-2-Yl)-1H-Pyrazolo[3,4-D]Pyrimidin-4-Yl)Phenyl)Acrylamide

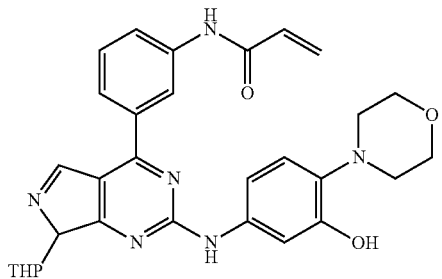

N-(3-(6-chloro-1-(tetrahydro-2H-pyran-2-yl)-1H-pyrazolo[3,4-d]pyrimidin-4-yl)phenyl)acrylamide (50 mg, 0.130 mmol), 5-amino-2-morpholinophenol (25.3 mg, 0.130 mmol) and potassium carbonate (45.0 mg, 0.326 mmol) were dissolved in t-BuOH (80 mL). 4,5-Bis(diphenylphosphino)-9,9-dimethylxanthene (3.01 mg, 5.21 μmol) and Pd$_2$dba$_3$ (2.386 mg, 2.61 μmol) were then added to the solution. The reaction mixture was refluxed at 100° C. for 12 h, and the reaction was monitored by TLC. Following completion of the reaction, the reaction mixture was allowed to cool, and the solvent was removed in vacuo. The resulting crude material was purified by flash chromatography (2% methanol/DCM) to yield the title compound (20 mg, 0.037 mmol, 28.3% yield) as yellow solid. Crude material was used without further purification and used directly in the next reaction.

8. Preparation of N-(3-(6-((3-Hydroxy-4-Morpholinophenyl)Amino)-1H-Pyrazolo[3,4-d]Pyrimidin-4-Yl)Phenyl)Acrylamide

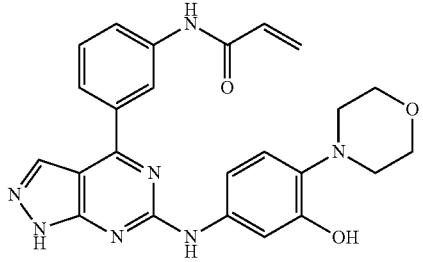 [SMILES: C=CC(=O)Nc1cccc(-c2nc(Nc3ccc(N4CCOCC4)c(O)c3)nc3[nH]ncc23)c1]

2,2,2-trifluoroacetic acid (526 mg, 4.62 mmol) was added to a solution of N-(3-(6-((3-hydroxy-4-morpholinophenyl)amino)-1-(tetrahydro-2H-pyran-2-yl)-1H-pyrazolo[3,4-d]pyrimidin-4-yl)phenyl)acrylamide (100 mg, 0.185 mmol) in DCM (10 ml). The reaction mixture was stirred at room temperature overnight (about 8-12 h), after which the solvent was removed in vacuo. The residue was purified by flash chromatography (MeOH/DCM 5%) to yield the title compound (45 mg, 0.096 mmol, 52.2% yield) as a solid. $^1$NMR (CD3OD, 400 MHz): 8.98 (s, 1H), 8.39 (s, 1H), 8.05 (d, 1H, J=7.2 Hz), 7.94 (s, 1H), 7.62 (d, 1H, J=8.4 Hz), 7.56 (t, 1H, J=8.0 Hz), 7.36-7.29 (m, 2H), 6.54-6.43 (m, 2H), 5.85 (dd, 1H, J=2.8 & 9.6 Hz), 4.03 (m, 4H), 3.54 (m, 4H).

9. Preparation of N-(3-(5-Chloro-2-((3-Hydroxy-4-Morpholinophenyl)Amino)Pyrimidin-4-Yl)Phenyl)Acrylamide

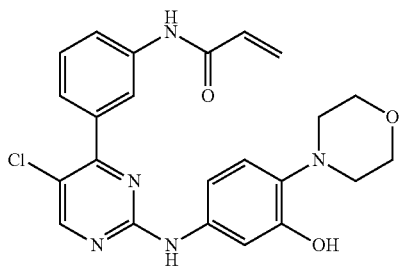 [SMILES: C=CC(=O)Nc1cccc(-c2nc(Nc3ccc(N4CCOCC4)c(O)c3)ncc2Cl)c1]

N-(3-(2,5-dichloropyrimidin-4-yl)phenyl)acrylamide (151 mg, 0.515 mmol), 5-amino-2-morpholinophenol (100 mg, 0.515 mmol) and potassium carbonate (178 mg, 1.287 mmol) were dissolved in t-BuOH (5 mL) and Pd$_2$dba$_3$ (9.43 mg, 10.30 μmol) and 4,5-bis(diphenylphosphino)-9,9-dimethylxanthene (11.92 mg, 0.021 mmol) were added and then the reaction mixture was heated via microwave irradiation to 140° C. for 1 h. Reaction was monitored by TLC. After completion of the reaction, it was allowed to cool to about room temperature, and then reaction mixture was extracted with ethyl acetate (2×50 mL). The organic phase was concentrated and the residue was purified by flash column chromatography (4% MeOH/DCM) to provide the title compound (120 mg, 50.0% yield) as an off white solid. 1HNMR (400 MHz, CD$_3$OD): δ 8.43 (s, 1H), 8.36 (s, 1H), 7.68 (m, 2H), 7.53 (d, 1H, J=2.0 Hz), 7.46 (t, 1H, J=8.4 Hz), 7.02 (dd, 1H, J=2.4 & 8.8 Hz), 6.97 (d, 1H, J=8.4 Hz), 6.50-6.38 (m, 2H), 5.80 (dd, 1H, J=2.4 & 9.6 Hz), 3.83 (m, 4H), 2.93 (m, 4H). Mass: 452.1 [M+H]$^+$.

10. Preparation of 5-((4-(3-Acrylamidophenyl)-5-Chloropyrimidin-2-Yl)Amino)-2-Morpholinophenyl Diisopropyl Phosphate

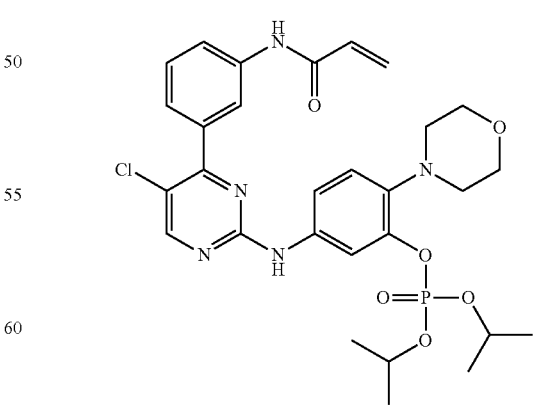

n-Butyl lithium (0.14 mL, 2.5 M solution in hexane) was diluted 10-fold in THF (1.4 mL), and the resulting mixture added dropwise to a rapidly stirring solution of N-(3-(5- chloro-2-((3-hydroxy-4-morpholinophenyl)amino)pyrimidin-4-yl)phenyl)acrylamide (100 mg, 0.221 mmol) in THF (5 ml) that was under argon gas and the reaction vessel was immersed in a salt-ice bath (bath temperature about −10° C. to −5° C.). The resulting white suspension was stirred for 5 min, followed by addition of diisopropyl phosphorochloridate (178 mg, 0.885 mmol) to the reaction mixture in a single portion. The suspension became a clear solution within about 5 min, and then reaction mixture was stirred at ambient temperature for about 18 h. Then reaction mixture was evaporated to dryness on a rotary evaporator. The resulting crude residue was purified by silica gel flash chromatography using a mixture of 3% methanol and DCM as eluting solvent to provide the title compound (50 mg, 0.078 mmol, 35.2% yield) as a syrup. 1HNMR (400 MHz, CDCl$_3$): δ 8.52 (bs, 1H), 8.49 (d, 1H, J=8.0 Hz), 8.37 (s, 1H), 7.98 (s, 1H), 7.78 (d, 1H, J=8.0 Hz), 7.41 (d, 1H, J=8.4 Hz), 7.38 (s, 1H), 6.96 (d, 1H, J=8.4 Hz), 6.77 (d, 1H, J=8.0 Hz), 6.45 (m, 2H), 5.68 (t, 1H, J=6.0 Hz), 4.74 (m, 2H), 3.81 (m, 4H), 2.96 (m, 4H). Mass: 616.2 [M+H]$^+$.

11. Characterization of Exemplary Compounds

Substituted N-(3-(pyrimidin-4-yl)phenyl)acrylamide analogs were synthesized with methods identical or analogous to those as described herein above. The requisite starting materials were commercially available, described in the literature, or readily synthesized by one skilled in the art of organic synthesis.

are as indicated in the table below. ATCC is the American Type Culture Collection (Manassas, Va.), and DSMZ is the Deutsche Sammlung von Mikroorganismen and Zellkulturen GmbH (German Collection of Microorganims and Cell Cultures; Braunschweig, Germany). The cell lines typically used in these studies are indicated below in Table II.

TABLE II

| Cell Line | Tissue Source | ATCC/DSMZ Number | Culture media |
|---|---|---|---|
| BxPC-3 | Pancreas adenocarcinoma | CRL-1687 (ATCC) | RPMI-1640 |
| GRANTA-519 | High-grade B-NHL (leukemic transformation of mantle cell lymphoma, stage IV | ACC 342 (DSMZ) | Dulbecco's MEM (4.5 g/L glucose) + 2 mM L-glutamine |
| OPM-2 | Multiple myeloma (IgG lambda) in leukemic phase | ACC 50 (DSMZ) | RPMI-1640 |
| Ramos (RA-1) | Burkitt's lymphoma | CRL-1596 (ATCC) | RPMI-1640 |

13. BTK Kinase Assay: ADP Generation Assay

The primary assay for compound inhibitory activity was the ADP generation assay described herein. Test compounds were diluted to desired concentrations in kinase reaction buffer and briefly incubated with recombinant full-length

TABLE II

| No. | Structure | Name | M + H |
|---|---|---|---|
| 1 | [structure] | N-(3-(5-chloro-2-((3-hydroxy-4-morpholinophenyl)amino)pyrimidin-4-yl)phenyl)acrylamide | 452.1 |
| 2 | [structure] | 5-((4-(3-acrylamidophenyl)-5-chloropyrimidin-2-yl)amino)-2-morpholinophenyl diisopropyl phosphate | 616.2 |

12. Cell Culture

All cell lines were cultured in RPMI-1640 media supplemented with 10% fetal bovine serum ("FBS") and 1% penicillin/streptomycin (100 IU/mL penicillin and 100 μg/mL streptomycin) at 37° C. and 5% CO$_2$. Additional supplements human BTK kinase with a (His)$_6$ tag (81.3 kDa; Invitrogen Corporation, Carlsbad, Calif.). The assay as described is based on volumes used in a standard 384 well format using solid, white-wall plates. The reaction was subsequently initiated by the addition of ATP and myelin basic protein (MBP) substrate (Millipore Corporation, Waltham, Mass.). Composition of the assay reaction mixture (5 mL volume) was: 5% v/v DMSO, 60 nM BTK, 1.6 µM ATP, and 20 µM MBP substrate. After incubation at room temperature for 60 min, 5 mL of the ADP-Glo™ reagent (Promega Corporation, Madison, Wis.) was added to each well and incubated for an additional 40 minutes. The reagent stopped the kinase reaction and depleted the unconsumed ATP. Kinase Detection reagent (10 mL; Promega Corporation) was then added to each well. The Kinase Detection reagent comprises reagents to convert ADP to ATP and provide luciferase and luciferin to detect ATP. Luminescence was measured on an EnVision® microplate reader (PerkinElmer). The amount of luminescence from each reaction is directly correlated with BTK kinase activity. Percent inhibition and $IC_{50}$ values were calculated by comparing enzyme activity in drug-treated wells to the appropriate controls.

14. BTK Kinase Assay: Time Resolved-Fret Assay

Activity of compounds was routinely confirmed using a secondary assay as described herein. The secondary assay was a time resolved-FRET kinase assay. Test compound are diluted to desired concentrations in kinase reaction buffer and briefly incubated with BTK kinase (as described above; Invitrogen). The reaction is initiated by the addition of ATP and enzyme substrate, HTRF® KinEASE™-TK Substrate-biotin (Cisbio US, Bedford, Mass.). The composition of the reaction (10 µl) was: 1% v/v DMSO, 10 nM BTK, 60 µM ATP, and 1 µM substrate. After incubation at room temperature for 60 min, the enzyme reaction is stopped by EDTA-containing buffer, which also contains europium-labeled ($Eu^{3+}$-Cryptate) anti-phosphotyrosine antibody (Cisbio) and Streptavidin-XL665 (Cisbio). The europium-labeled antibody generates a time-resolved FRET signal with the Stepavidin-XL665, which binds to the biotinylated TK substrate through the streptavidin conjugate when the substrate is phosphorylated. After one hour incubation at room temperature, fluorescence was measured with excitation of 320 nm and dual emission of 615 and 665 nm on an EnVision microplate reader. Signal is expressed in terms of a TR-FRET ratio (665:615).

15. Cell Viability Assay

The cells were grown as described above, and for the assay cells were freshly harvested and then were plated in 45 mL of appropriate media (as described above) at a density of 1000 cells per well in standard solid white-walled 384-well plates. Cells were allowed to attach by incubation overnight at 37° C. and 5% $CO_2$. Test compounds were diluted to 10× concentrations in the appropriate media for the cell used (containing 3% DMSO) and 5 mL of these dilutions were appropriate wells containing the cells. Test compounds were typically tested in triplicate (i.e. a given concentration of compound was assayed in triplicate wells). The plates containing the drug-treated cells and appropriate controls were incubated for 96 hours. At the end of the incubation, 40 mL of ATP-lite (PerkinElmer, Inc., Waltham, Mass.) reagent were added to each well and luminescence signal was measured on an EnVision microplate reader.

16. $IC_{50}$ Calculation $IC_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate $IC_{50}$ values. The $IC_{50}$ values reported are the concentration of drug at which 50% inhibition was reached.

17. Activity of Substituted N-(3-(Pyrimidin-4-Yl)Phenyl)Acrylamide Analogs in BTK Activity ($IC_{50}$) was determined in the BTK assays describe herein above, i.e. either the ADP generation assay and/or the time-resolved FRET assay, and the data are shown in Table III. The compound number corresponds to the compound numbers used in Table I. In the table below, "ADP Assay" refers to the assay which measures production of ADP resulting from use of ATP by the kinase; "HTRF Assay" refers to the time resolved-FRET kinase assay described in the examples; and "n.d." means that the $IC_{50}$ was not determined in the indicated assay. Multiple values in a given column indicate the results of more than one assay for the given compound.

TABLE III

| No. | $IC_{50}$ (µM) | |
| --- | --- | --- |
|  | ADP Assay | HTRF Assay |
| 1 | 0.004 | n.d. |
| 2 | 3.580 | n.d. |

18. Prospective In Vivo Anti-Tumor Effects

The following example of the in vivo effect of the disclosed compounds are prophetic. Generally agents which inhibit the Bcr pathway, including BTK kinase inhibitors, display efficacy in preclinical models of cancer. In vivo effects of the compounds described in the preceding examples are expected to be shown in various animal models of cancer known to the skilled person, such as tumor xenograft models. These models are typically conducted in rodent, most often in mouse, but may be conducted in other animal species as is convenient to the study goals. Compounds, products, and compositions disclosed herein are expected to show in vivo effects in various animal models of cancer known to the skilled person, such as mouse tumor xenograft models.

In vivo effects of compounds can be assessed with in a mouse tumor xenograft study, one possible study protocol is described herein. Briefly, cells (2 to 5×$10^6$ in 100 mL culture media) were implanted subcutaneously in the right hind flank of athymic nu/nu nude mice (5 to 6 weeks old, 18-22 g). For test compounds of the present invention, a typical cell-line used for the tumor xenograft study would be BxPC-3. Other suitable cell-lines for these studies are GRANTA-519, OPM-2, and Ramos (RA-1) cells. The cells are cultured prior to harvesting for this protocol as described herein.

Following implantation, the tumors are allowed to grow to 100 $mm^3$ before the animals are randomized into treatment groups (e.g. vehicle, positive control and various dose levels of the test compound); the number of animals per group is typically 8-12. Day 1 of study corresponds to the day that the animals receive their first dose. The efficacy of a test compound can be determined in studies of various length dependent upon the goals of the study. Typical study periods are for 14, 21 and 28-days. The dosing frequency (e.g. whether animals are dosed with test compound daily, every other day, every third day or other frequencies) is determined for each study depending upon the toxicity and potency of the test compound. A typical study design would involve dosing daily (M-F) with the test compound with recovery on the weekend. Throughout the study, tumor volumes and body weights are measured twice a week. At the end of the study the animals are euthanized and the tumors harvested and frozen for further analysis.

For example, compounds having a structure represented by a formula:

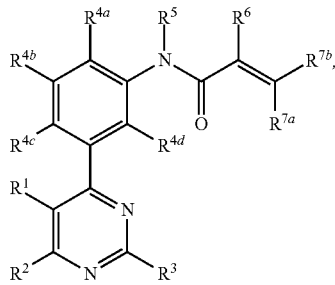

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

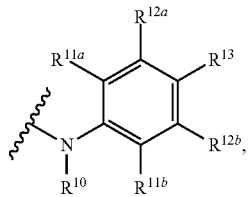

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

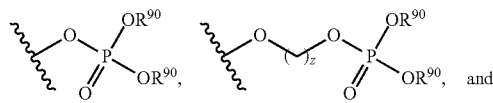

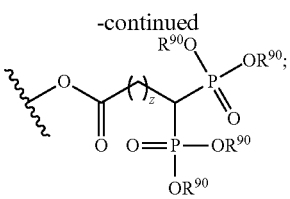

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof, are expected to show such in vivo effects as anti-tumor activity and/or increased survival in animal models of cancer.

19. Prophetic Pharmaceutical Composition Examples

"Active ingredient" as used throughout these examples relates to one or more disclosed compounds, or a product of a disclosed method of making. For example, an active ingredient is understood to include a compound having a structure represented by the formula:

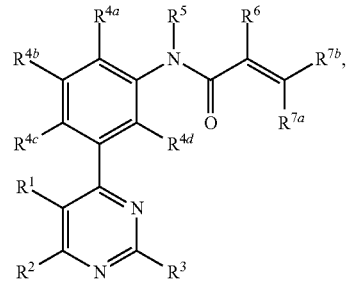

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring; wherein $R^8$ is selected from hydrogen and C1-C6 alkyl; wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino; wherein $R^9$ is selected from hydrogen and C1-C6 alkyl; wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring; wherein $R^3$ is a structure represented by the formula:

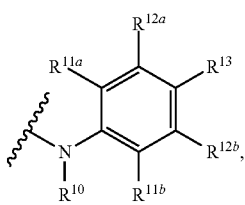

wherein $R^{10}$ is selected from hydrogen and C1-C6 alkyl; wherein each of $R^{11a}$ and $R^{11b}$ is independently selected from hydrogen, halogen, and C1-C6 alkyl; wherein $R^{12a}$ is selected from hydrogen, halogen, and C1-C6 alkyl; and wherein $R^{12b}$ is selected from hydroxyl and a group having a structure represented by a formula:

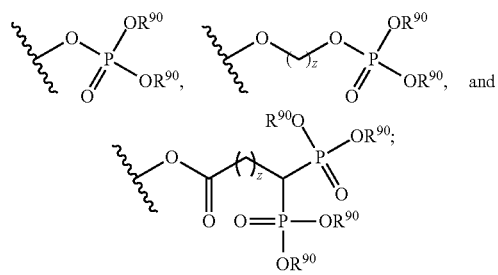

wherein z is an integer selected from 1, 2, and 3; wherein each occurrence of $R^{90}$, when present, is independently selected from hydrogen, C1-C8 alkyl, and phenyl; wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl; wherein each of $R^{4a}$, $R^{4b}$, $R^{4c}$, and $R^{4d}$ is independently selected from hydrogen, halogen, and C1-C6 alkyl; wherein $R^5$ is selected from hydrogen and C1-C6 alkyl; wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

A. Pharmaceutical Composition for Oral Administration

A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |

-continued

| Component | Amount |
|---|---|
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

B. Pharmaceutical Composition for Injectable Use

A parenteral composition can be prepared as follows:

| Component | Amount* |
|---|---|
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

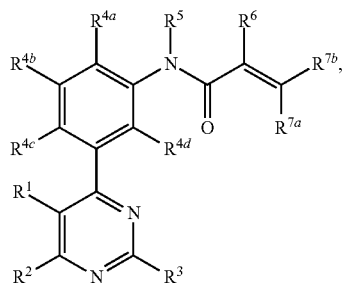

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring;

wherein $R^8$ is selected from hydrogen and C1-C6 alkyl;
wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino;
wherein $R^9$ is selected from hydrogen and C1-C6 alkyl;
wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring;
wherein $R^3$ is a structure represented by the formula:

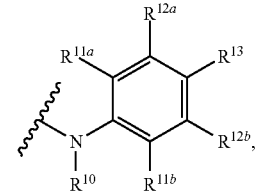

wherein $R^{10}$ is selected from hydrogen and C1-C6 alkyl;
wherein each of $R^{11a}$ and $R^{11b}$ is independently selected from hydrogen, halogen, and C1-C6 alkyl;
wherein $R^{12a}$ is selected from hydrogen, halogen, and C1-C6 alkyl; and
wherein $R^{12b}$ is selected from hydroxyl and a group having a structure represented by a formula:

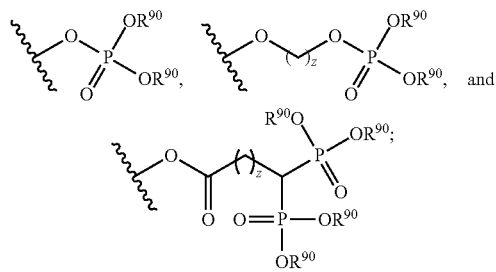

wherein z is an integer selected from 1, 2, and 3;
wherein each occurrence of $R^{90}$, when present, is independently selected from hydrogen, C1-C8 alkyl, and phenyl;
wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl;
wherein each of $R^{4a}$, $R^{4b}$, $R^{4c}$, and $R^{4d}$ is independently selected from hydrogen, halogen, and C1-C6 alkyl;
wherein $R^5$ is selected from hydrogen and C1-C6 alkyl;
wherein $R^6$ is selected from hydrogen and C1-C6 alkyl; and
wherein each of $R^{7a}$ and $R^{7b}$ is independently selected from hydrogen and C1-C6 alkyl,
or a pharmaceutically acceptable salt, solvate, or polymorph thereof.

2. The compound of claim 1, wherein $R^1$ is $NR^8Ar^1$.
3. The compound of claim 1, wherein $R^1$ is halogen.
4. The compound of claim 1, wherein $R^1$ and $R^2$ are covalently bonded and, together with the intermediate carbons, comprise an optionally substituted fused five-membered or six-membered C2-C5 heterocyclic ring.

5. The compound of claim 4, wherein the compound the heterocyclic ring is an optionally substituted pyrazole ring.

6. The compound of claim 1, wherein the compound has a structure represented by a formula:

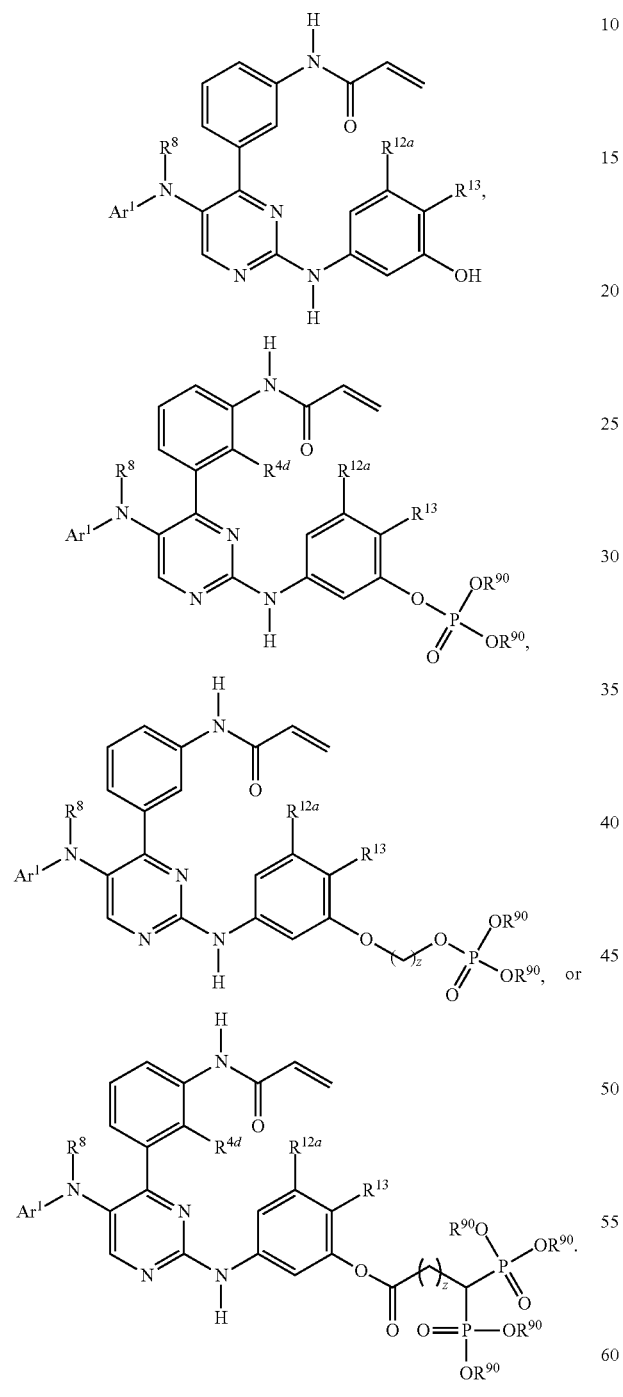

7. The compound of claim 1, wherein the compound has a structure represented by a formula:

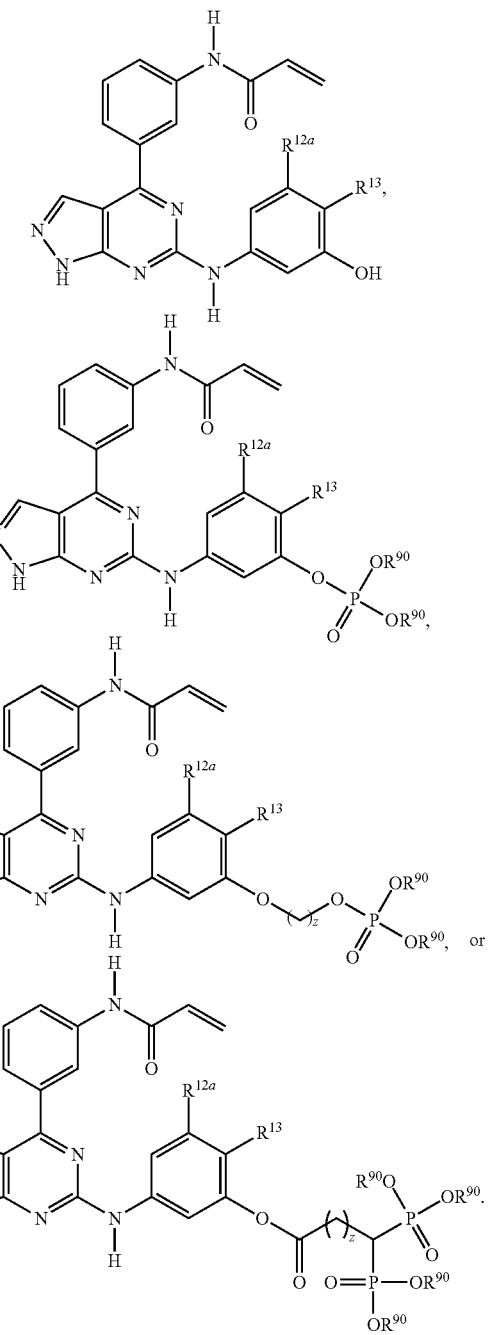

8. The compound of claim 1, wherein the compound has a structure represented by a formula:

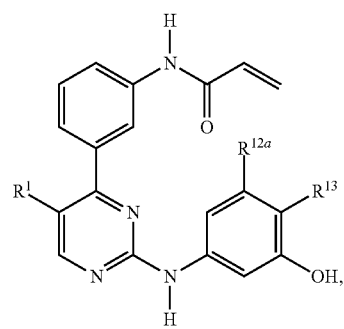

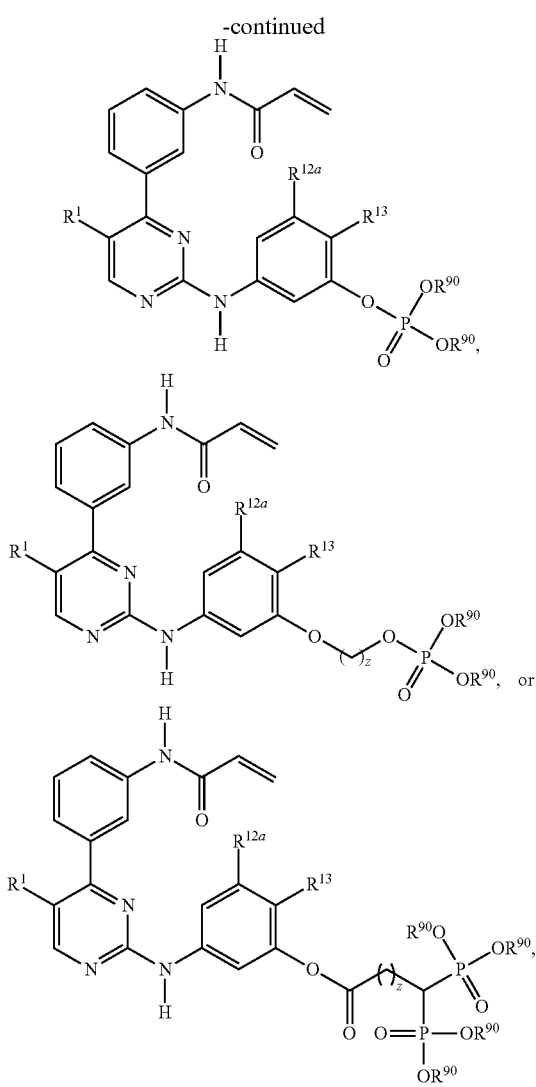

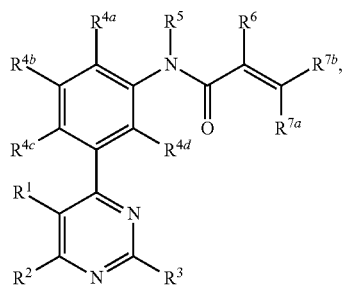

wherein R¹ is halogen.

9. A method for the treatment of cancer in a mammal, the method comprising the step of administering to the mammal an effective amount of least one compound having a structure represented by a formula:

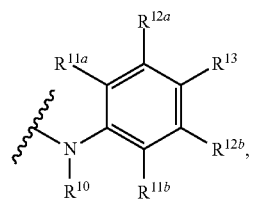

wherein R¹ is halogen or NR⁸Ar¹; or wherein R¹ and R² are optionally covalently bonded and, together with the intermediate carbons, comprise an optionally substituted fused five-membered or six-membered C2-C5 heterocyclic ring;
wherein R⁸ is selected from hydrogen and C1-C6 alkyl;
wherein Ar¹ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, SO₂R⁹, C1-C3 alkylamine, and C1-C3 dialkylamino or Ar¹ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, SO₂R⁹, C1-C3 alkylamine, and C1-C3 dialkylamino;
wherein R⁹ is selected from hydrogen and C1-C6 alkyl;
wherein R² is hydrogen; or wherein R¹ and R² are optionally covalently bonded and, together with the intermediate carbons, comprise an optionally substituted fused five-membered or six-membered C2-C5 heterocyclic ring;
wherein R³ is a structure represented by the formula:

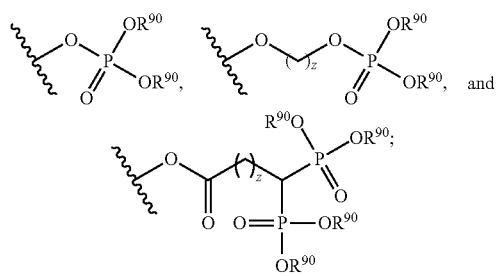

wherein R¹⁰ is selected from hydrogen and C1-C6 alkyl;
wherein each of R¹¹ᵃ and R¹¹ᵇ is independently selected from hydrogen, halogen, and C1-C6 alkyl;
wherein R¹²ᵃ is selected from hydrogen, halogen, and C1-C6 alkyl; and
wherein R¹²ᵇ is selected from hydroxyl and a group having a structure represented by a formula:

wherein z is an integer selected from 1, 2, and 3;
wherein each occurrence of R⁹⁰, when present, is independently selected from hydrogen, C1-C8 alkyl, and phenyl;
wherein R¹³ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl;
wherein each of R⁴ᵃ, R⁴ᵇ, R⁴ᶜ, and R⁴ᵈ is independently selected from hydrogen, halogen, and C1-C6 alkyl;
wherein R⁵ is selected from hydrogen and C1-C6 alkyl;
wherein R⁶ is selected from hydrogen and C1-C6 alkyl; and
wherein each of R⁷ᵃ and R⁷ᵇ is independently selected from hydrogen and C1-C6 alkyl,
or a pharmaceutically acceptable salt, solvate, or polymorph thereof.

10. The method of claim 9, further comprising the step of identifying a mammal in need of treatment of cancer.

11. The method of claim 9, wherein the mammal has been diagnosed with a need for treatment of cancer prior to the administering step.

12. The method of claim 9, wherein the cancer is selected from chronic lymphocytic leukemia, small lymphocytic lymphoma, B-cell non-Hodgkin lymphoma, and large B-cell lymphoma.

13. A method for the treatment of an arthritic disease in a mammal, the method comprising the step of administering to the mammal an effective amount of least one compound having a structure represented by a formula:

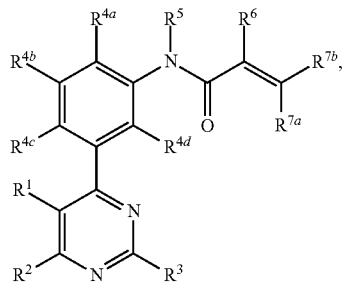

wherein $R^1$ is halogen or $NR^8Ar^1$; or wherein $R^1$ and $R^2$ are optionally covalently bonded and, together with the intermediate carbons, comprise an optionally substituted fused five-membered or six-membered C2-C5 heterocyclic ring;

wherein $R^8$ is selected from hydrogen and C1-C6 alkyl;

wherein $Ar^1$ is phenyl substituted with 0-3 groups independently selected from cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino or $Ar^1$ is monocyclic heteroaryl substituted with 0-3 groups independently selected from halo, cyano, C1-C6 alkyl, C1-C6 haloalkyoxy, C1-C6 haloalkyl, C1-C6 polyhaloalkyl, C1-C6 cyanoalkyl, $SO_2R^9$, C1-C3 alkylamine, and C1-C3 dialkylamino;

wherein $R^9$ is selected from hydrogen and C1-C6 alkyl;

wherein $R^2$ is hydrogen; or wherein $R^1$ and $R^2$ are optionally covalently bonded and, together with the intermediate carbons, comprise an optionally substituted fused five-membered or six-membered C2-C5 heterocyclic ring;

wherein $R^3$ is a structure represented by the formula:

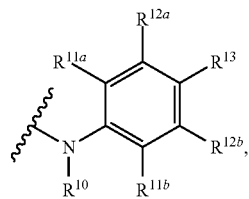

wherein $R^{10}$ is selected from hydrogen and C1-C6 alkyl;

wherein each of $R^{11a}$ and $R^{11b}$ is independently selected from hydrogen, halogen, and C1-C6 alkyl;

wherein $R^{12a}$ is selected from hydrogen, halogen, and C1-C6 alkyl; and wherein $R^{12b}$ is selected from hydroxyl and a group having a structure represented by a formula:

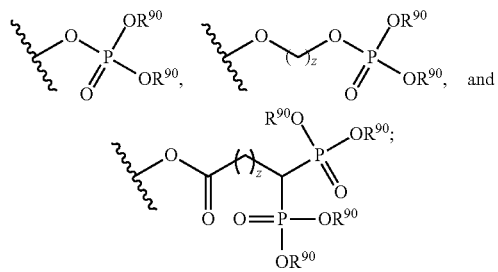

wherein z is an integer selected from 1, 2, and 3;

wherein each occurrence of $R^{90}$, when present, is independently selected from hydrogen, C1-C8 alkyl, and phenyl;

wherein $R^{13}$ is a five-membered or six-membered C3-C6 heterocycle substituted with 0-3 groups selected from halogen, cyano, C1-C6 alkyl, C1-C6 haloalkyoxy, C1-C6 haloalkyl, and C1-C6 polyhaloalkyl;

wherein each of $R^{4a}$, $R^{4b}$, $R^{4c}$, and $R^{4d}$ is independently selected from hydrogen, halogen, and C1-C6 alkyl;

wherein $R^5$ is selected from hydrogen and C1-C6 alkyl;

wherein $R^6$ is selected from hydrogen and C1-C6 alkyl; and wherein each of $R^{7a}$ and $R^{7b}$ is independently selected from hydrogen and C1-C6 alkyl, or a pharmaceutically acceptable salt, solvate, or polymorph thereof.

14. The method of claim 13, further comprising the step of identifying a mammal in need of treatment of an arthritic disease.

15. The method of claim 13, wherein the mammal has been diagnosed with a need for treatment of an arthritic disease prior to the administering step.

16. The method of claim 13, wherein the arthritic disease is selected from inflammatory arthritis, osteoarthritis, lymphocyte-independent arthritis, or rheumatoid arthritis.

* * * * *